United States Patent
Scheib et al.

(10) Patent No.: US 10,792,034 B2
(45) Date of Patent: Oct. 6, 2020

(54) VISUALIZATION OF SURGICAL DEVICES

(71) Applicant: Ethicon LLC, Guaynabo, PR (US)

(72) Inventors: Charles J. Scheib, Loveland, OH (US); Joshua Dean Young, Flanders, NJ (US)

(73) Assignee: Ethicon LLC, Guaynabo, PR (US)

( * ) Notice: Subject to any disclaimer, the term of this patent is extended or adjusted under 35 U.S.C. 154(b) by 3 days.

(21) Appl. No.: 16/128,192

(22) Filed: Sep. 11, 2018

(65) Prior Publication Data

US 2020/0015905 A1 Jan. 16, 2020

Related U.S. Application Data

(60) Provisional application No. 62/698,625, filed on Jul. 16, 2018.

(51) Int. Cl.
*A61B 17/04* (2006.01)
*A61B 17/06* (2006.01)
(Continued)

(52) U.S. Cl.
CPC ...... *A61B 17/0482* (2013.01); *A61B 1/00006* (2013.01); *A61B 1/00043* (2013.01);
(Continued)

(58) Field of Classification Search
CPC ............ A61B 17/0482; A61B 17/0469; A61B 17/0218; A61B 17/064; A61B 17/1114;
(Continued)

(56) References Cited

U.S. PATENT DOCUMENTS 5,460,182 A 10/1995 Goodman et al.
5,609,562 A 3/1997 Kaali
(Continued)

FOREIGN PATENT DOCUMENTS

JP 2006280591 A 10/2006

OTHER PUBLICATIONS

"ATM-MPLS Networking Version 2.0, of-aic-0178.001" ATM Standard, The ATM Forum Technical Committee, published Aug. 2003.
(Continued)

*Primary Examiner* — Allen C Wong

(57) ABSTRACT

A surgical visualization system is disclosed. The surgical visualization system is configured to identify one or more structure(s) and/or determine one or more distances with respect to obscuring tissue and/or the identified structure(s). The surgical visualization system can facilitate avoidance of the identified structure(s) by a surgical device. The surgical visualization system can comprise a first emitter configured to emit a plurality of tissue-penetrating light waves and a second emitter configured to emit structured light onto the surface of tissue. The surgical visualization system can also include an image sensor configured to detect reflected visible light, tissue-penetrating light, and/or structured light. The surgical visualization system can convey information to one or more clinicians regarding the position of one or more hidden identified structures and/or provide one or more proximity indicators.

20 Claims, 32 Drawing Sheets

(51) Int. Cl.

| | | |
|---|---|---|
| *A61B 17/062* | (2006.01) | |
| *A61B 34/32* | (2016.01) | |
| *A61B 34/20* | (2016.01) | |
| *A61B 34/30* | (2016.01) | |
| *A61B 1/045* | (2006.01) | |
| *A61B 1/06* | (2006.01) | |
| *A61B 1/07* | (2006.01) | |
| *A61B 1/313* | (2006.01) | |
| *A61B 17/00* | (2006.01) | |
| *A61B 17/34* | (2006.01) | |
| *A61B 17/11* | (2006.01) | |
| *A61B 17/115* | (2006.01) | |
| *A61B 17/064* | (2006.01) | |
| *A61B 90/30* | (2016.01) | |
| *A61B 90/00* | (2016.01) | |
| *A61B 1/05* | (2006.01) | |
| *A61B 1/00* | (2006.01) | |
| *A61B 5/00* | (2006.01) | |
| *A61B 90/13* | (2016.01) | |
| *A61B 34/00* | (2016.01) | |
| *A61B 90/35* | (2016.01) | |
| *A61B 17/02* | (2006.01) | |
| *A61B 1/04* | (2006.01) | |
| *A61B 34/10* | (2016.01) | |

(52) U.S. Cl.
CPC ...... *A61B 1/00045* (2013.01); *A61B 1/00096* (2013.01); *A61B 1/00149* (2013.01); *A61B 1/04* (2013.01); *A61B 1/045* (2013.01); *A61B 1/05* (2013.01); *A61B 1/051* (2013.01); *A61B 1/06* (2013.01); *A61B 1/063* (2013.01); *A61B 1/0607* (2013.01); *A61B 1/0638* (2013.01); *A61B 1/0661* (2013.01); *A61B 1/07* (2013.01); *A61B 1/3132* (2013.01); *A61B 5/0036* (2018.08); *A61B 5/0086* (2013.01); *A61B 5/0095* (2013.01); *A61B 17/00234* (2013.01); *A61B 17/0218* (2013.01); *A61B 17/0469* (2013.01); *A61B 17/0483* (2013.01); *A61B 17/062* (2013.01); *A61B 17/064* (2013.01); *A61B 17/06066* (2013.01); *A61B 17/1114* (2013.01); *A61B 17/1155* (2013.01); *A61B 17/3423* (2013.01); *A61B 34/20* (2016.02); *A61B 34/30* (2016.02); *A61B 34/32* (2016.02); *A61B 34/73* (2016.02); *A61B 90/03* (2016.02); *A61B 90/13* (2016.02); *A61B 90/30* (2016.02); *A61B 90/35* (2016.02); *A61B 90/36* (2016.02); *A61B 90/361* (2016.02); *A61B 90/37* (2016.02); *A61B 1/00009* (2013.01); *A61B 1/0676* (2013.01); *A61B 2017/00061* (2013.01); *A61B 2017/00119* (2013.01); *A61B 2017/00367* (2013.01); *A61B 2017/00477* (2013.01); *A61B 2017/00876* (2013.01); *A61B 2034/105* (2016.02); *A61B 2034/107* (2016.02); *A61B 2034/2051* (2016.02); *A61B 2034/2055* (2016.02); *A61B 2034/2057* (2016.02); *A61B 2034/2063* (2016.02); *A61B 2034/2065* (2016.02); *A61B 2034/301* (2016.02); *A61B 2034/302* (2016.02); *A61B 2090/061* (2016.02); *A61B 2090/064* (2016.02); *A61B 2090/306* (2016.02); *A61B 2090/367* (2016.02); *A61B 2090/373* (2016.02); *A61B 2090/374* (2016.02); *A61B 2090/378* (2016.02); *A61B 2090/3762* (2016.02); *A61B 2505/05* (2013.01); *A61B 2560/0462* (2013.01); *A61B 2576/00* (2013.01)

(58) Field of Classification Search
CPC .......... A61B 17/1155; A61B 17/00234; A61B 17/3423; A61B 17/0483; A61B 17/06066; A61B 17/062; A61B 90/03; A61B 90/35; A61B 90/361; A61B 90/13; A61B 90/30; A61B 90/36; A61B 34/73; A61B 34/32; A61B 34/20; A61B 1/00149; A61B 1/051; A61B 1/04; A61B 1/00043; A61B 1/00096; A61B 1/00006; A61B 1/00045; A61B 1/0661; A61B 1/05; A61B 1/06; A61B 1/045; A61B 1/0607; A61B 1/063; A61B 1/0638; A61B 1/07; A61B 1/3132; A61B 1/0676; A61B 5/0095; A61B 5/0036; A61B 5/0086; A61B 2017/00477; A61B 2017/00876; A61B 2017/00119; A61B 2017/00061; A61B 2017/00367; A61B 2090/064; A61B 2090/374; A61B 2090/3762; A61B 2090/378; A61B 2090/061; A61B 2090/306; A61B 2090/367; A61B 2090/373; A61B 2505/05; A61B 2576/00; A61B 2560/0462

USPC .......................................................... 348/77
See application file for complete search history.

(56) References Cited

U.S. PATENT DOCUMENTS

| | | |
|---|---|---|
| 6,350,233 B1 | 2/2002 | Lubowski |
| 7,901,353 B2 | 3/2011 | Vayser et al. |
| 8,932,208 B2 | 1/2015 | Kendale et al. |
| 8,992,558 B2 | 3/2015 | Stone et al. |
| 9,072,501 B2 | 7/2015 | Menchaca et al. |
| 9,072,535 B2 | 7/2015 | Shelton, IV et al. |
| 9,161,820 B2 | 10/2015 | Mark et al. |
| 9,179,822 B2 | 11/2015 | Kitamura et al. |
| 9,241,693 B2 | 1/2016 | Taylor et al. |
| 9,274,047 B2 | 3/2016 | Velten et al. |
| 9,282,878 B2 | 3/2016 | Grey et al. |
| 10,068,173 B2 | 9/2018 | Vayser et al. |
| 10,512,518 B2 | 12/2019 | Vayser et al. |
| 2005/0279354 A1 | 12/2005 | Deutsch et al. |
| 2006/0206007 A1 | 9/2006 | Bala |
| 2007/0100210 A1 | 5/2007 | Selover et al. |
| 2010/0152539 A1 | 6/2010 | Ghabrial et al. |
| 2012/0265022 A1 | 10/2012 | Menn |
| 2016/0038004 A1 | 2/2016 | Tanaka |
| 2016/0183841 A1* | 6/2016 | Duindam .......... A61M 25/0105 600/424 |
| 2016/0278755 A1 | 9/2016 | Stone et al. |
| 2016/0377417 A1* | 12/2016 | Jovanovski ............ H04N 5/225 348/136 |
| 2017/0055819 A1 | 3/2017 | Hansen et al. |
| 2017/0251900 A1 | 9/2017 | Hansen et al. |
| 2018/0014851 A1 | 1/2018 | Hansen et al. |
| 2018/0028063 A1* | 2/2018 | Elbaz .................. A61B 5/0088 |
| 2019/0099070 A1 | 4/2019 | Mark et al. |
| 2019/0200905 A1 | 7/2019 | Shelton, IV et al. |
| 2019/0201047 A1 | 7/2019 | Yates et al. |
| 2019/0201111 A1 | 7/2019 | Shelton, IV et al. |
| 2019/0201120 A1 | 7/2019 | Shelton, IV et al. |
| 2019/0201142 A1 | 7/2019 | Shelton, IV et al. |
| 2020/0015668 A1 | 1/2020 | Scheib |
| 2020/0015806 A1 | 1/2020 | Scheib et al. |
| 2020/0015897 A1 | 1/2020 | Scheib et al. |
| 2020/0015898 A1 | 1/2020 | Scheib et al. |
| 2020/0015899 A1 | 1/2020 | Scheib et al. |
| 2020/0015900 A1 | 1/2020 | Scheib et al. |
| 2020/0015901 A1 | 1/2020 | Scheib et al. |
| 2020/0015902 A1 | 1/2020 | Scheib et al. |
| 2020/0015903 A1 | 1/2020 | Scheib et al. |
| 2020/0015904 A1 | 1/2020 | Scheib et al. |
| 2020/0015906 A1 | 1/2020 | Scheib et al. |

(56) References Cited

U.S. PATENT DOCUMENTS

| | | |
|---|---|---|
| 2020/0015907 A1 | 1/2020 | Scheib |
| 2020/0015914 A1 | 1/2020 | Scheib et al. |
| 2020/0015923 A1 | 1/2020 | Scheib et al. |
| 2020/0015924 A1 | 1/2020 | Scheib et al. |
| 2020/0015925 A1 | 1/2020 | Scheib |
| 2020/0037858 A1 | 2/2020 | Pedreira de Cerqueira Filho |

OTHER PUBLICATIONS

Elhajj, et al., "Sleeve Gastrectomy Surgical Assistive Instrument for Accurate Remnant Stomach Volume," ASME, J. Med. Devices, vol. 4, pp. 1-10, Jun. 2010.
IEEE Std 802.Mar. 2012 (Revision of IEEE Std 802.Mar. 2008, published Dec. 28, 2012.
Kurata et al. "Time-of-flight Near-infrared Spectroscopy for Non-destructive Measurement of Internal Quality in Grapefruit," J. Amer. Soc. Hort. Sci. 138(3): 225-228, 2013.
Lacy, Antonio, "Main Steps to Perform a Sleeve Gastrectomy," retrieved from https://aischannel.com/society/main-steps-to-perform-a-sleeve-gastrectomy/ on Feb. 14, 2020. pp. 1-7, Jun. 11, 2015.
Open Technique for Low Anterior Resection, retrieved from https://abdominalkey.com/open-technique-for-low-anterior-resection/ on Feb. 4, 2020. 6 pages.
Sukumar et al., "Robotic Partial Nephrectomy Using Robotic Bulldog Clamps," JSLS: Journal of the Society of Laparoendoscopic Surgeons, 15(4), pp. 520-526, 2011.
Thyroid Fine Needle Aspiration (FNA) Biopsy, retrieved from www.fairview.org/patient-education/90246 on Feb. 4, 2020. 3 pages.
X12C4 Robotic Drop-In, retrieved from https://bkultrasound.com/transducers/x12c4-robotic-drop-in on Feb. 13, 2020. 2 pages.

* cited by examiner

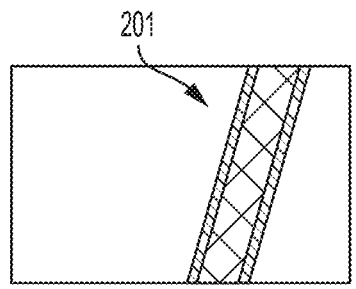
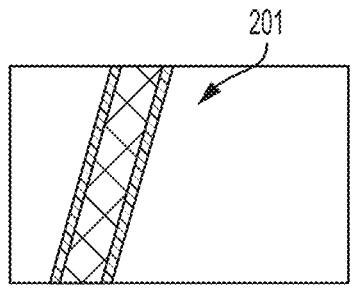
FIG. 7A  FIG. 7B
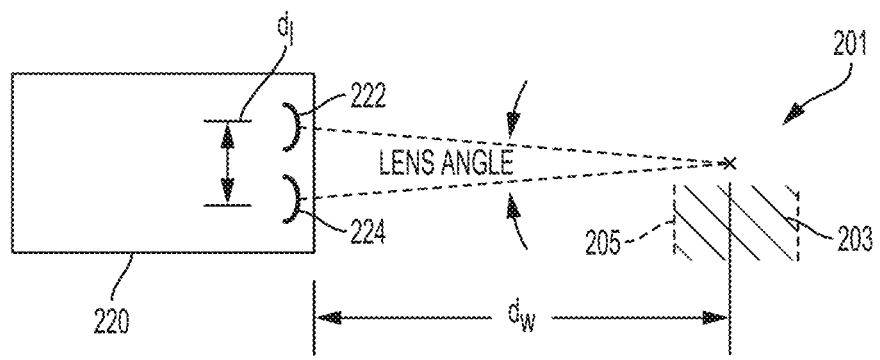
FIG. 8

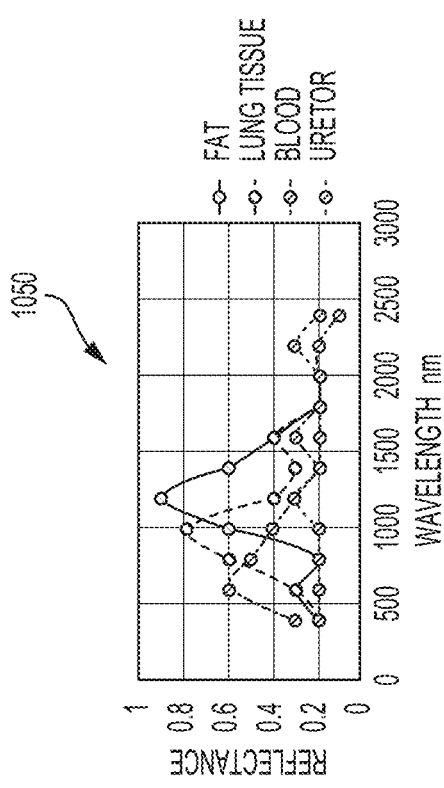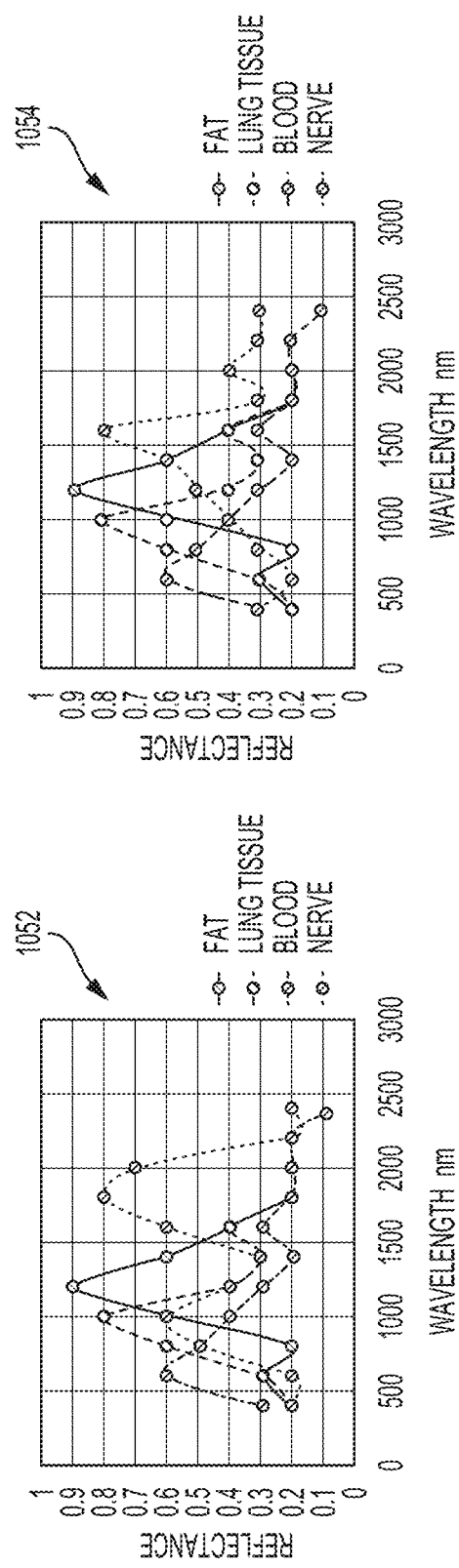

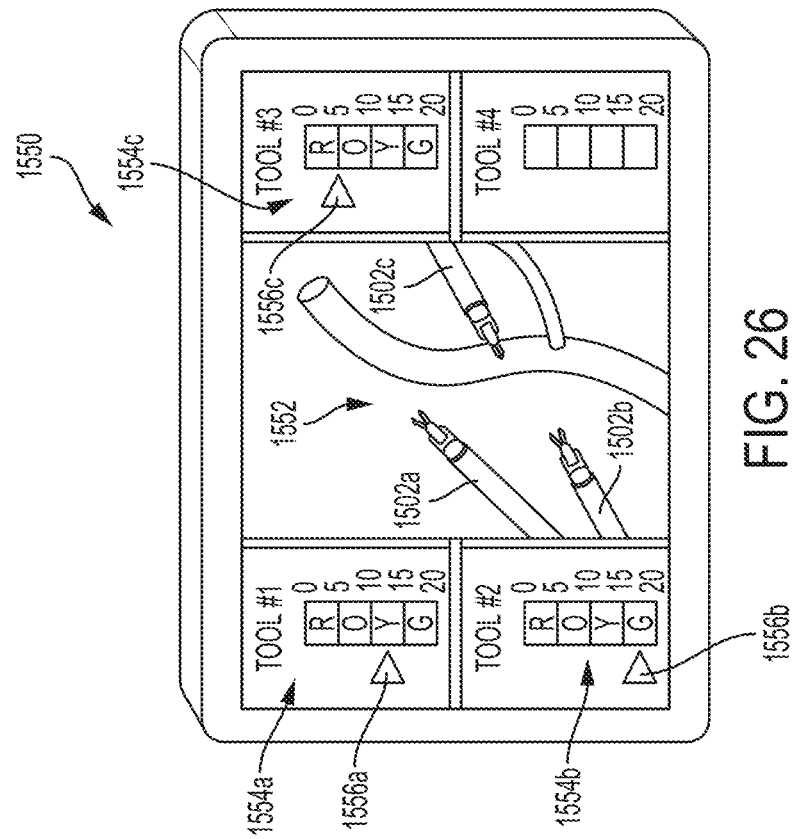
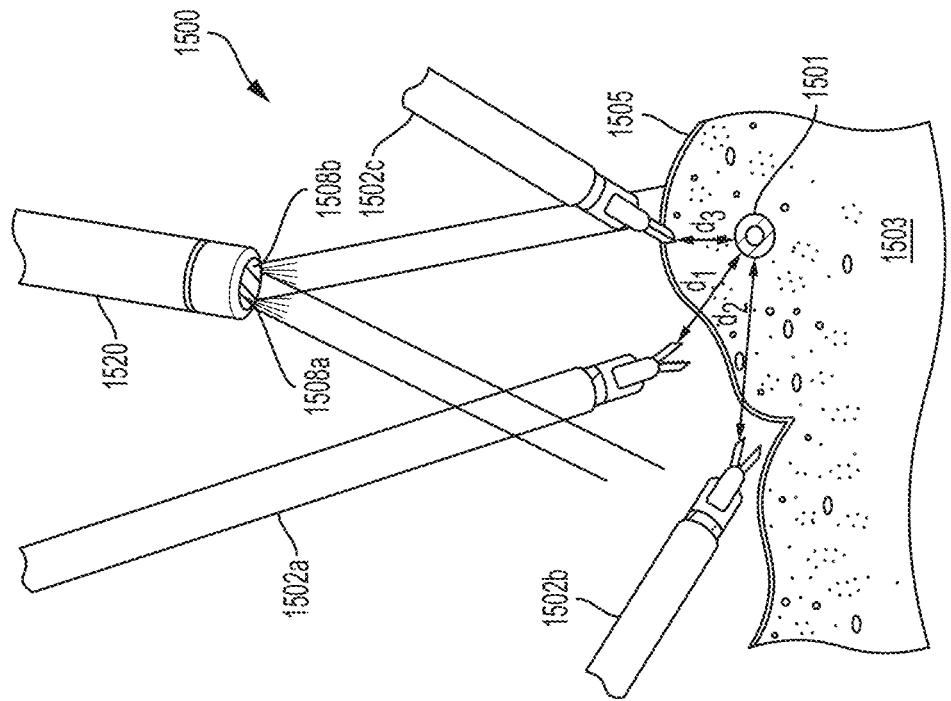

VISUALIZATION OF SURGICAL DEVICES

CROSS-REFERENCE TO RELATED APPLICATION

This application claims the benefit of priority under 35 U.S.C. § 119(e) to U.S. Provisional Patent Application Ser. No. 62/698,625, titled DIGITAL SURGERY IMAGING/VISUALIZATION SYSTEM, filed Jul. 16, 2018, the disclosure of which is herein incorporated by reference in its entirety.

BACKGROUND

Surgical systems often incorporate an imaging system, which can allow the clinician(s) to view the surgical site and/or one or more portions thereof on one or more displays such as a monitor, for example. The display(s) can be local and/or remote to a surgical theater. An imaging system can include a scope with a camera that views the surgical site and transmits the view to a display that is viewable by a clinician. Scopes include, but are not limited to, arthroscopes, angioscopes, bronchoscopes, choledochoscopes, colonoscopes, cytoscopes, duodenoscopes, enteroscopes, esophagogastro-duodenoscopes (gastroscopes), endoscopes, laryngoscopes, nasopharyngo-neproscopes, sigmoidoscopes, thoracoscopes, ureteroscopes, and exoscopes. Imaging systems can be limited by the information that they are able to recognize and/or convey to the clinician(s). For example, certain concealed structures, physical contours, and/or dimensions within a three-dimensional space may be unrecognizable intraoperatively by certain imaging systems. Additionally, certain imaging systems may be incapable of communicating and/or conveying certain information to the clinician(s) intraoperatively.

SUMMARY

A surgical visualization system can comprise a first projector configured to emit a structured light pattern on a surface of an anatomical structure, a second projector configured to emit spectral light in a plurality of wavelengths capable of penetrating the anatomical structure and reaching a staple line, and a control circuit in signal communication with an image sensor, wherein the control circuit is configured to receive structured light data from the image sensor indicative of the structured light pattern on the surface of the anatomical structure, calculate a three-dimensional representation of the anatomical structure from the structured light data, receive spectral light data from the image sensor indicative of a spectral image of the staple line, generate the spectral image of the staple line from the spectral light data, and determine a distance with respect to the staple line.

A surgical visualization system can comprise a processor and a memory communicatively coupled to the processor, wherein the memory stores instructions which, when executed by the processor receive structured light data from an image sensor indicative of a structured light pattern on a surface of an anatomical structure, calculate a three-dimensional representation of the anatomical structure from the structured light data, receive spectral light data from the image sensor indicative of a spectral image of a staple line, generate a spectral image of the staple line from the spectral light data, and determine a distance with respect to the staple line.

A non-transitory computer readable medium can store computer readable instructions which, when executed, cause a machine to receive structured light data from an image sensor indicative of a structured light pattern on a surface of an anatomical structure, calculate a three-dimensional representation of the anatomical structure from the structured light data, receive spectral light data from the image sensor indicative of a spectral image of a staple line, generate a spectral image of the staple line from the spectral light data, and determine a distance with respect to the staple line.

FIGURES

The novel features of the various aspects are set forth with particularity in the appended claims. The described aspects, however, both as to organization and methods of operation, may be best understood by reference to the following description, taken in conjunction with the accompanying drawings in which:

FIGS. 7A and 7B are views of the critical structure taken by the three-dimensional camera of FIG. 6, in which FIG. 7A is a view from a left-side lens of the three-dimensional camera and FIG. 7B is a view from a right-side lens of the three-dimensional camera, according to at least one aspect of the present disclosure.

FIG. 8 is a schematic of the surgical visualization system of FIG. 6, in which a camera-to-critical structure distance $d_w$ from the three-dimensional camera to the critical structure can be determined, according to at least one aspect of the present disclosure.

Figure 15A:
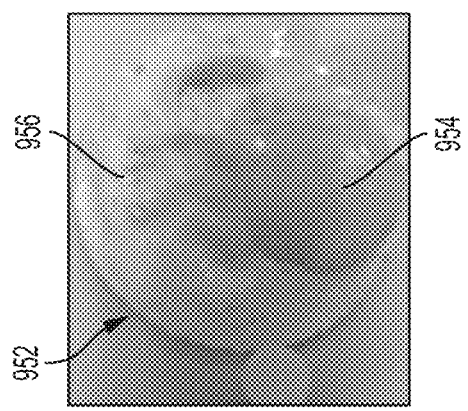
Figure 15B:
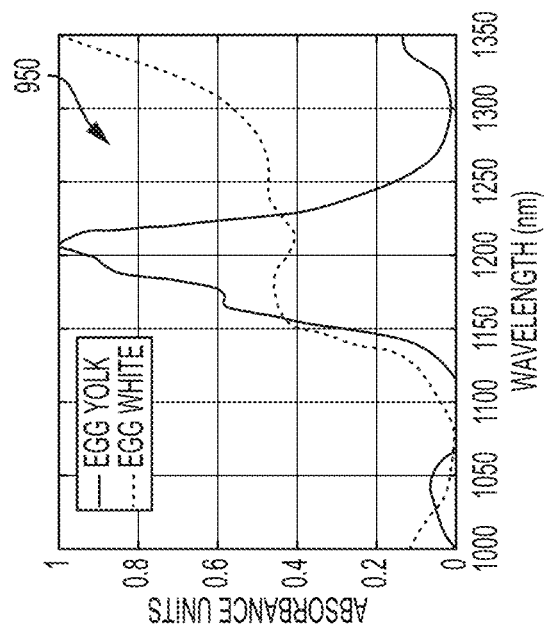
Figure 15C:
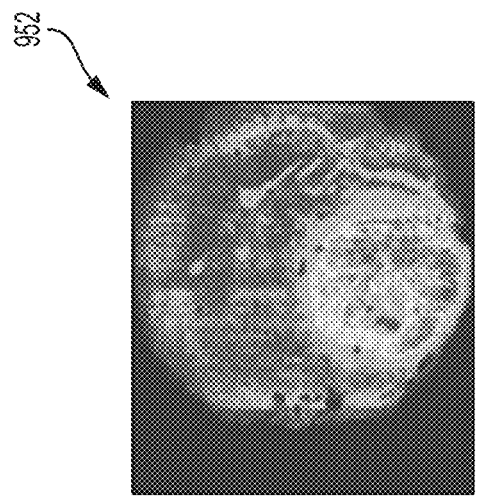

FIGS. 15A-15C show an example of a hyperspectral visualization system for imaging a fried egg, wherein FIG. 15A is a photograph of the fried egg, FIG. 15B is a graphical representation of hyperspectral signatures for an egg yolk portion and an egg white portion of the fried egg, and FIG. 15C is a hyperspectral image (shown in black-and-white) of the fried egg, in which an augmented image differentiates between the egg yolk portion and the egg white portion based on hyperspectral signature data, according to at least one aspect of the present disclosure.

FIGS. 16-18 depict illustrative hyperspectral identifying signatures to differentiate anatomy from obscurants, wherein FIG. 16 is a graphical representation of a ureter signature versus obscurants, FIG. 17 is a graphical representation of an artery signature versus obscurants, and FIG. 18 is a graphical representation of a nerve signature versus obscurants, according to at least one aspect of the present disclosure.

Figure 19:
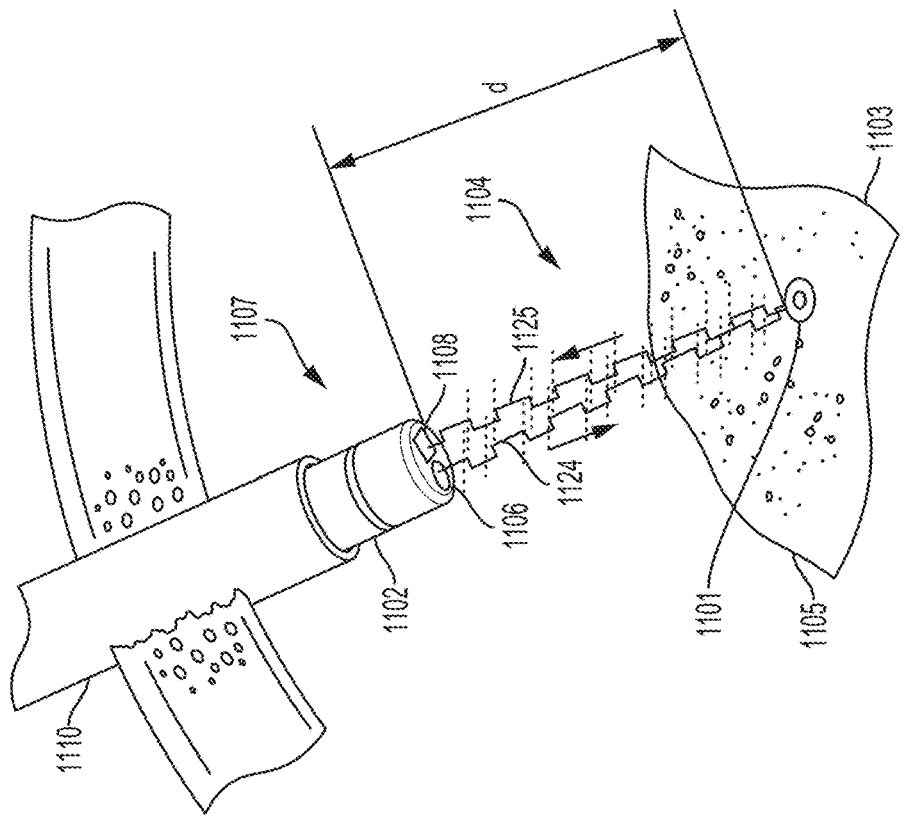

FIG. 19 is a schematic of a near infrared (NIR) time-of-flight measurement system configured to sense distance to a critical anatomical structure, the time-of-flight measurement system including a transmitter (emitter) and a receiver (sensor) positioned on a common device, according to at least one aspect of the present disclosure.

Figure 20:
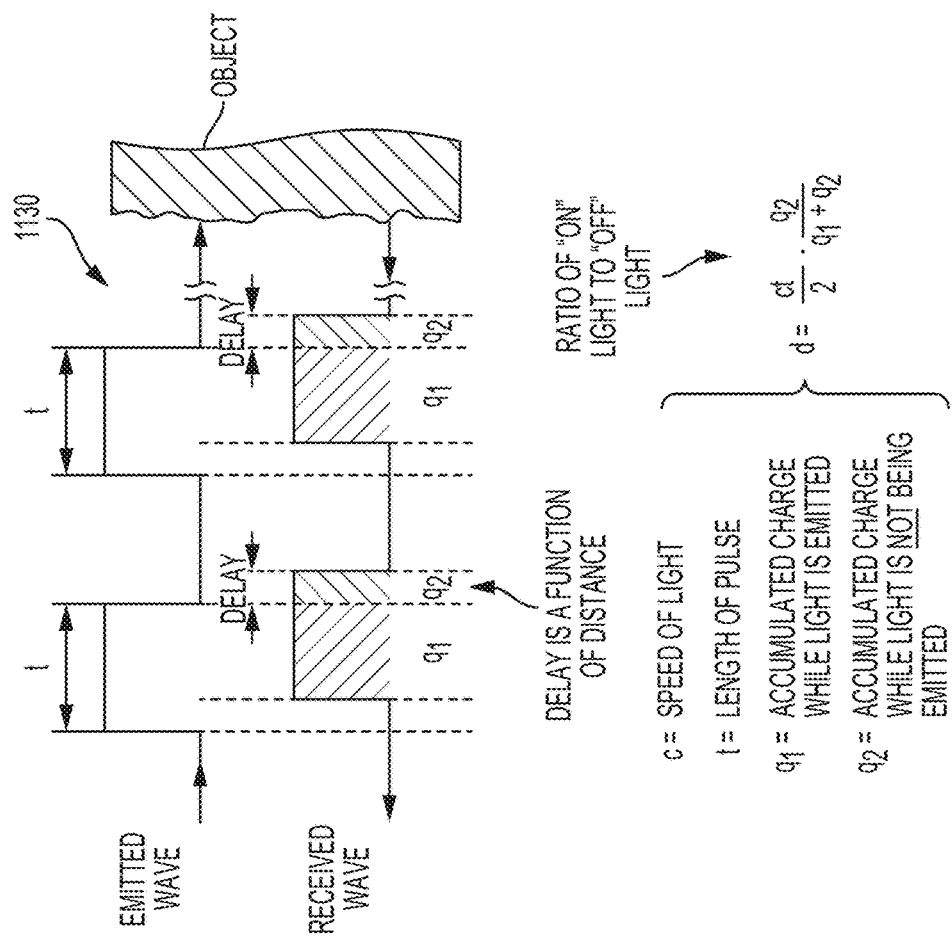

FIG. 20 is a schematic of an emitted wave, a received wave, and a delay between the emitted wave and the received wave of the NIR time-of-flight measurement system of FIG. 19, according to at least one aspect of the present disclosure.

Figure 21:
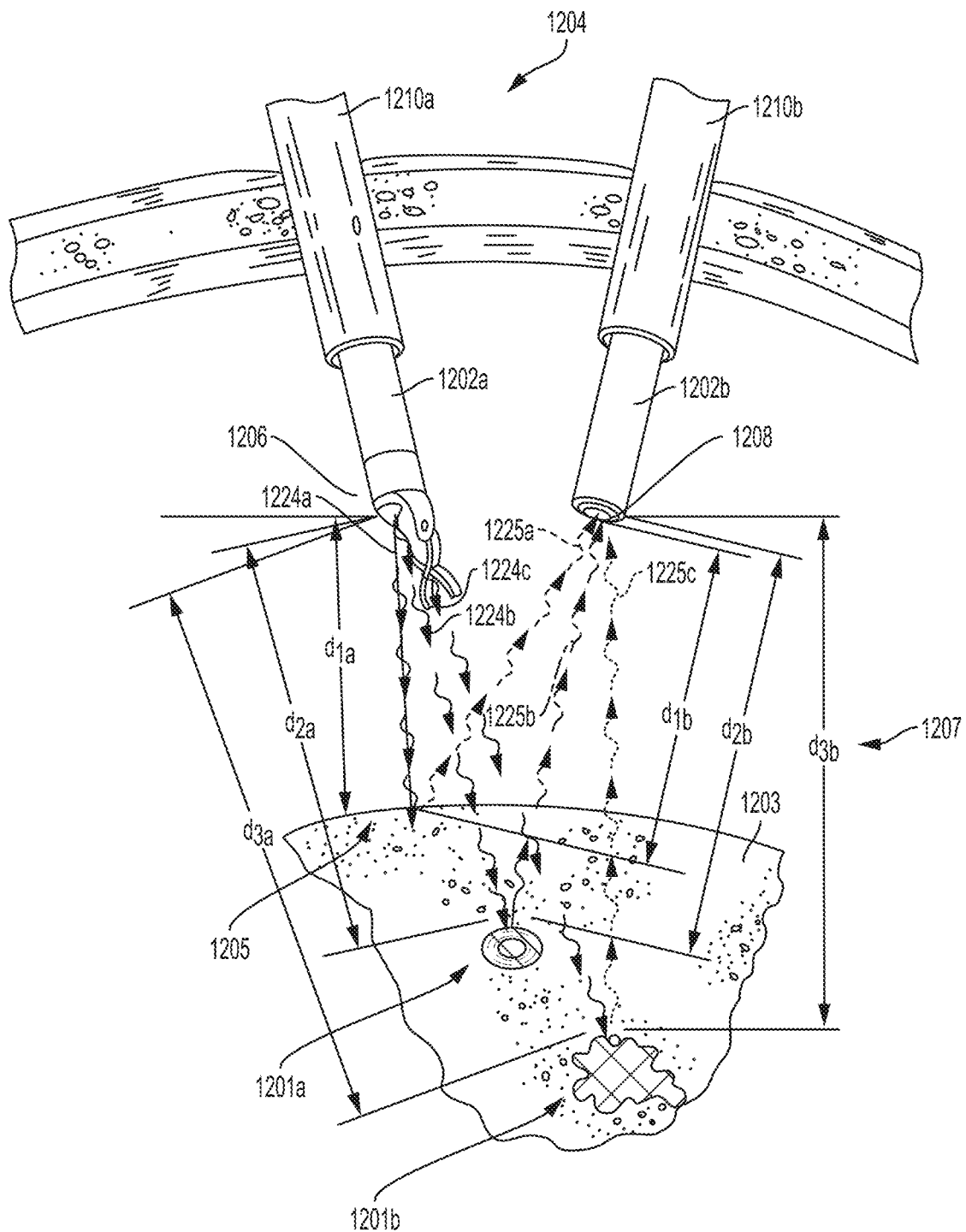

FIG. 21 illustrates a NIR time-of-flight measurement system configured to sense a distance to different structures, the time-of-flight measurement system including a transmitter (emitter) and a receiver (sensor) on separate devices, according to one aspect of the present disclosure.

Figure 22:
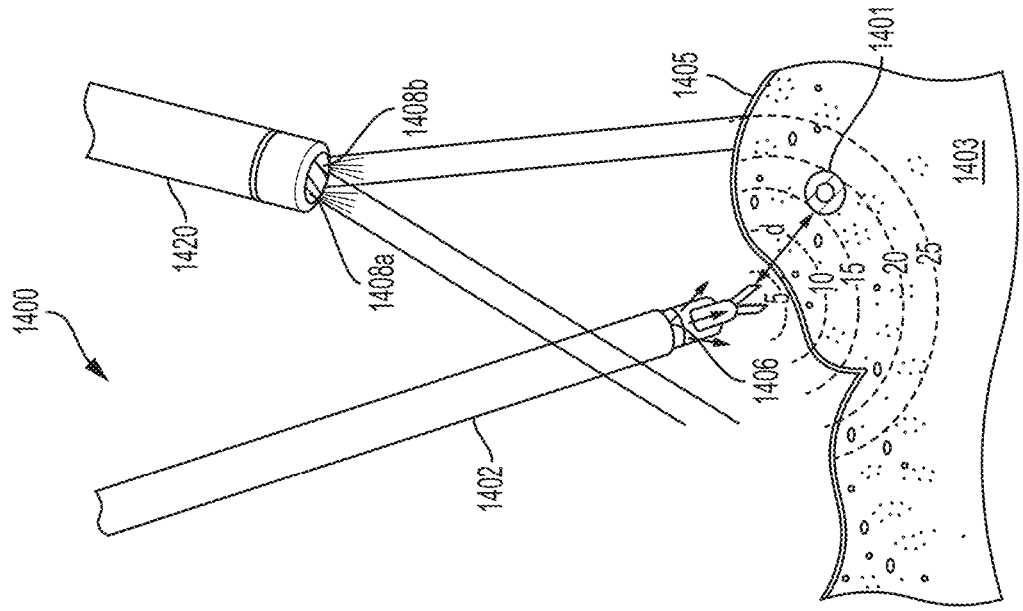

FIG. 22 is a schematic of a surgical visualization system including a three-dimensional camera and a surgical device having an emitter, the surgical visualization system configured to determine a distance from the surgical device to a critical structure below a tissue surface, according to at least one aspect of the present disclosure.

Figure 23:
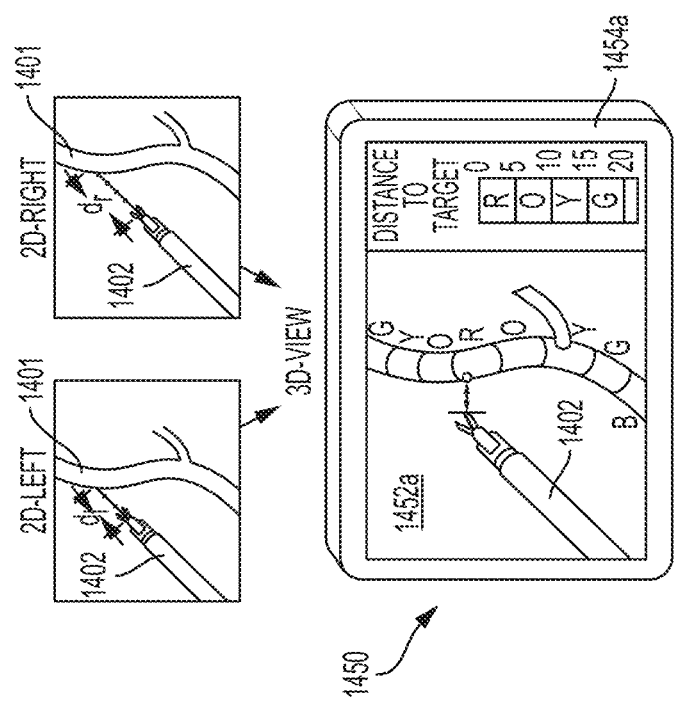

FIG. 23 illustrates views of a surgical site obtained with a two-dimensional left-side lens and a two-dimensional right-side lens of the three-dimensional camera of FIG. 22, which are combined to produce a three-dimensional view on a display screen, wherein the display screen further indicates the distance from the surgical device of FIG. 22 to the critical structure with color coding augmented on the view of the critical structure, according to at least aspect of the present disclosure.

Figure 24:
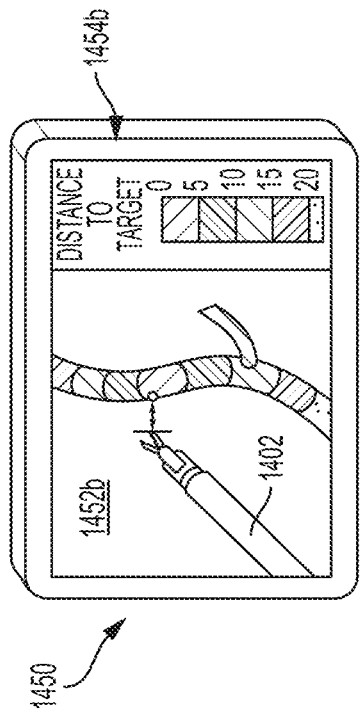

FIG. 24 is a schematic of the display screen of FIG. 23 depicting a three-dimensional view obtained by the three-dimensional camera of FIG. 22 and indicating the distance from the surgical device of FIG. 22 to the critical structure with cross-hatching augmented on the view of the critical structure, according to at least aspect of the present disclosure.

FIG. 25 is a schematic of a surgical visualization system including a three-dimensional camera and three surgical devices, the surgical visualization system configured to determine the distance from each surgical device to a critical structure below a tissue surface, according to at least one aspect of the present disclosure.

FIG. 26 is a schematic of a screen depicting a three-dimensional view obtained from the three-dimensional camera of FIG. 25 and indicating the distances from the surgical devices of FIG. 25 to the critical structure with proximity spectrum indicators, according to at least one aspect of the present disclosure.

Figure 27:
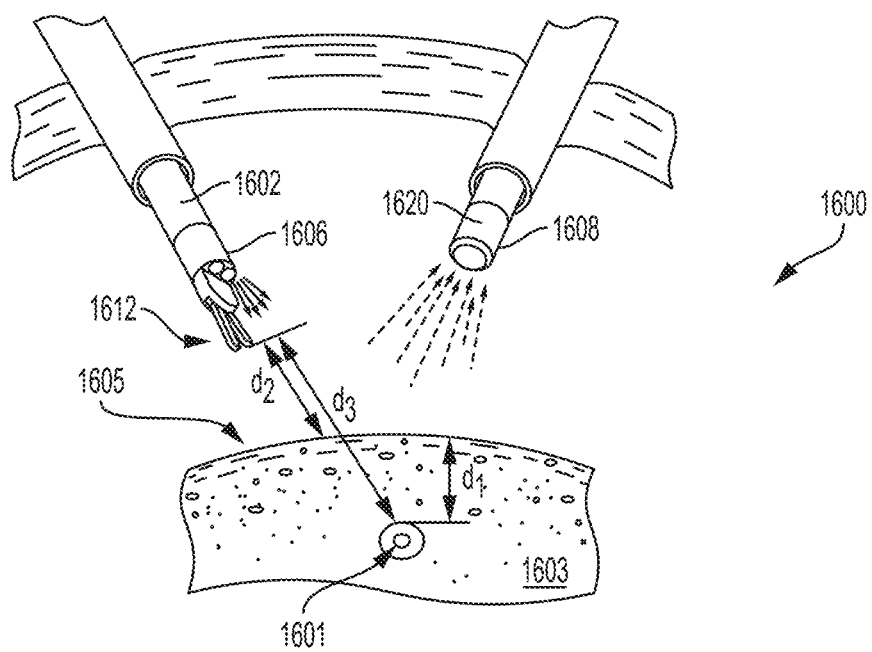

FIG. 27 is a schematic of a surgical visualization system including a camera and a surgical device having an emitter, the surgical visualization system configured to determine a device-to-surface distance from the distal end of the surgical device to a tissue surface, a device-to-vessel distance from the distal end of the surgical device to a vessel below the tissue surface, and a surface-to-vessel distance (depth of the critical structure below the tissue surface), according to at least one aspect of the present disclosure.

Figure 28:
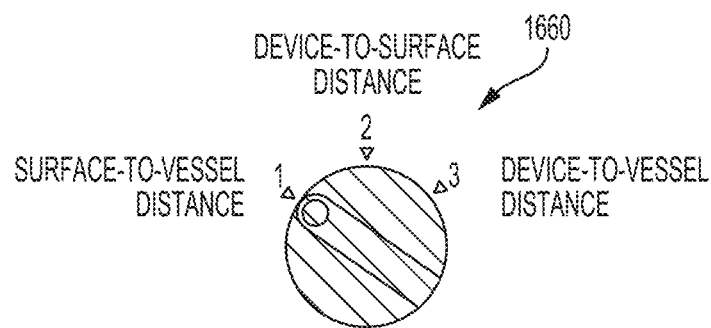

FIG. 28 is a schematic of a dial for selecting a display setting corresponding to the device-to-surface distance, the device-to-vessel distance, or the surface-to-vessel distance for the surgical visualization system of FIG. 27, according to at least one aspect of the present disclosure.

Figure 29:
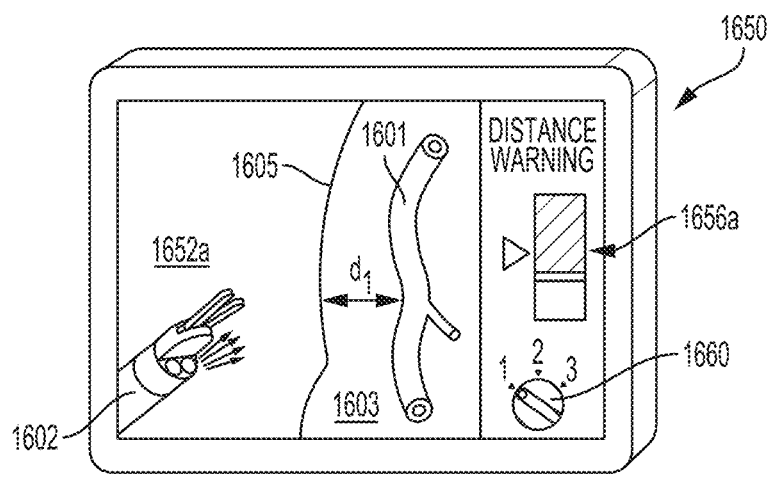

FIG. 29 is a schematic of a screen for the surgical visualization system of FIG. 27, displaying the dial of FIG. 28 in a first position in which the surface-to-vessel distance is selected, and wherein the screen is displaying a view that includes a first aggregation of data related to the surface-to-vessel distance, according to at least one aspect of the present disclosure.

Figure 30:
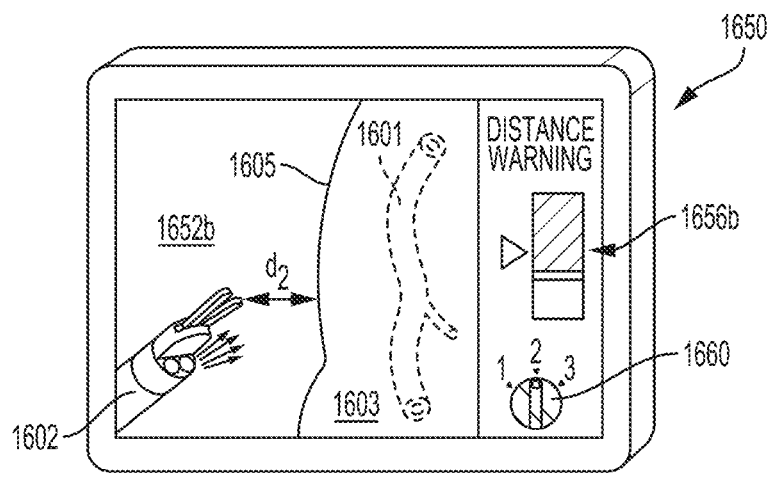

FIG. 30 is a schematic of the screen of FIG. 29, displaying the dial of FIG. 28 in a second position in which the device-to-surface distance is selected, and wherein the display is displaying a view that includes a second aggregation of data related to the device-to-surface distance, according to at least one aspect of the present disclosure.

Figure 31:
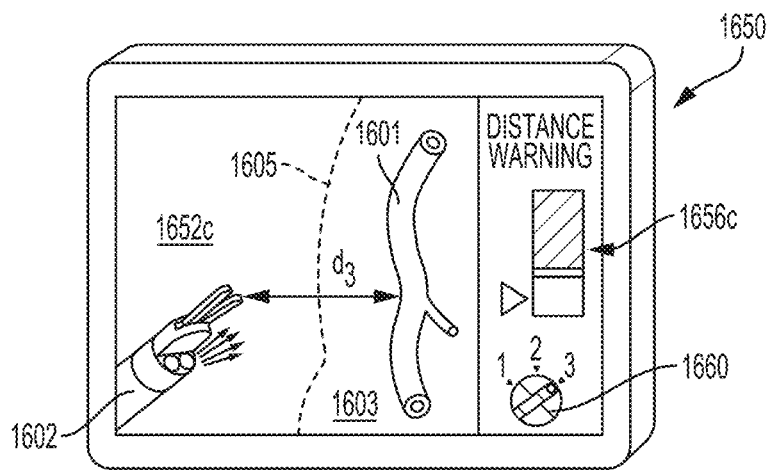

FIG. 31 is a schematic of the screen of FIG. 29, depicting the dial of FIG. 28 in a third position in which the device-to-vessel distance is selected, and wherein the screen is displaying a view that includes a third aggregation of data related to the device-to-vessel distance, according to at least one aspect of the present disclosure.

Figure 32:
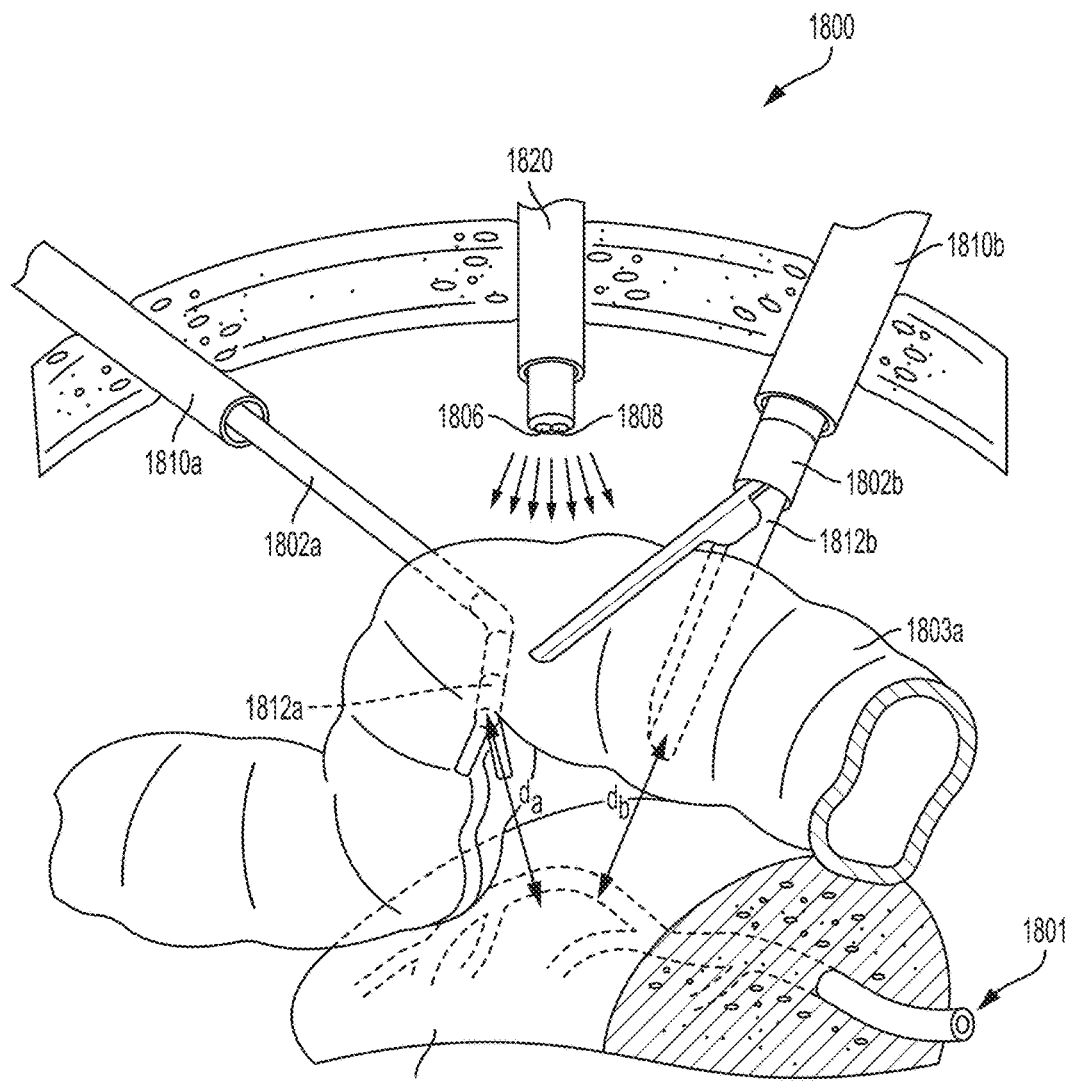

FIG. 32 is a schematic of a surgical visualization system including a spectral imaging camera configured to identify hidden anatomical structures and surgical devices, according to at least one aspect of the present disclosure.

Figure 33:
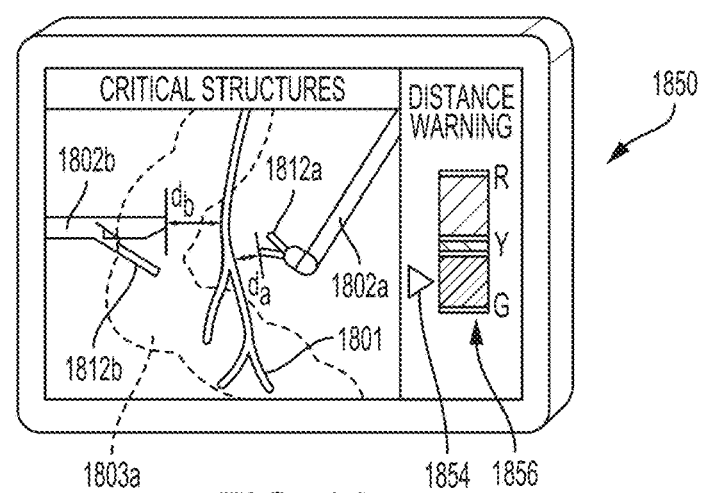

FIG. 33 is a schematic of a screen for the surgical visualization system of FIG. 32, wherein the screen is displaying an augmented view of the surgical site that includes a hidden anatomical structure and hidden surgical devices, and wherein the screen further depicts a proximity spectrum indicator conveying the proximity of the hidden surgical devices relative to the anatomical structures, according to at least one aspect of the present disclosure.

Figure 34:
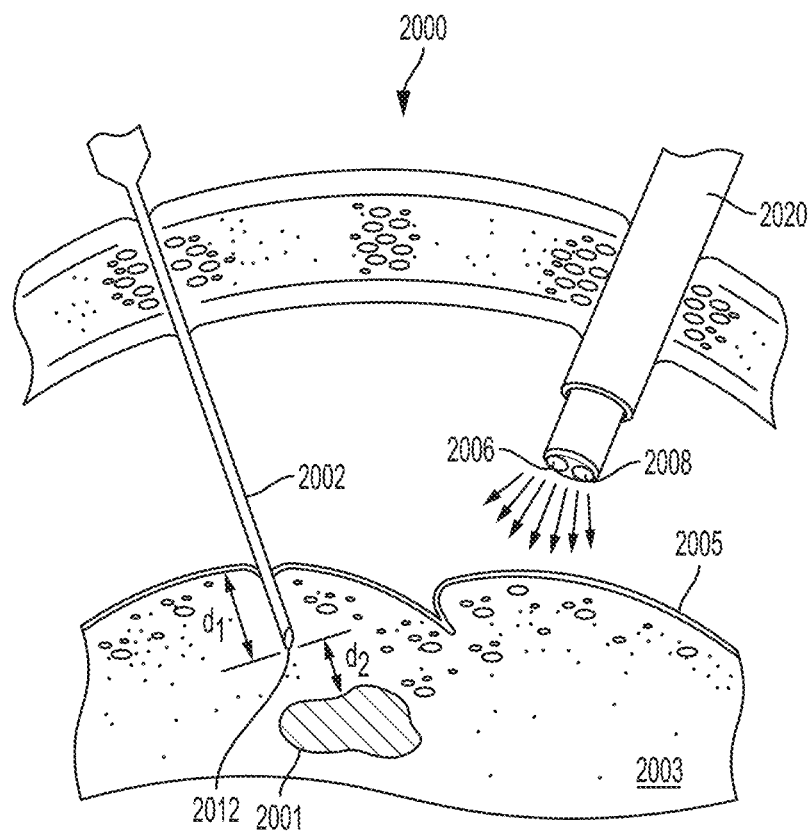

FIG. 34 is a schematic of a surgical visualization system including a spectral imaging camera configured to identify a biopsy needle in a first position relative to an embedded tumor, according to at least one aspect of the present disclosure.

Figure 35:
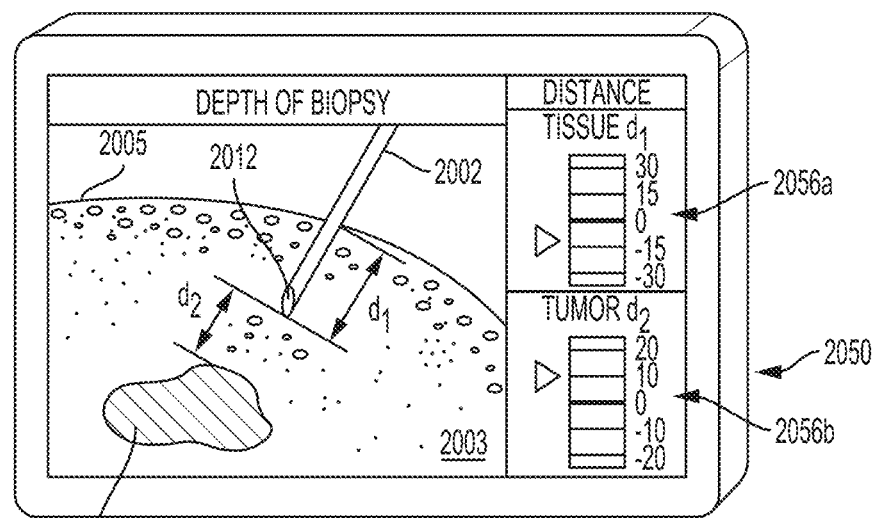

FIG. 35 is a schematic of a screen for the surgical visualization system of FIG. 34, wherein the screen is displaying an augmented view of the surgical site that includes the tumor and the biopsy needle in the first position, and wherein the screen further depicts proximity spectrum indicators conveying the proximity of the biopsy needle to the tumor and to a surface of obstructing tissue in the first position, according to at least one aspect of the present disclosure.

Figure 36:
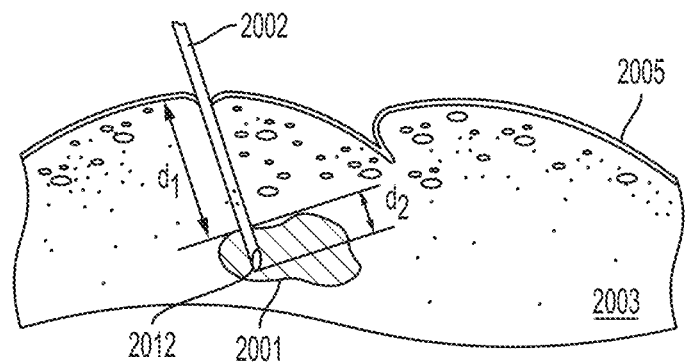

FIG. 36 is a schematic of the surgical visualization system of FIG. 34 depicting the biopsy needle in a second position relative to the embedded tumor, according to at least one aspect of the present disclosure.

Figure 37:
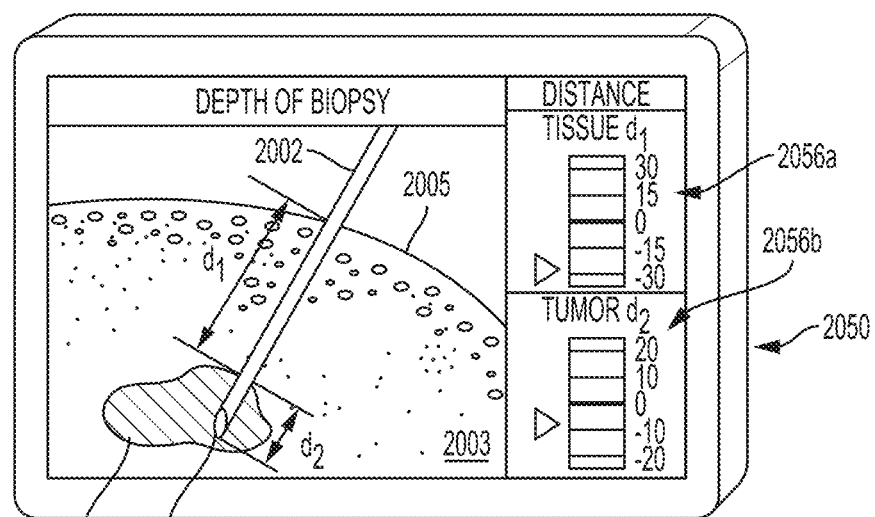

FIG. 37 is a schematic of the screen of FIG. 35 displaying an augmented view of the surgical site that includes the tumor and the biopsy needle in the second position, and wherein the screen further depicts proximity spectrum indicators conveying the proximity of the biopsy needle to the tumor and to the surface of obstructing tissue in the second position, according to at least one aspect of the present disclosure.

Figure 38:
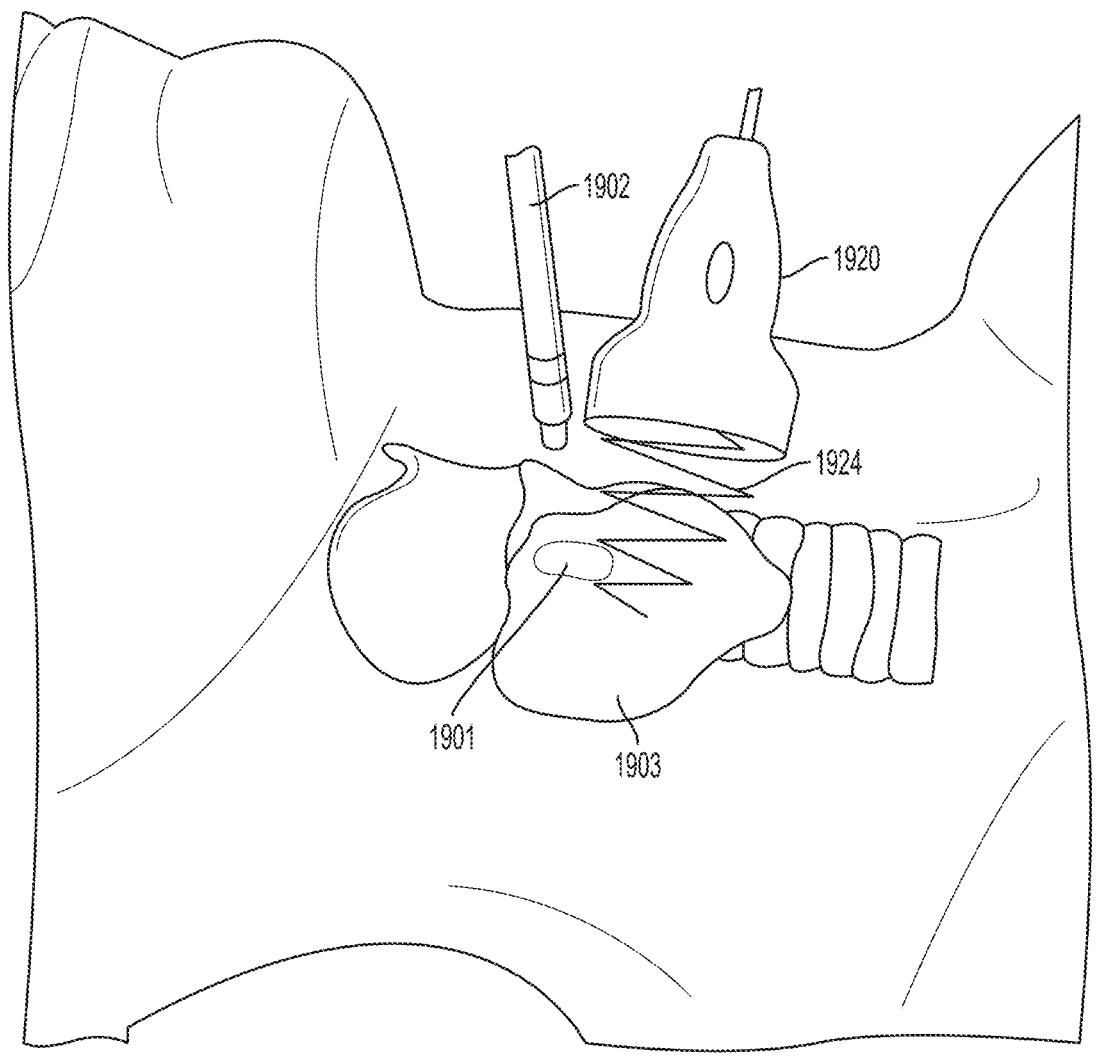

FIG. 38 is a schematic of a biopsy procedure in which an ultrasound device is being used to identify a tumor in a thyroid, according to at least one aspect of the present disclosure.

Figure 41:
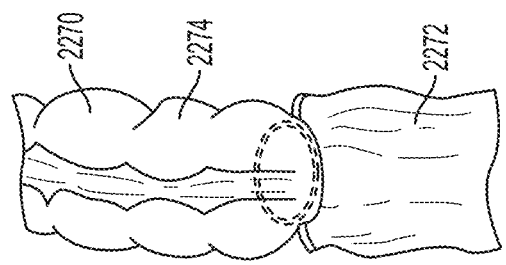
Figure 40:
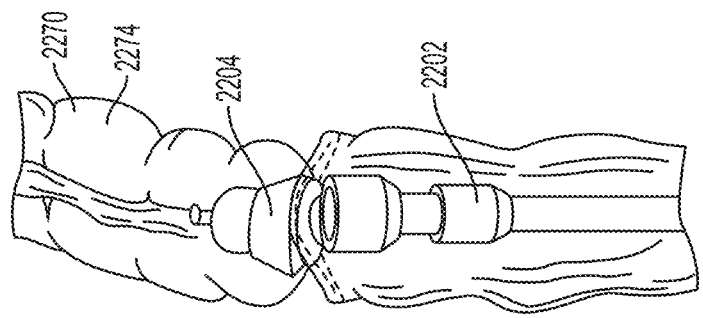
Figure 39:
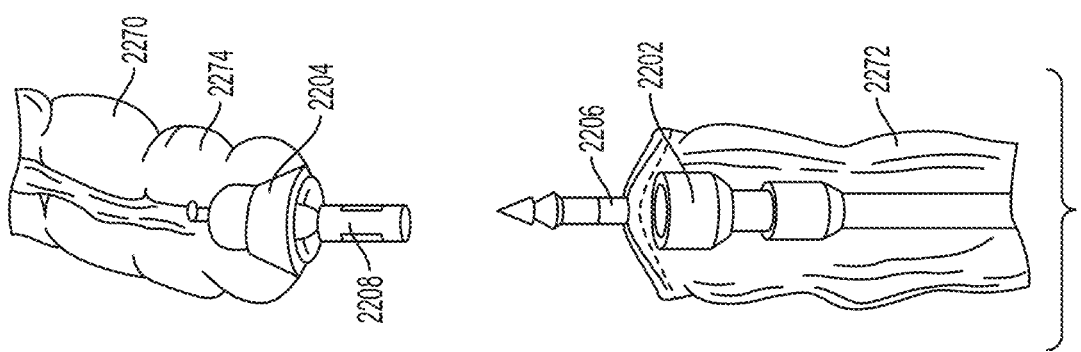

FIGS. 39-41 depict an example of an anastomosis step during a lower anterior resection (LAR) procedure of a colon, in which FIG. 39 depicts a circular stapler and an anvil separated, FIG. 40 depicts the circular stapler and the anvil coupled together for firing, and FIG. 41 depicts portions of the colon stapled together after the firing, according to at least one aspect of the present disclosure.

Figure 42:
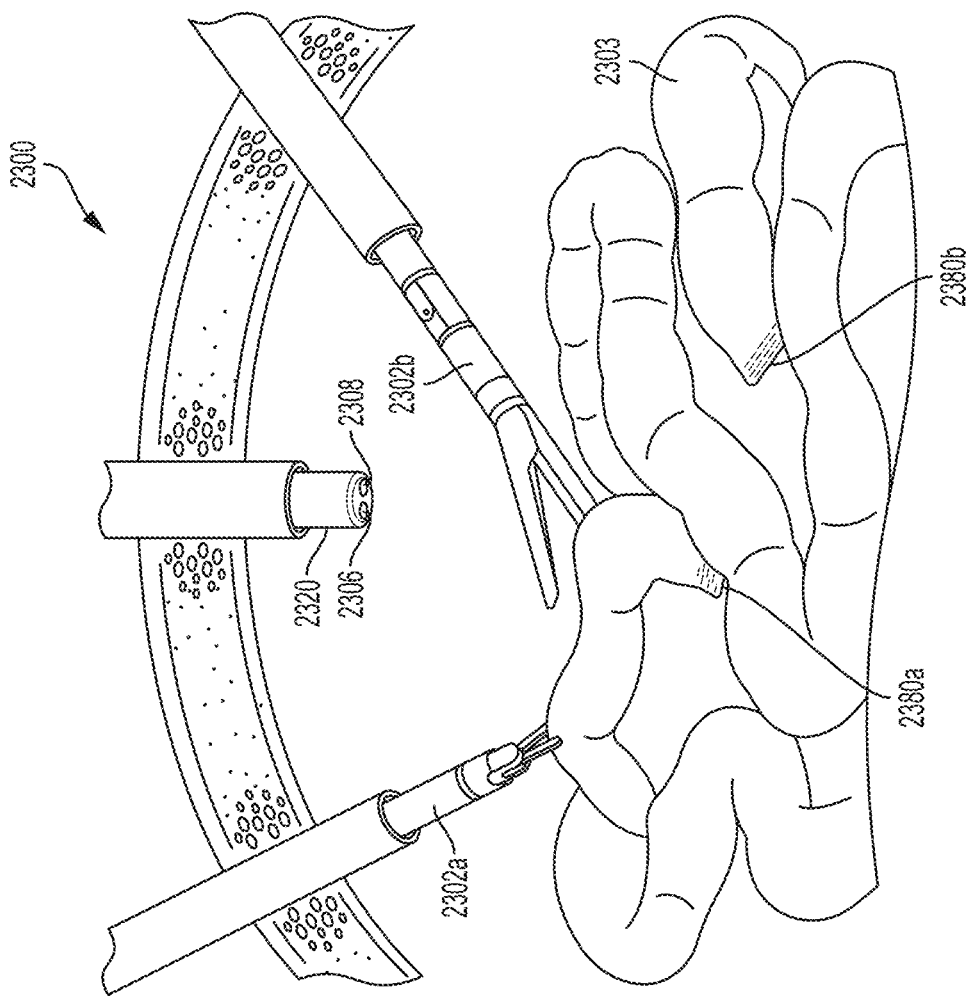

FIG. 42 is a schematic of a surgical visualization system including a spectral imaging camera configured to identify hidden surgical devices and staple lines, according to at least one aspect of the present disclosure.

Figure 43:
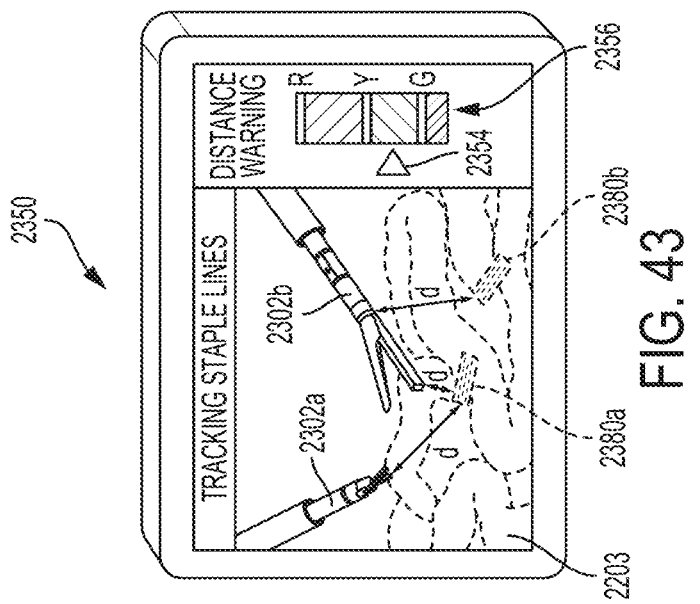

FIG. 43 is a schematic of a screen for the surgical visualization system of FIG. 42, wherein the screen is displaying an augmented view of the surgical site that includes the hidden staples lines and surgical devices, and wherein the screen further depicts a proximity spectrum indicator conveying the proximity of the surgical devices relative to the staple lines, according to at least one aspect of the present disclosure.

Figure 44:
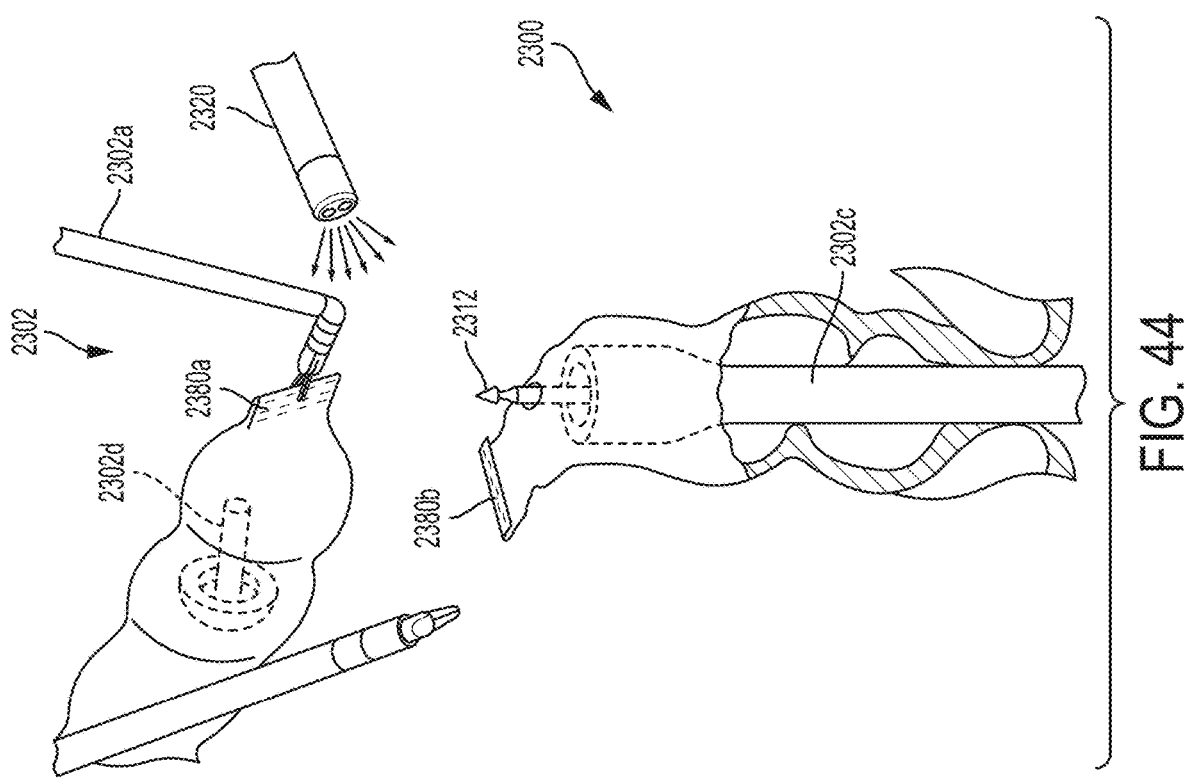

FIG. 44 is a schematic of the surgical visualization system of FIG. 42, in which the spectral imaging camera is configured to identify a circular stapler and an anvil, according to at least one aspect of the present disclosure.

Figure 45:
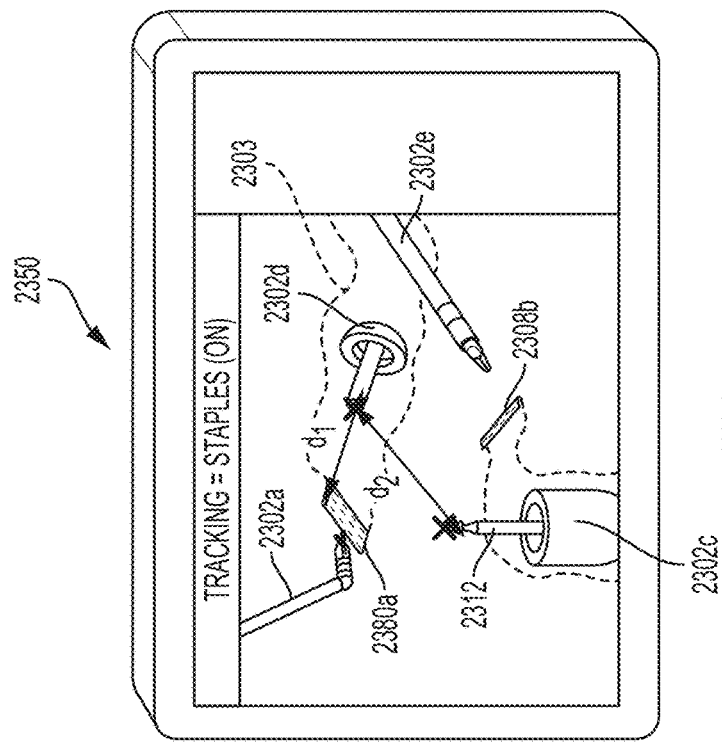

FIG. 45 is a schematic of the screen of FIG. 43, wherein the screen is displaying an augmented view of the surgical site that includes the hidden staples lines, circular stapler, and anvil, and wherein the screen further depicts the distance between the circular stapler and the anvil and the distance between the anvil and one of the staple lines, according to at least one aspect of the present disclosure.

Figure 46:
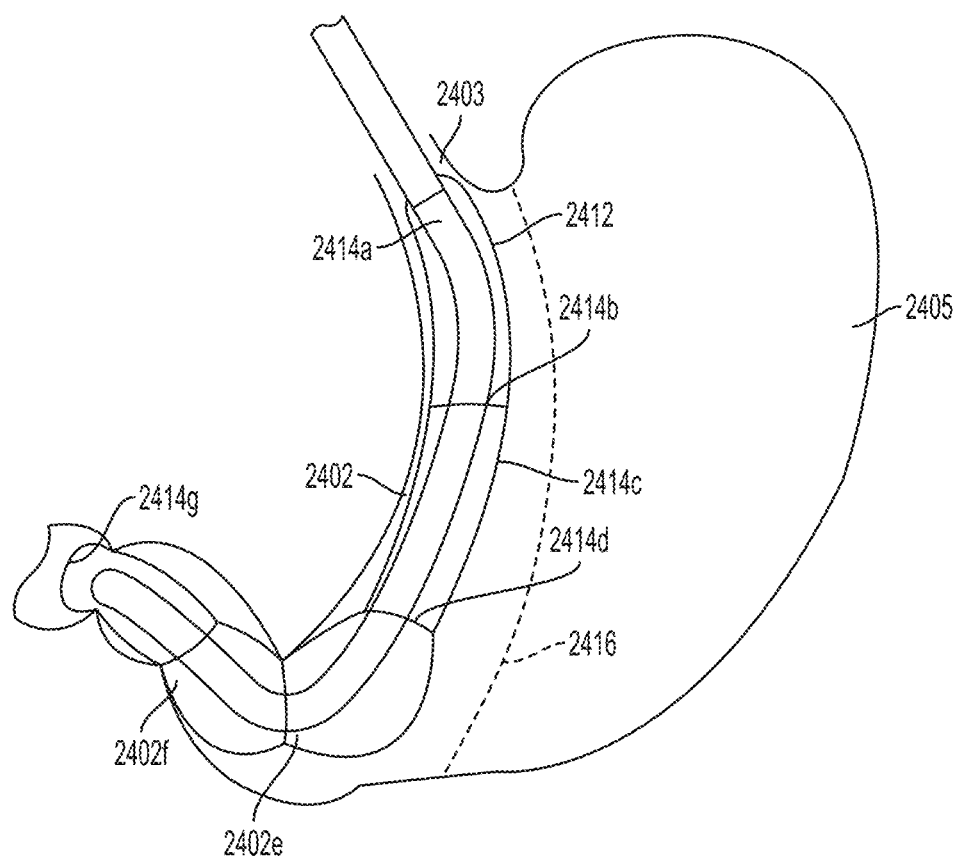

FIG. 46 is a schematic of a stomach with a bougie positioned therein during a sleeve gastrectomy, according to at least one aspect of the present disclosure.

Figure 47:
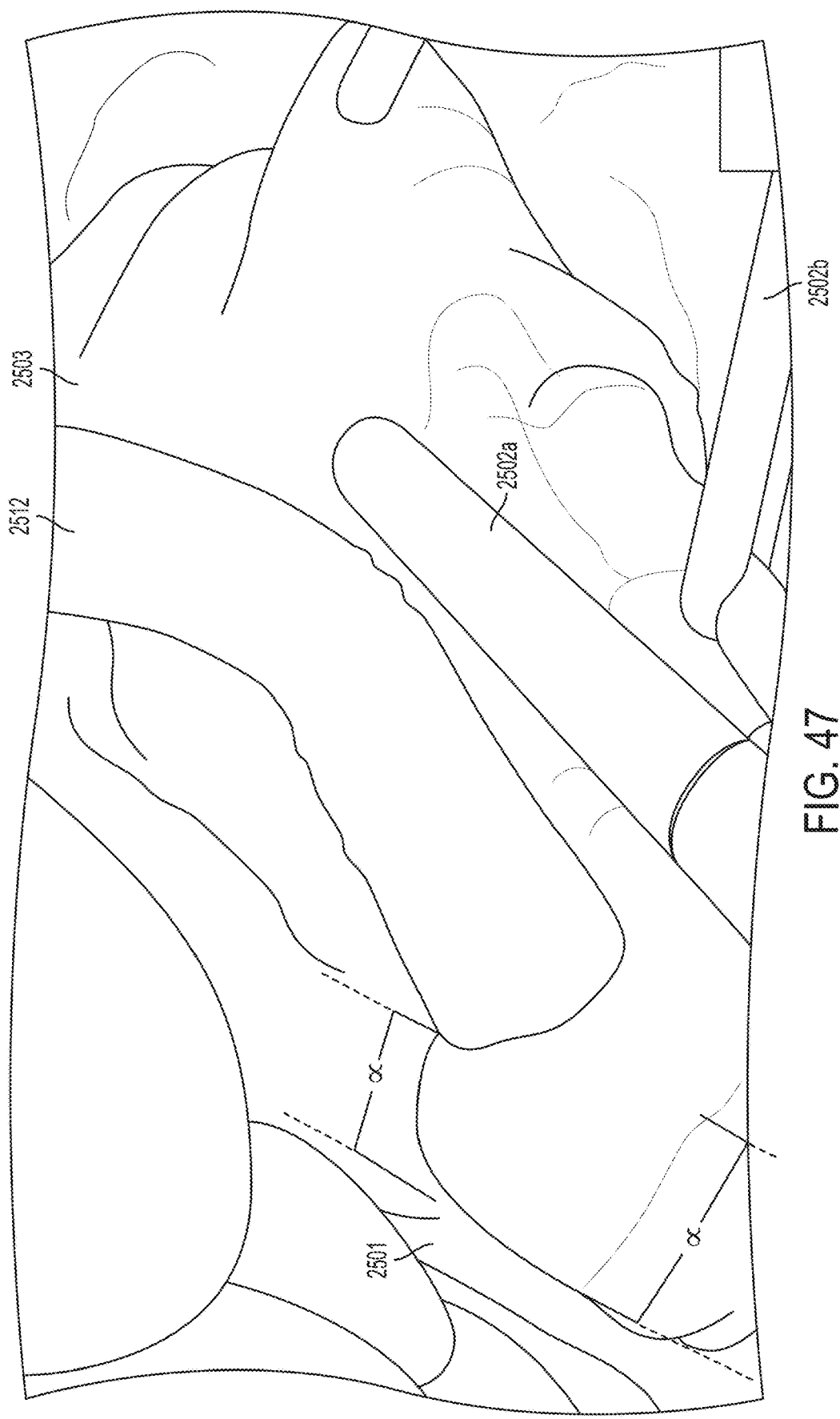

FIG. 47 depicts a stapling step during a sleeve gastrectomy, according to at least one aspect of the present disclosure.

Figure 48:
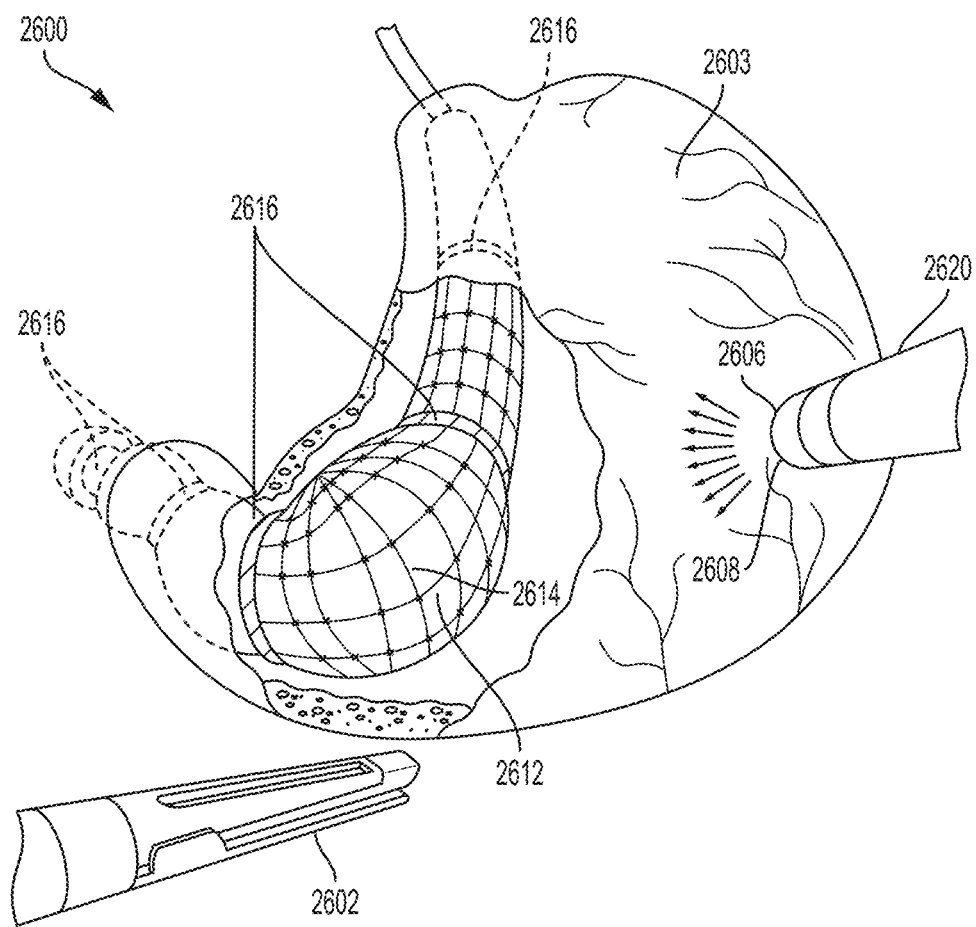

FIG. 48 is a schematic of a surgical visualization system including a spectral imaging camera, in which the spectral imaging camera is viewing a portion of the stomach during a sleeve gastrectomy and a bougie is hidden by the stomach, however, for illustrative purposes, the stomach is partially cutaway to expose the bougie, according to at least one aspect of the present disclosure.

Figure 49:
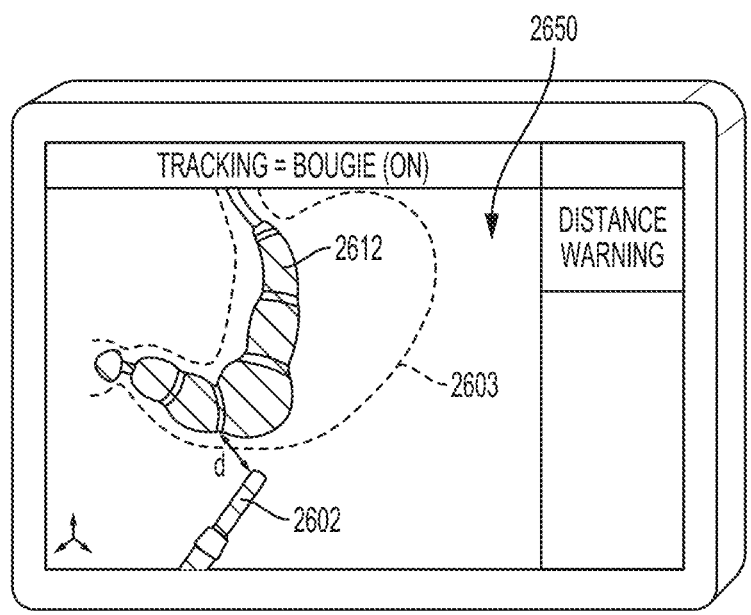

FIG. 49 is a schematic of a screen for the surgical visualization system of FIG. 48, wherein the screen is displaying an augmented view of the surgical site that includes the stomach and the bougie therein, as well as a surgical stapler, and wherein the screen further depicts the distance between the surgical stapler and the bougie, according to at least one aspect of the present disclosure.

Figure 50:
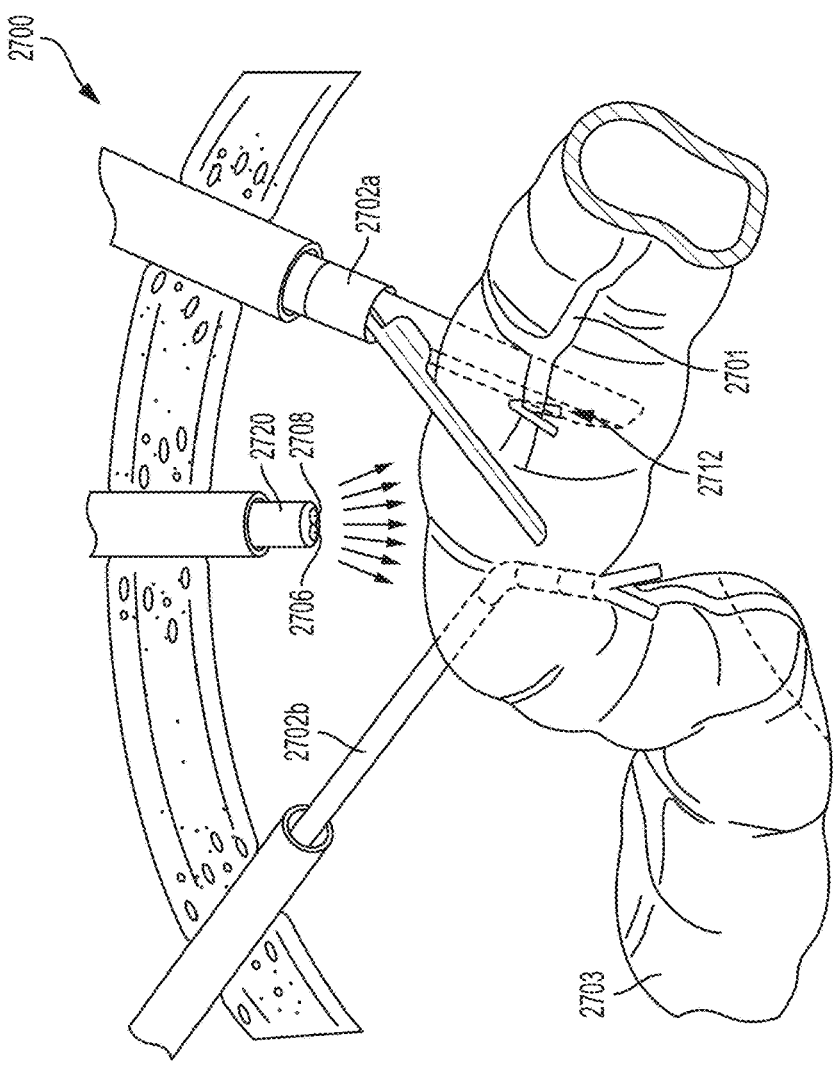

FIG. 50 is a schematic of a surgical visualization system including a spectral imaging camera, in which the spectral imaging camera is configured to identify surgical devices and a clip hidden within tissue, according to at least one aspect of the present disclosure.

Figure 51:
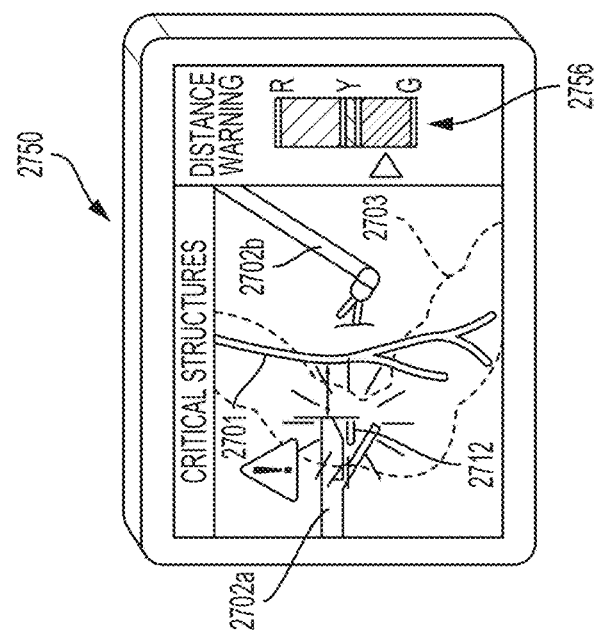

FIG. 51 is a schematic of a screen for the surgical visualization system of FIG. 50, wherein the screen is displaying an augmented view of the surgical site that includes the surgical devices and the clip, wherein the screen further provides a warning based on the relative position of the surgical devices and the clip, according to at least one aspect of the present disclosure.

Figure 52:
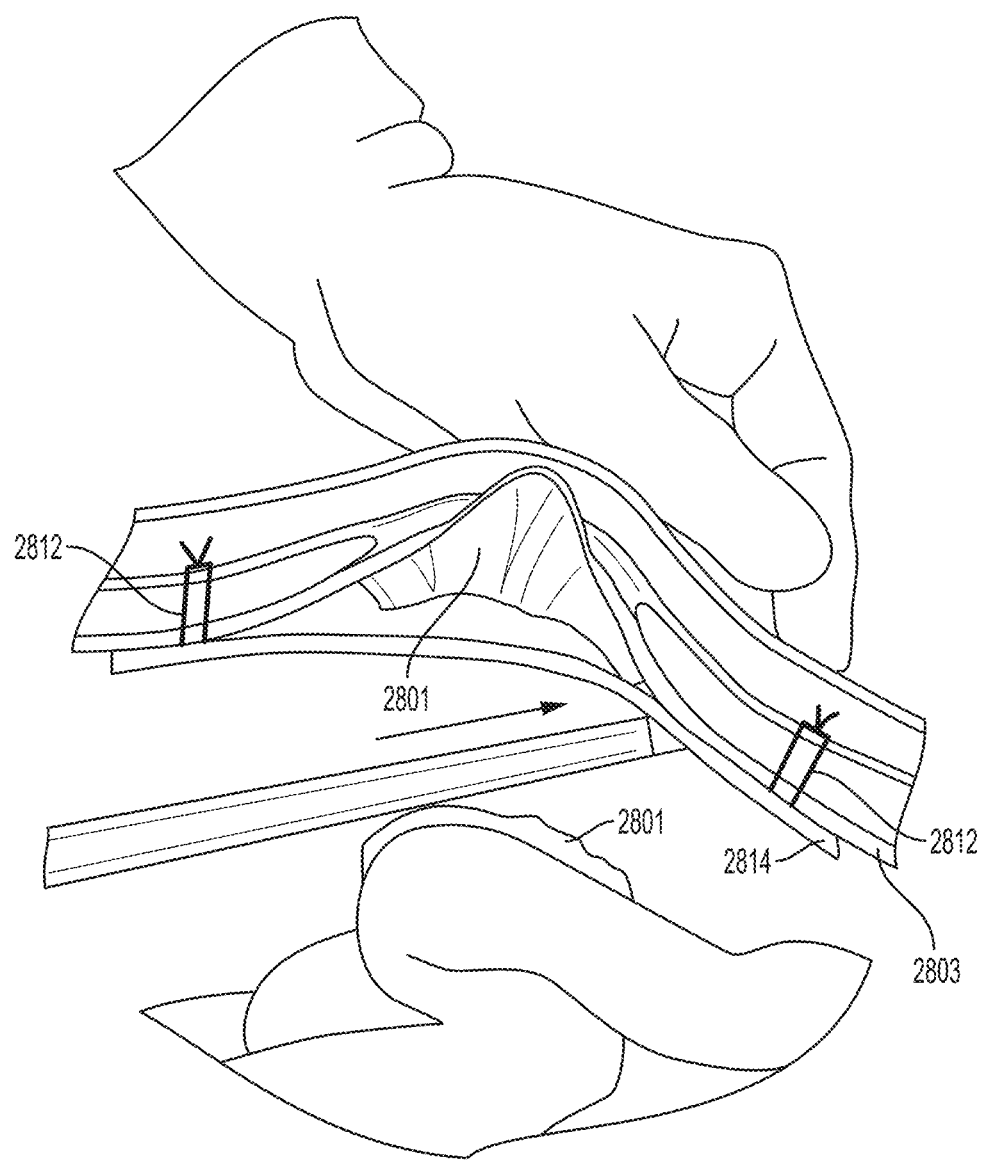

FIG. 52 depicts a step during a hernia repair operation in which clips and a mesh are installed at a surgical site, according to at least one aspect of the present disclosure.

DESCRIPTION

Applicant of the present application also owns the following U.S. Patent applications, filed on Sep. 11, 2018, each of which is herein incorporated by reference in its entirety:

U.S. patent application Ser. No. 16/128,179, titled SURGICAL VISUALIZATION PLATFORM, now U.S. Patent Application Publication No. 2020/0015923;

U.S. patent application Ser. No. 16/128,191, titled SURGICAL VISUALIZATION CONTROLS, now U.S. Patent Application Publication No. 2020/0015904;

U.S. patent application Ser. No. 16/128,180, titled CONTROLLING AN EMITTER ASSEMBLY PULSE SEQUENCE, now U.S. Patent Application Publication No. 2020/0015900;

U.S. patent application Ser. No. 16/128,198, titled SINGULAR EMR SOURCE EMITTER ASSEMBLY, now U.S. Patent Application Publication No. 2020/0015668;

U.S. patent application Ser. No. 16/128,207, titled COMBINATION EMITTER AND CAMERA ASSEMBLY, now U.S. Patent Application Publication No. 2020/0015925;

U.S. patent application Ser. No. 16/128,176, titled SURGICAL VISUALIZATION WITH PROXIMITY TRACKING FEATURES, now U.S. Patent Application Publication No. 2020/0015899;

U.S. patent application Ser. No. 16/128,187, titled SURGICAL VISUALIZATION OF MULTIPLE TARGETS, now U.S. Patent Application Publication No. 2020/0015903;

U.S. patent application Ser. No. 16/128,163, titled OPERATIVE COMMUNICATION OF LIGHT, now U.S. Patent Application Publication No. 2020/0015897;

U.S. patent application Ser. No. 16/128,197, titled ROBOTIC LIGHT PROJECTION TOOLS, now U.S. Patent Application Publication No. 2020/0015924;

U.S. patent application Ser. No. 16/128,164, titled SURGICAL VISUALIZATION FEEDBACK SYSTEM, now U.S. Patent Application Publication No. 2020/0015898;

U.S. patent application Ser. No. 16/128,193, titled SURGICAL VISUALIZATION AND MONITORING, now U.S. Patent Application Publication No. 2020/0015906;

U.S. patent application Ser. No. 16/128,195, titled INTEGRATION OF IMAGING DATA, now U.S. Patent Application Publication No. 2020/0015907;

U.S. patent application Ser. No. 16/128,170, titled ROBOTICALLY-ASSISTED SURGICAL SUTURING SYSTEMS, now U.S. Patent Application Publication No. 2020/0015806;

U.S. patent application Ser. No. 16/128,183, titled SAFETY LOGIC FOR SURGICAL SUTURING SYSTEMS, now U.S. Patent Application Publication No. 2020/0015901;

U.S. patent application Ser. No. 16/128,172, titled ROBOTIC SYSTEMS WITH SEPARATE PHOTOACOUSTIC RECEIVERS, now U.S. Patent Application Publication No. 2020/0015914; and U.S. patent application Ser. No. 16/128,185, titled FORCE SENSOR THROUGH STRUCTURED LIGHT DEFLECTION, now U.S. Patent Application Publication No. 2020/0015902.

Applicant of the present application also owns U.S. Pat. No. 9,072,535, titled SURGICAL STAPLING INSTRUMENTS WITH ROTATABLE STAPLE DEPLOYMENT ARRANGEMENTS, issued Jul. 7, 2015, which is incorporated by reference herein in its entirety.

Applicant of the present application also owns U.S. Provisional Patent Application No. 62/611,339, titled ROBOT ASSISTED SURGICAL PLATFORM, filed Dec. 28, 2017, which is incorporated by reference herein in its entirety.

Applicant of the present application also owns the following U.S. Patent applications, filed on Mar. 29, 2018, each of which is herein incorporated by reference in its entirety:

U.S. patent application Ser. No. 15/940,627, titled DRIVE ARRANGEMENTS FOR ROBOT-ASSISTED SURGICAL PLATFORMS;

U.S. patent application Ser. No. 15/940,676, titled AUTOMATIC TOOL ADJUSTMENTS FOR ROBOT-ASSISTED SURGICAL PLATFORMS;

U.S. patent application Ser. No. 15/940,711, titled SENSING ARRANGEMENTS FOR ROBOT-ASSISTED SURGICAL PLATFORMS; and U.S. patent application Ser. No. 15/940,722, titled CHARACTERIZATION OF TISSUE IRREGULARITIES THROUGH THE USE OF MONO-CHROMATIC LIGHT REFRACTIVITY, filed Mar. 29, 2018, which is incorporated by reference herein in its entirety.

Before explaining various aspects of a surgical visualization platform in detail, it should be noted that the illustrative examples are not limited in application or use to the details of construction and arrangement of parts illustrated in the accompanying drawings and description. The illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects, and/or examples.

The present disclosure is directed to a surgical visualization platform that leverages "digital surgery" to obtain additional information about a patient's anatomy and/or a surgical procedure. The surgical visualization platform is further configured to convey data and/or information to one or more clinicians in a helpful manner. For example, various aspects of the present disclosure provide improved visualization of the patient's anatomy and/or the surgical procedure.

"Digital surgery" can embrace robotic systems, advanced imaging, advanced instrumentation, artificial intelligence, machine learning, data analytics for performance tracking and benchmarking, connectivity both inside and outside of the operating room (OR), and more. Although various surgical visualization platforms described herein can be used in combination with a robotic surgical system, surgical visualization platforms are not limited to use with a robotic surgical system. In certain instances, advanced surgical visualization can occur without robotics and/or with limited and/or optional robotic assistance. Similarly, digital surgery can occur without robotics and/or with limited and/or optional robotic assistance.

In certain instances, a surgical system that incorporates a surgical visualization platform may enable smart dissection in order to identify and avoid critical structures. Critical structures include anatomical structures such as a ureter, an artery such as a superior mesenteric artery, a vein such as a portal vein, a nerve such as a phrenic nerve, and/or a tumor, among other anatomical structures. In other instances, a critical structure can be a foreign structure in the anatomical field, such as a surgical device, surgical fastener, clip, tack, bougie, band, and/or plate, for example. Critical structures can be determined on a patient-by-patient and/or a procedure-by-procedure basis. Example critical structures are further described herein. Smart dissection technology may provide improved intraoperative guidance for dissection and/or can enable smarter decisions with critical anatomy detection and avoidance technology, for example.

A surgical system incorporating a surgical visualization platform may also enable smart anastomosis technologies that provide more consistent anastomoses at optimal location(s) with improved workflow. Cancer localization technologies may also be improved with the various surgical visualization platforms and procedures described herein. For example, cancer localization technologies can identify and track a cancer location, orientation, and its margins. In certain instances, the cancer localizations technologies may compensate for movement of a tool, a patient, and/or the patient's anatomy during a surgical procedure in order to provide guidance back to the point of interest for the clinician.

In certain aspects of the present disclosure, a surgical visualization platform may provide improved tissue characterization and/or lymph node diagnostics and mapping. For example, tissue characterization technologies may characterize tissue type and health without the need for physical haptics, especially when dissecting and/or placing stapling devices within the tissue. Certain tissue characterization technologies described herein may be utilized without ionizing radiation and/or contrast agents. With respect to lymph node diagnostics and mapping, a surgical visualization platform may preoperatively locate, map, and ideally diagnose the lymph system and/or lymph nodes involved in cancerous diagnosis and staging, for example.

These and other related topics are described herein and/or in the aforementioned contemporaneously-filed U.S. Patent applications, which are incorporated by reference herein in their respective entireties.

During a surgical procedure, the information available to the clinician via the "naked eye" and/or an imaging system may provide an incomplete view of the surgical site. For example, certain structures, such as structures embedded or buried within an organ, can be at least partially concealed or hidden from view. Additionally, certain dimensions and/or relative distances can be difficult to ascertain with existing sensor systems and/or difficult for the "naked eye" to perceive. Moreover, certain structures can move preoperatively (e.g. before a surgical procedure but after a preoperative scan) and/or intraoperatively. In such instances, the clinician can be unable to accurately determine the location of a critical structure intraoperatively.

When the position of a critical structure is uncertain and/or when the proximity between the critical structure and a surgical tool is unknown, a clinician's decision-making process can be inhibited. For example, a clinician may avoid certain areas in order to avoid inadvertent dissection of a critical structure; however, the avoided area may be unnecessarily large and/or at least partially misplaced. Due to uncertainty and/or overly/excessive exercises in caution, the clinician may not access certain desired regions. For example, excess caution may cause a clinician to leave a portion of a tumor and/or other undesirable tissue in an effort to avoid a critical structure even if the critical structure is not in the particular area and/or would not be negatively impacted by the clinician working in that particular area. In certain instances, surgical results can be improved with increased knowledge and/or certainty, which can allow a surgeon to be more accurate and, in certain instances, less conservative/more aggressive with respect to particular anatomical areas.

In various aspects, the present disclosure provides a surgical visualization system for intraoperative identification and avoidance of critical structures. In one aspect, the present disclosure provides a surgical visualization system that enables enhanced intraoperative decision making and improved surgical outcomes. In various aspects, the disclosed surgical visualization system provides advanced visualization capabilities beyond what a clinician sees with the "naked eye" and/or beyond what an imaging system can recognize and/or convey to the clinician. The various surgical visualization systems can augment and enhance what a clinician is able to know prior to tissue treatment (e.g. dissection) and, thus, may improve outcomes in various instances.

For example, a visualization system can include a first light emitter configured to emit a plurality of spectral waves, a second light emitter configured to emit a light pattern, and one or more receivers, or sensors, configured to detect visible light, molecular responses to the spectral waves (spectral imaging), and/or the light pattern. The surgical visualization system can also include an imaging system and a control circuit in signal communication with the receiver(s) and the imaging system. Based on output from the receiver(s), the control circuit can determine a geometric surface map, i.e. three-dimensional surface topography, of the visible surfaces at the surgical site and one or more distances with respect to the surgical site. In certain instances, the control circuit can determine one more distances to an at least partially concealed structure. Moreover, the imaging system can convey the geometric surface map and the one or more distances to a clinician. In such instances, an augmented view of the surgical site provided to the clinician can provide a representation of the concealed structure within the relevant context of the surgical site. For example, the imaging system can virtually augment the concealed structure on the geometric surface map of the concealing and/or obstructing tissue similar to a line drawn on the ground to indicate a utility line below the surface. Additionally or alternatively, the imaging system can convey the proximity of one or more surgical tools to the visible and obstructing tissue and/or to the at least partially concealed structure and/or the depth of the concealed structure below the visible surface of the obstructing tissue. For example, the visualization system can determine a distance with respect to the augmented line on the surface of the visible tissue and convey the distance to the imaging system.

In various aspects of the present disclosure, a surgical visualization system is disclosed for intraoperative identification and avoidance of critical structures. Such a surgical visualization system can provide valuable information to a clinician during a surgical procedure. As a result, the clinician can confidently maintain momentum throughout the surgical procedure knowing that the surgical visualization system is tracking a critical structure such as a ureter, specific nerves, and/or critical blood vessels, for example, which may be approached during dissection, for example. In one aspect, the surgical visualization system can provide an indication to the clinician in sufficient time for the clinician to pause and/or slow down the surgical procedure and evaluate the proximity to the critical structure to prevent inadvertent damage thereto. The surgical visualization system can provide an ideal, optimized, and/or customizable amount of information to the clinician to allow the clinician to move confidently and/or quickly through tissue while avoiding inadvertent damage to healthy tissue and/or critical structure(s) and, thus, to minimize the risk of harm resulting from the surgical procedure.

Figure 1:
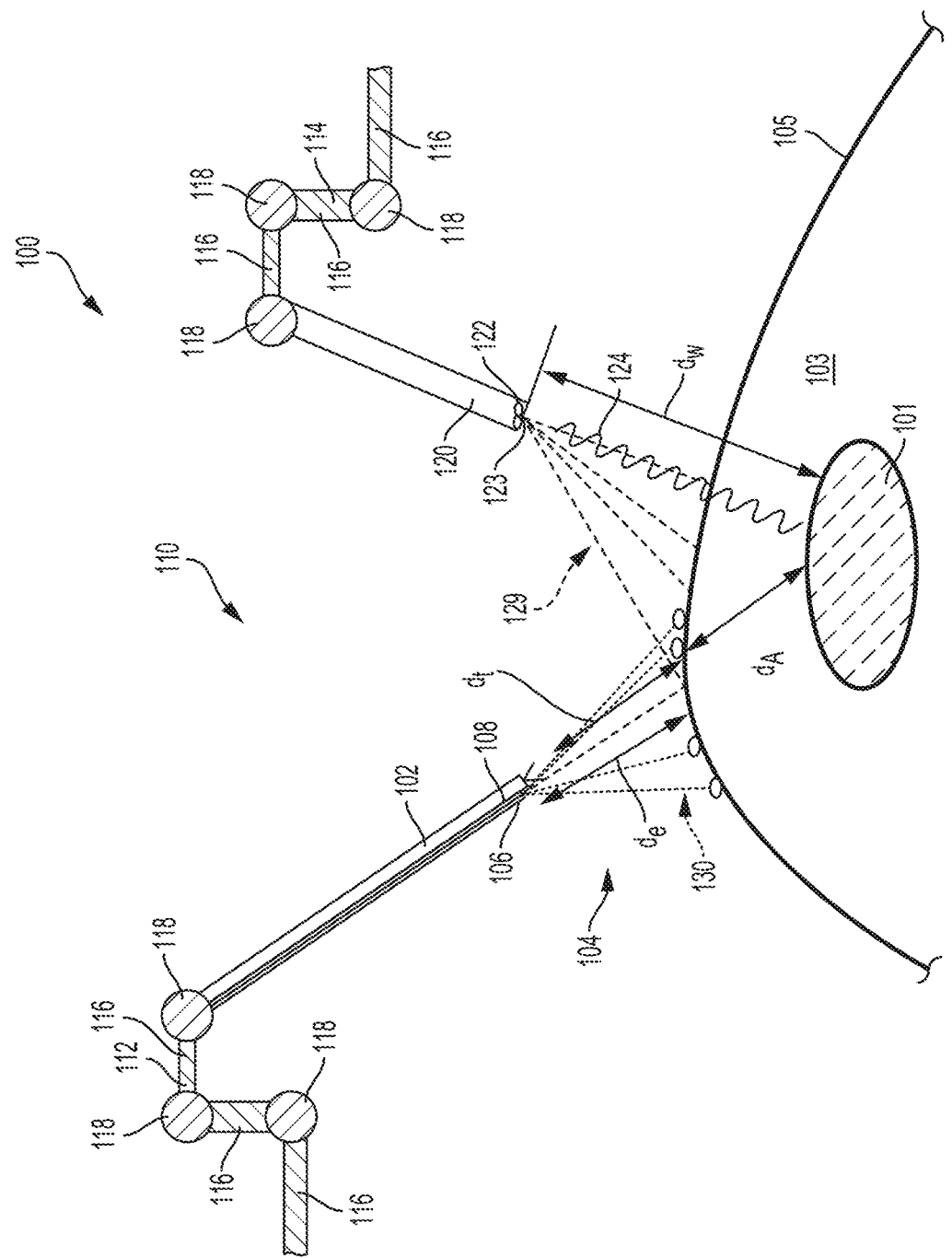
FIG. 1 is a schematic of a surgical visualization system including an imaging device and a surgical device, the surgical visualization system configured to identify a critical structure below a tissue surface, according to at least one aspect of the present disclosure.

FIG. 1 is a schematic of a surgical visualization system 100 according to at least one aspect of the present disclosure. The surgical visualization system 100 can create a visual representation of a critical structure 101 within an anatomical field. The surgical visualization system 100 can be used for clinical analysis and/or medical intervention, for example. In certain instances, the surgical visualization system 100 can be used intraoperatively to provide real-time, or near real-time, information to the clinician regarding proximity data, dimensions, and/or distances during a surgical procedure. The surgical visualization system 100 is configured for intraoperative identification of critical structure(s) and/or to facilitate the avoidance of the critical structure(s) 101 by a surgical device. For example, by identifying the critical structure 101, a clinician can avoid maneuvering a surgical device around the critical structure 101 and/or a region in a predefined proximity of the critical structure 101 during a surgical procedure. The clinician can avoid dissection of and/or near a vein, artery, nerve, and/or vessel, for example, identified as the critical structure 101, for example. In various instances, the critical structure 101 can be determined on a patient-by-patient and/or a procedure-by-procedure basis.

The surgical visualization system 100 incorporates tissue identification and geometric surface mapping in combination with a distance sensor system 104. In combination, these features of the surgical visualization system 100 can determine a position of a critical structure 101 within the anatomical field and/or the proximity of a surgical device 102 to the surface 105 of the visible tissue and/or to the critical structure 101. Moreover, the surgical visualization system 100 includes an imaging system that includes an imaging device 120, such as a camera, for example, configured to provide real-time views of the surgical site. In various instances, the imaging device 120 is a spectral camera (e.g. a hyperspectral camera, multispectral camera, or selective spectral camera), which is configured to detect reflected spectral waveforms and generate a spectral cube of images based on the molecular response to the different wavelengths. Views from the imaging device 120 can be provided to a clinician and, in various aspects of the present disclosure, can be augmented with additional information based on the tissue identification, landscape mapping, and the distance sensor system 104. In such instances, the surgical visualization system 100 includes a plurality of subsystems—an imaging subsystem, a surface mapping subsystem, a tissue identification subsystem, and/or a distance determining subsystem. These subsystems can cooperate to intraoperatively provide advanced data synthesis and integrated information to the clinician(s).

The imaging device can include a camera or imaging sensor that is configured to detect visible light, spectral light waves (visible or invisible), and a structured light pattern (visible or invisible), for example. In various aspects of the present disclosure, the imaging system can include an imaging device such as an endoscope, for example. Additionally or alternatively, the imaging system can include an imaging device such as an arthroscope, angioscope, bronchoscope, choledochoscope, colonoscope, cytoscope, duodenoscope, enteroscope, esophagogastro-duodenoscope (gastroscope), laryngoscope, nasopharyngo-neproscope, sigmoidoscope, thoracoscope, ureteroscope, or exoscope, for example. In other instances, such as in open surgery applications, the imaging system may not include a scope.

In various aspects of the present disclosure, the tissue identification subsystem can be achieved with a spectral imaging system. The spectral imaging system can rely on hyperspectral imaging, multispectral imaging, or selective spectral imaging, for example. Hyperspectral imaging of tissue is further described in U.S. Pat. No. 9,274,047, titled SYSTEM AND METHOD FOR GROSS ANATOMIC PATHOLOGY USING HYPERSPECTRAL IMAGING, issued Mar. 1, 2016, which is incorporated by reference herein in its entirety.

In various aspect of the present disclosure, the surface mapping subsystem can be achieved with a light pattern system, as further described herein. The use of a light pattern (or structured light) for surface mapping is known. Known surface mapping techniques can be utilized in the surgical visualization systems described herein.

Structured light is the process of projecting a known pattern (often a grid or horizontal bars) on to a surface. U.S. Patent Application Publication No. 2017/0055819, titled SET COMPRISING A SURGICAL INSTRUMENT, published Mar. 2, 2017, and U.S. Patent Application Publication No. 2017/0251900, titled DEPICTION SYSTEM, published Sep. 7, 2017, disclose a surgical system comprising a light source and a projector for projecting a light pattern. U.S. Patent Application Publication No. 2017/0055819, titled SET COMPRISING A SURGICAL INSTRUMENT, published Mar. 2, 2017, and U.S. Patent Application Publication No. 2017/0251900, titled DEPICTION SYSTEM, published Sep. 7, 2017, are incorporated by reference herein in their respective entireties.

In various aspects of the present disclosure, the distance determining system can be incorporated into the surface mapping system. For example, structured light can be utilized to generate a three-dimensional virtual model of the visible surface and determine various distances with respect to the visible surface. Additionally or alternatively, the distance determining system can rely on time-of-flight measurements to determine one or more distances to the identified tissue (or other structures) at the surgical site.

Figure 2:
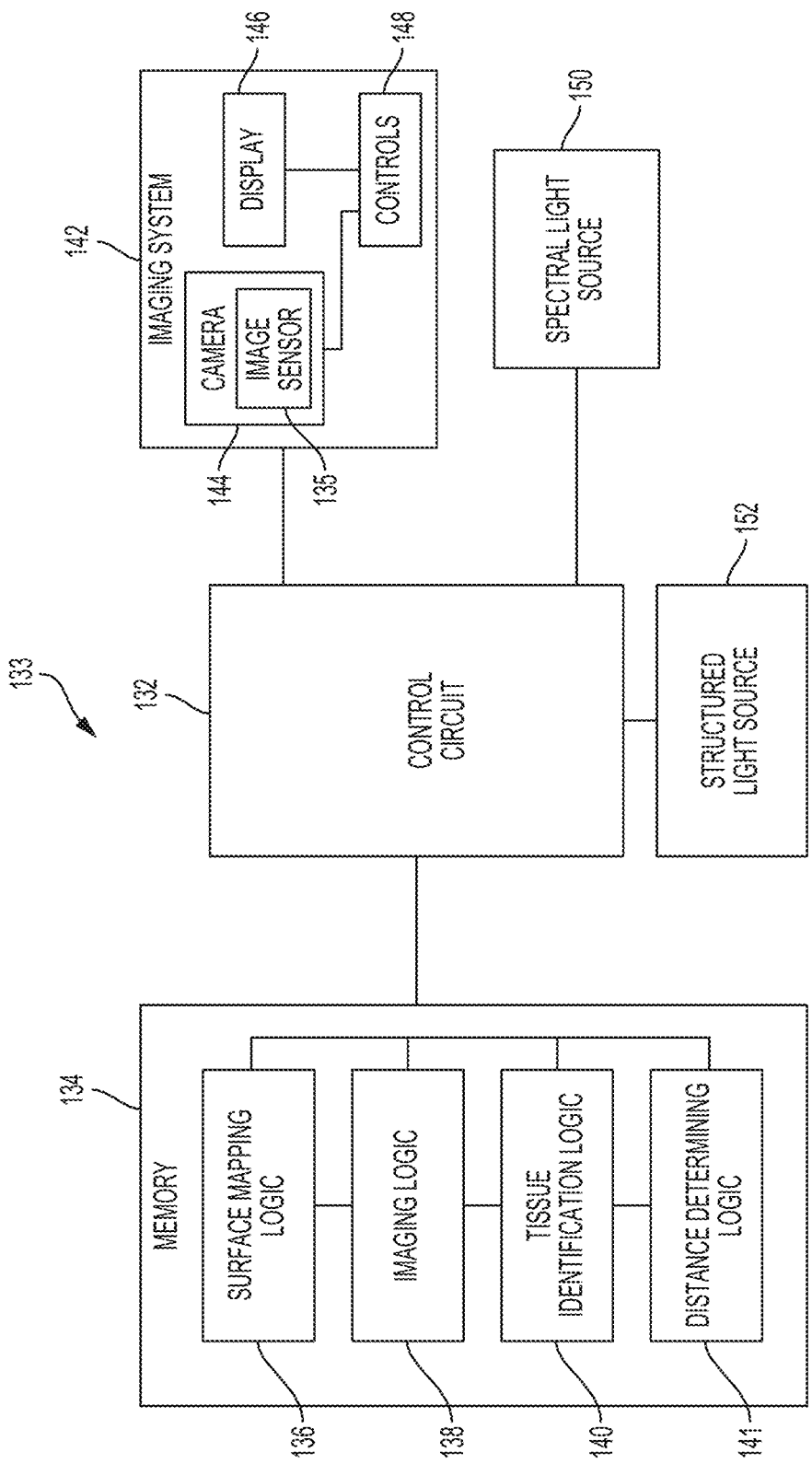
FIG. 2 is a schematic of a control system for a surgical visualization system, according to at least one aspect of the present disclosure.

FIG. 2 is a schematic diagram of a control system 133, which can be utilized with the surgical visualization system 100. The control system 133 includes a control circuit 132 in signal communication with a memory 134. The memory 134 stores instructions executable by the control circuit 132 to determine and/or recognize critical structures (e.g. the critical structure 101 in FIG. 1), determine and/or compute one or more distances and/or three-dimensional digital representations, and to communicate certain information to one or more clinicians. For example, the memory 134 stores surface mapping logic 136, imaging logic 138, tissue identification logic 140, or distance determining logic 141 or any combinations of the logic 136, 138, 140, and 141. The control system 133 also includes an imaging system 142 having one or more cameras 144 (like the imaging device 120 in FIG. 1), one or more displays 146, or one or more controls 148 or any combinations of these elements. The camera 144 can include one or more image sensors 135 to receive signals from various light sources emitting light at various visible and invisible spectra (e.g. visible light, spectral imagers, three-dimensional lens, among others). The display 146 can include one or more screens or monitors for depicting real, virtual, and/or virtually-augmented images and/or information to one or more clinicians.

In various aspects, the heart of the camera 144 is the image sensor 135. Generally, modern image sensors 135 are solid-state electronic devices containing up to millions of discrete photodetector sites called pixels. The image sensor 135 technology falls into one of two categories: Charge-Coupled Device (CCD) and Complementary Metal Oxide Semiconductor (CMOS) imagers and more recently, short-wave infrared (SWIR) is an emerging technology in imaging. Another type of image sensor 135 employs a hybrid CCD/CMOS architecture (sold under the name "sCMOS") and consists of CMOS readout integrated circuits (ROICs) that are bump bonded to a CCD imaging substrate. CCD and CMOS image sensors 135 are sensitive to wavelengths from approximately 350-1050 nm, although the range is usually given from 400-1000 nm. CMOS sensors are, in general, more sensitive to IR wavelengths than CCD sensors. Solid state image sensors 135 are based on the photoelectric effect and, as a result, cannot distinguish between colors. Accordingly, there are two types of color CCD cameras: single chip and three-chip. Single chip color CCD cameras offer a common, low-cost imaging solution and use a mosaic (e.g. Bayer) optical filter to separate incoming light into a series of colors and employ an interpolation algorithm to resolve full color images. Each color is, then, directed to a different set of pixels. Three-chip color CCD cameras provide higher resolution by employing a prism to direct each section of the incident spectrum to a different chip. More accurate color reproduction is possible, as each point in space of the object has separate RGB intensity values, rather than using an algorithm to determine the color. Three-chip cameras offer extremely high resolutions.

The control system 133 also includes a spectral light source 150 and a structured light source 152. In certain instances, a single source can be pulsed to emit wavelengths of light in the spectral light source 150 range and wavelengths of light in the structured light source 152 range. Alternatively, a single light source can be pulsed to provide light in the invisible spectrum (e.g. infrared spectral light) and wavelengths of light on the visible spectrum. The spectral light source 150 can be a hyperspectral light source, a multispectral light source, and/or a selective spectral light source, for example. In various instances, the tissue identification logic 140 can identify critical structure(s) via data from the spectral light source 150 received by the image sensor 135 portion of the camera 144. The surface mapping logic 136 can determine the surface contours of the visible tissue based on reflected structured light. With time-of-flight measurements, the distance determining logic 141 can determine one or more distance(s) to the visible tissue and/or the critical structure 101. One or more outputs from the surface mapping logic 136, the tissue identification logic 140, and the distance determining logic 141, can be provided to the imaging logic 138, and combined, blended, and/or overlaid to be conveyed to a clinician via the display 146 of the imaging system 142.

Figure 2A:
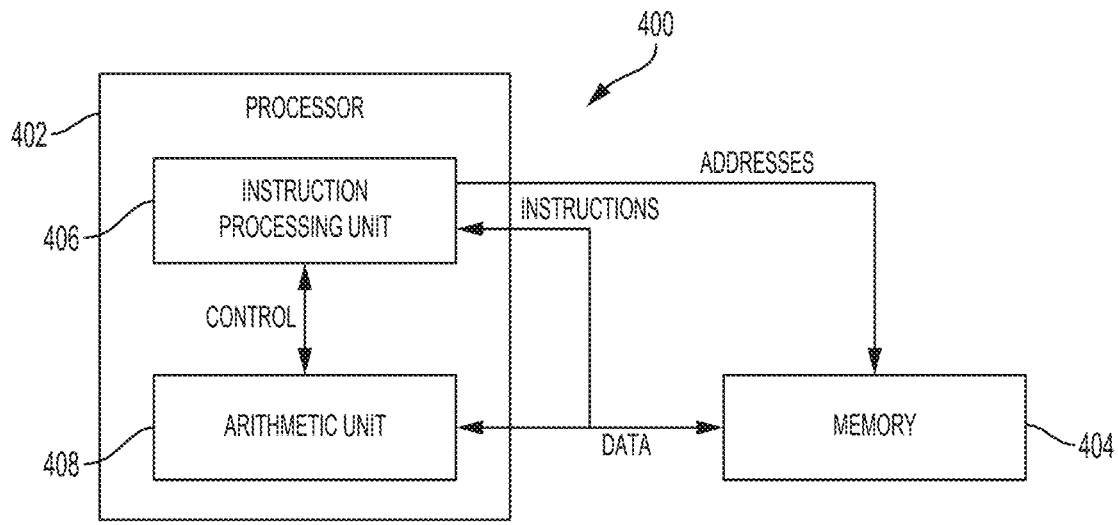
FIG. 2A illustrates a control circuit configured to control aspects of a surgical visualization system, according to at least one aspect of the present disclosure.
Figure 2B:
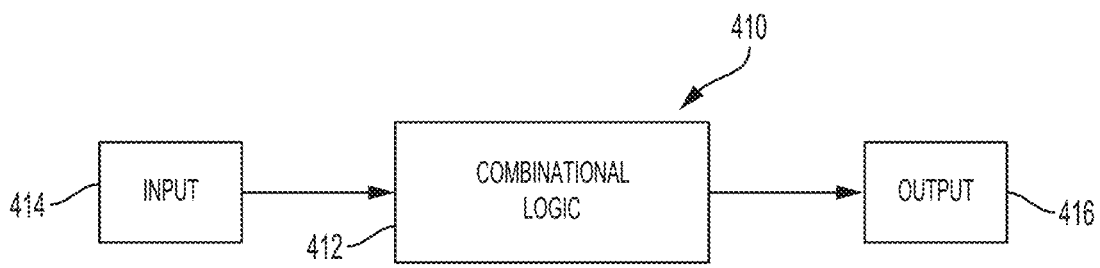
FIG. 2B illustrates a combinational logic circuit configured to control aspects of a surgical visualization system, according to at least one aspect of the present disclosure.
Figure 2C:
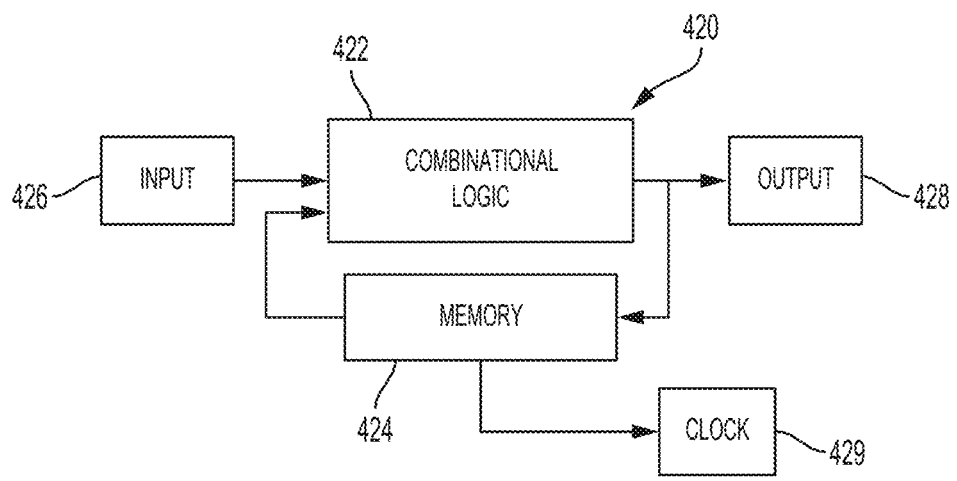
FIG. 2C illustrates a sequential logic circuit configured to control aspects of a surgical visualization system, according to at least one aspect of the present disclosure.

The description now turns briefly to FIGS. 2A-2C to describe various aspects of the control circuit 132 for controlling various aspects of the surgical visualization system 100. Turning to FIG. 2A, there is illustrated a control circuit 400 configured to control aspects of the surgical visualization system 100, according to at least one aspect of this disclosure. The control circuit 400 can be configured to implement various processes described herein. The control circuit 400 may comprise a microcontroller comprising one or more processors 402 (e.g., microprocessor, microcontroller) coupled to at least one memory circuit 404. The memory circuit 404 stores machine-executable instructions that, when executed by the processor 402, cause the processor 402 to execute machine instructions to implement various processes described herein. The processor 402 may be any one of a number of single-core or multicore processors known in the art. The memory circuit 404 may comprise volatile and non-volatile storage media. The processor 402 may include an instruction processing unit 406 and an arithmetic unit 408. The instruction processing unit may be configured to receive instructions from the memory circuit 404 of this disclosure.

FIG. 2B illustrates a combinational logic circuit 410 configured to control aspects of the surgical visualization system 100, according to at least one aspect of this disclosure. The combinational logic circuit 410 can be configured to implement various processes described herein. The combinational logic circuit 410 may comprise a finite state machine comprising a combinational logic 412 configured to receive data associated with the surgical instrument or tool at an input 414, process the data by the combinational logic 412, and provide an output 416.

FIG. 2C illustrates a sequential logic circuit 420 configured to control aspects of the surgical visualization system 100, according to at least one aspect of this disclosure. The sequential logic circuit 420 or the combinational logic 422 can be configured to implement various processes described herein. The sequential logic circuit 420 may comprise a finite state machine. The sequential logic circuit 420 may comprise a combinational logic 422, at least one memory circuit 424, and a clock 429, for example. The at least one memory circuit 424 can store a current state of the finite state machine. In certain instances, the sequential logic circuit 420 may be synchronous or asynchronous. The combinational logic 422 is configured to receive data associated with a surgical device or system from an input 426, process the data by the combinational logic 422, and provide an output 428. In other aspects, the circuit may comprise a combination of a processor (e.g., processor 402 in FIG. 2A) and a finite state machine to implement various processes herein. In other aspects, the finite state machine may comprise a combination of a combinational logic circuit (e.g., combinational logic circuit 410, FIG. 2B) and the sequential logic circuit 420.

Referring again to the surgical visualization system 100 in FIG. 1, the critical structure 101 can be an anatomical structure of interest. For example, the critical structure 101 can be a ureter, an artery such as a superior mesenteric artery, a vein such as a portal vein, a nerve such as a phrenic nerve, and/or a tumor, among other anatomical structures. In other instances, the critical structure 101 can be a foreign structure in the anatomical field, such as a surgical device, surgical fastener, clip, tack, bougie, band, and/or plate, for example. Example critical structures are further described herein and in the aforementioned contemporaneously-filed U.S. Patent applications, which are incorporated by reference herein in their respective entireties.

In one aspect, the critical structure 101 may be embedded in tissue 103. Stated differently, the critical structure 101 may be positioned below the surface 105 of the tissue 103. In such instances, the tissue 103 conceals the critical structure 101 from the clinician's view. The critical structure 101 is also obscured from the view of the imaging device 120 by the tissue 103. The tissue 103 can be fat, connective tissue, adhesions, and/or organs, for example. In other instances, the critical structure 101 can be partially obscured from view.

FIG. 1 also depicts the surgical device 102. The surgical device 102 includes an end effector having opposing jaws extending from the distal end of the shaft of the surgical device 102. The surgical device 102 can be any suitable surgical device such as, for example, a dissector, a stapler, a grasper, a clip applier, and/or an energy device including mono-polar probes, bi-polar probes, ablation probes, and/or an ultrasonic end effector. Additionally or alternatively, the surgical device 102 can include another imaging or diagnostic modality, such as an ultrasound device, for example. In one aspect of the present disclosure, the surgical visualization system 100 can be configured to achieve identification of one or more critical structures 101 and the proximity of the surgical device 102 to the critical structure(s) 101.

The imaging device 120 of the surgical visualization system 100 is configured to detect light at various wavelengths, such as, for example, visible light, spectral light waves (visible or invisible), and a structured light pattern (visible or invisible). The imaging device 120 may include a plurality of lenses, sensors, and/or receivers for detecting the different signals. For example, the imaging device 120 can be a hyperspectral, multispectral, or selective spectral camera, as further described herein. The imaging device 120 can also include a waveform sensor 122 (such as a spectral image sensor, detector, and/or three-dimensional camera lens). For example, the imaging device 120 can include a right-side lens and a left-side lens used together to record two two-dimensional images at the same time and, thus, generate a three-dimensional image of the surgical site, render a three-dimensional image of the surgical site, and/or determine one or more distances at the surgical site. Additionally or alternatively, the imaging device 120 can be configured to receive images indicative of the topography of the visible tissue and the identification and position of hidden critical structures, as further described herein. For example, the field of view of the imaging device 120 can overlap with a pattern of light (structured light) on the surface 105 of the tissue, as shown in FIG. 1.

In one aspect, the surgical visualization system 100 may be incorporated into a robotic system 110. For example, the robotic system 110 may include a first robotic arm 112 and a second robotic arm 114. The robotic arms 112, 114 include rigid structural members 116 and joints 118, which can include servomotor controls. The first robotic arm 112 is configured to maneuver the surgical device 102, and the second robotic arm 114 is configured to maneuver the imaging device 120. A robotic control unit can be configured to issue control motions to the robotic arms 112, 114, which can affect the surgical device 102 and the imaging device 120, for example.

The surgical visualization system 100 also includes an emitter 106, which is configured to emit a pattern of light, such as stripes, grid lines, and/or dots, to enable the determination of the topography or landscape of the surface 105. For example, projected light arrays 130 can be used for three-dimensional scanning and registration on the surface 105. The projected light arrays 130 can be emitted from the emitter 106 located on the surgical device 102 and/or one of the robotic arms 112, 114 and/or the imaging device 120, for example. In one aspect, the projected light array 130 is employed to determine the shape defined by the surface 105 of the tissue 103 and/or the motion of the surface 105 intraoperatively. The imaging device 120 is configured to detect the projected light arrays 130 reflected from the surface 105 to determine the topography of the surface 105 and various distances with respect to the surface 105.

In one aspect, the imaging device 120 also may include an optical waveform emitter 123 that is configured to emit electromagnetic radiation 124 (NIR photons) that can penetrate the surface 105 of the tissue 103 and reach the critical structure 101. The imaging device 120 and the optical waveform emitter 123 thereon can be positionable by the robotic arm 114. A corresponding waveform sensor 122 (an image sensor, spectrometer, or vibrational sensor, for example) on the imaging device 120 is configured to detect the effect of the electromagnetic radiation received by the waveform sensor 122. The wavelengths of the electromagnetic radiation 124 emitted by the optical waveform emitter 123 can be configured to enable the identification of the type of anatomical and/or physical structure, such as the critical structure 101. The identification of the critical structure 101 can be accomplished through spectral analysis, photo-acoustics, and/or ultrasound, for example. In one aspect, the wavelengths of the electromagnetic radiation 124 may be variable. The waveform sensor 122 and optical waveform emitter 123 may be inclusive of a multispectral imaging system and/or a selective spectral imaging system, for example. In other instances, the waveform sensor 122 and optical waveform emitter 123 may be inclusive of a photoacoustic imaging system, for example. In other instances, the optical waveform emitter 123 can be positioned on a separate surgical device from the imaging device 120.

The surgical visualization system 100 also may include the distance sensor system 104 configured to determine one or more distances at the surgical site. In one aspect, the time-of-flight distance sensor system 104 may be a time-of-flight distance sensor system that includes an emitter, such as the emitter 106, and a receiver 108, which can be positioned on the surgical device 102. In other instances, the time-of-flight emitter can be separate from the structured light emitter. In one general aspect, the emitter 106 portion of the time-of-flight distance sensor system 104 may include a very tiny laser source and the receiver 108 portion of the time-of-flight distance sensor system 104 may include a matching sensor. The time-of-flight distance sensor system 104 can detect the "time of flight," or how long the laser light emitted by the emitter 106 has taken to bounce back to the sensor portion of the receiver 108. Use of a very narrow light source in the emitter 106 enables the distance sensor system 104 to determining the distance to the surface 105 of the tissue 103 directly in front of the distance sensor system 104. Referring still to FIG. 1, $d_e$ is the emitter-to-tissue distance from the emitter 106 to the surface 105 of the tissue 103 and $d_t$ is the device-to-tissue distance from the distal end of the surgical device 102 to the surface 105 of the tissue. The distance sensor system 104 can be employed to determine the emitter-to-tissue distance $d_e$. The device-to-tissue distance $d_t$ is obtainable from the known position of the emitter 106 on the shaft of the surgical device 102 relative to the distal end of the surgical device 102. In other words, when the distance between the emitter 106 and the distal end of the surgical device 102 is known, the device-to-tissue distance $d_t$ can be determined from the emitter-to-tissue distance $d_e$. In certain instances, the shaft of the surgical device 102 can include one or more articulation joints, and can be articulatable with respect to the emitter 106 and the jaws. The articulation configuration can include a multi-joint vertebrae-like structure, for example. In certain instances, a three-dimensional camera can be utilized to triangulate one or more distances to the surface 105.

In various instances, the receiver 108 for the time-of-flight distance sensor system 104 can be mounted on a separate surgical device instead of the surgical device 102. For example, the receiver 108 can be mounted on a cannula or trocar through which the surgical device 102 extends to reach the surgical site. In still other instances, the receiver 108 for the time-of-flight distance sensor system 104 can be mounted on a separate robotically-controlled arm (e.g. the robotic arm 114), on a movable arm that is operated by another robot, and/or to an operating room (OR) table or fixture. In certain instances, the imaging device 120 includes the time-of-flight receiver 108 to determine the distance from the emitter 106 to the surface 105 of the tissue 103 using a line between the emitter 106 on the surgical device 102 and the imaging device 120. For example, the distance $d_e$ can be triangulated based on known positions of the emitter 106 (on the surgical device 102) and the receiver 108 (on the imaging device 120) of the time-of-flight distance sensor system 104. The three-dimensional position of the receiver 108 can be known and/or registered to the robot coordinate plane intraoperatively.

In certain instances, the position of the emitter 106 of the time-of-flight distance sensor system 104 can be controlled by the first robotic arm 112 and the position of the receiver 108 of the time-of-flight distance sensor system 104 can be controlled by the second robotic arm 114. In other instances, the surgical visualization system 100 can be utilized apart from a robotic system. In such instances, the distance sensor system 104 can be independent of the robotic system.

In certain instances, one or more of the robotic arms 112, 114 may be separate from a main robotic system used in the surgical procedure. At least one of the robotic arms 112, 114 can be positioned and registered to a particular coordinate system without a servomotor control. For example, a closedloop control system and/or a plurality of sensors for the robotic arms 110 can control and/or register the position of the robotic arm(s) 112, 114 relative to the particular coordinate system. Similarly, the position of the surgical device 102 and the imaging device 120 can be registered relative to a particular coordinate system.

Figure 3:
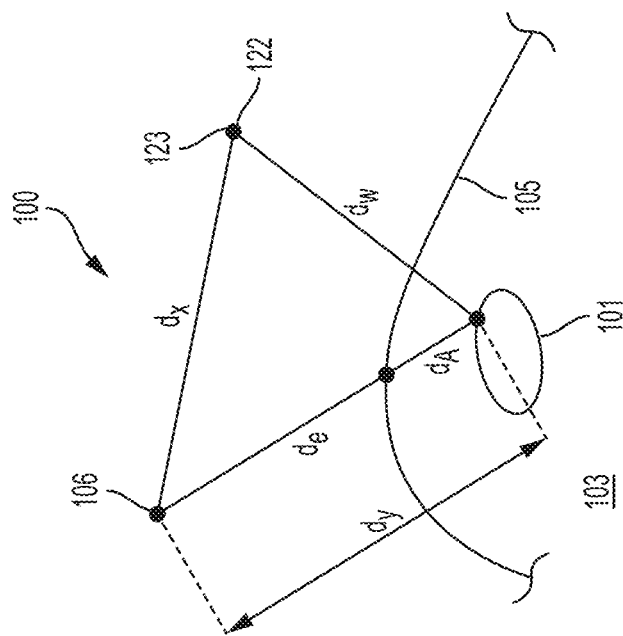
FIG. 3 is a schematic depicting triangularization between the surgical device, the imaging device, and the critical structure of FIG. 1 to determine a depth $d_A$ of the critical structure below the tissue surface, according to at least one aspect of the present disclosure.

Referring still to FIG. 1, $d_w$ is the camera-to-critical structure distance from the optical waveform emitter 123 located on the imaging device 120 to the surface of the critical structure 101, and $d_A$ is the depth of the critical structure 101 below the surface 105 of the tissue 103 (i.e., the distance between the portion of the surface 105 closest to the surgical device 102 and the critical structure 101). In various aspects, the time-of-flight of the optical waveforms emitted from the optical waveform emitter 123 located on the imaging device 120 can be configured to determine the camera-to-critical structure distance $d_w$. The use of spectral imaging in combination with time-of-flight sensors is further described herein. Moreover, referring now to FIG. 3, in various aspects of the present disclosure, the depth $d_A$ of the critical structure 101 relative to the surface 105 of the tissue 103 can be determined by triangulating from the distance $d_w$ and known positions of the emitter 106 on the surgical device 102 and the optical waveform emitter 123 on the imaging device 120 (and, thus, the known distance $d_x$ therebetween) to determine the distance $d_y$, which is the sum of the distances $d_e$ and $d_A$.

Additionally or alternatively, time-of-flight from the optical waveform emitter 123 can be configured to determine the distance from the optical waveform emitter 123 to the surface 105 of the tissue 103. For example, a first waveform (or range of waveforms) can be utilized to determine the camera-to-critical structure distance $d_w$ and a second waveform (or range of waveforms) can be utilized to determine the distance to the surface 105 of the tissue 103. In such instances, the different waveforms can be utilized to determine the depth of the critical structure 101 below the surface 105 of the tissue 103.

Additionally or alternatively, in certain instances, the distance $d_A$ can be determined from an ultrasound, a registered magnetic resonance imaging (MRI) or computerized tomography (CT) scan. In still other instances, the distance $d_A$ can be determined with spectral imaging because the detection signal received by the imaging device can vary based on the type of material. For example, fat can decrease the detection signal in a first way, or a first amount, and collagen can decrease the detection signal in a different, second way, or a second amount.

Figure 4:
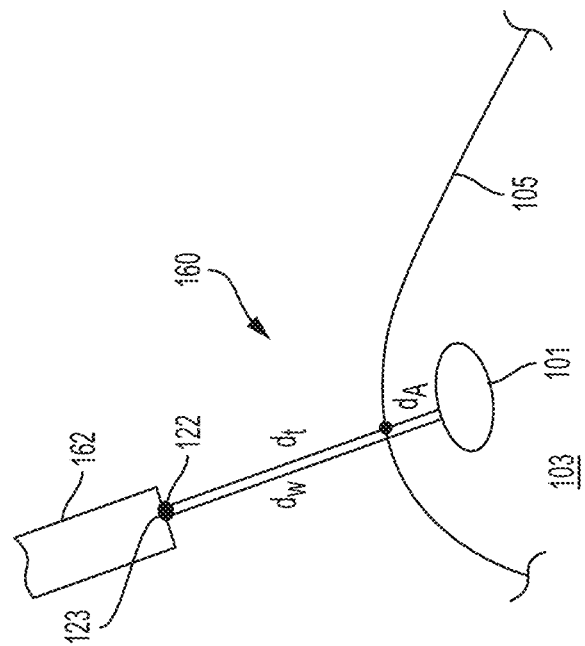
FIG. 4 is a schematic of a surgical visualization system configured to identify a critical structure below a tissue surface, wherein the surgical visualization system includes a pulsed light source for determining a depth $d_A$ of the critical structure below the tissue surface, according to at least one aspect of the present disclosure.

Referring now to a surgical visualization system 160 in FIG. 4, in which a surgical device 162 includes the optical waveform emitter 123 and the waveform sensor 122 that is configured to detect the reflected waveforms. The optical waveform emitter 123 can be configured to emit waveforms for determining the distances $d_t$ and $d_w$ from a common device, such as the surgical device 162, as further described herein. In such instances, the distance $d_A$ from the surface 105 of the tissue 103 to the surface of the critical structure 101 can be determined as follows:

$$d_A = d_w - d_t.$$

As disclosed herein, various information regarding visible tissue, embedded critical structures, and surgical devices can be determined by utilizing a combination approach that incorporates one or more time-of-flight distance sensors, spectral imaging, and/or structured light arrays in combination with an image sensor configured to detect the spectral wavelengths and the structured light arrays. Moreover, the image sensor can be configured to receive visible light and, thus, provide images of the surgical site to an imaging system. Logic or algorithms are employed to discern the information received from the time-of-flight sensors, spectral wavelengths, structured light, and visible light and render three-dimensional images of the surface tissue and underlying anatomical structures. In various instances, the imaging device 120 can include multiple image sensors.

Figure 6:
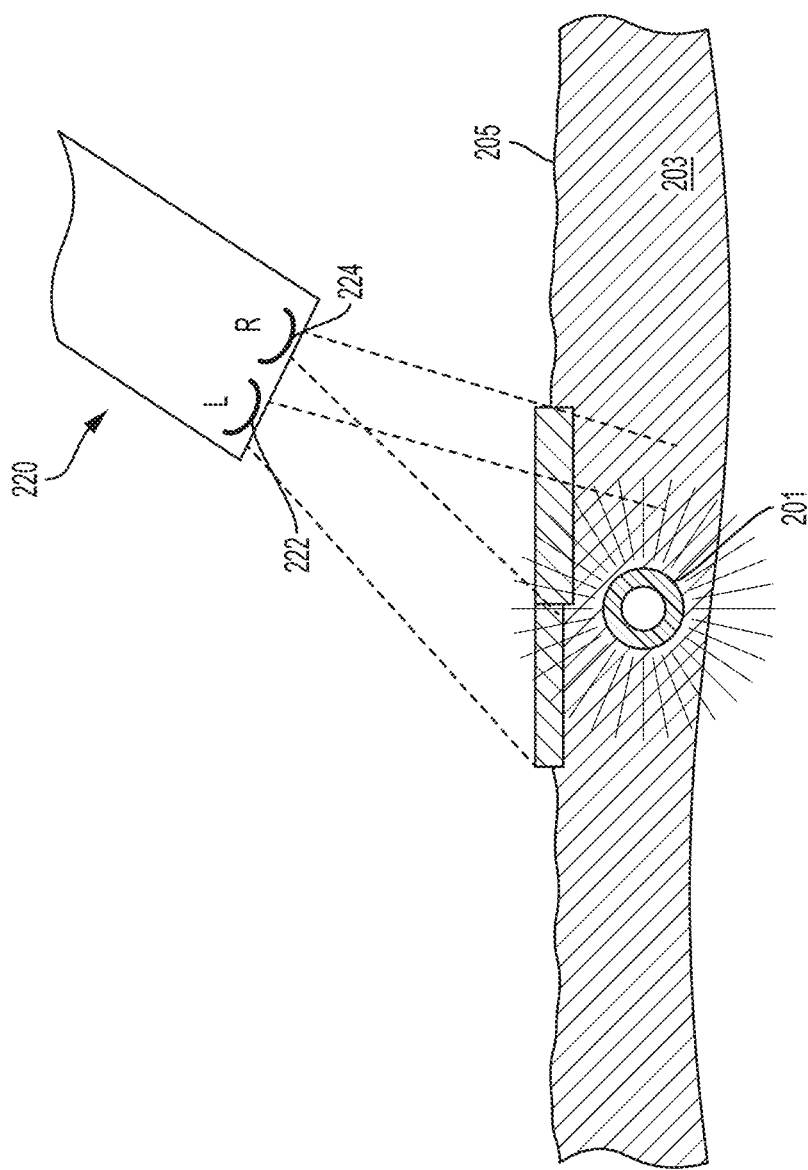
FIG. 6 is a schematic of a surgical visualization system including a three-dimensional camera, wherein the surgical visualization system is configured to identify a critical structure that is embedded within tissue, according to at least one aspect of the present disclosure.

The camera-to-critical structure distance $d_w$ can also be detected in one or more alternative ways. In one aspect, a fluoroscopy visualization technology, such as fluorescent indosciedine green (ICG), for example, can be utilized to illuminate a critical structure 201, as shown in FIGS. 6-8. A camera 220 can include two optical waveforms sensors 222, 224, which take simultaneous left-side and right-side images of the critical structure 201 (FIGS. 7A and 7B). In such instances, the camera 220 can depict a glow of the critical structure 201 below the surface 205 of the tissue 203, and the distance $d_w$ can be determined by the known distance between the sensors 222 and 224. In certain instances, distances can be determined more accurately by utilizing more than one camera or by moving a camera between multiple locations. In certain aspects, one camera can be controlled by a first robotic arm and a second camera by another robotic arm. In such a robotic system, one camera can be a follower camera on a follower arm, for example. The follower arm, and camera thereon, can be programmed to track the other camera and to maintain a particular distance and/or lens angle, for example.

Figure 9:
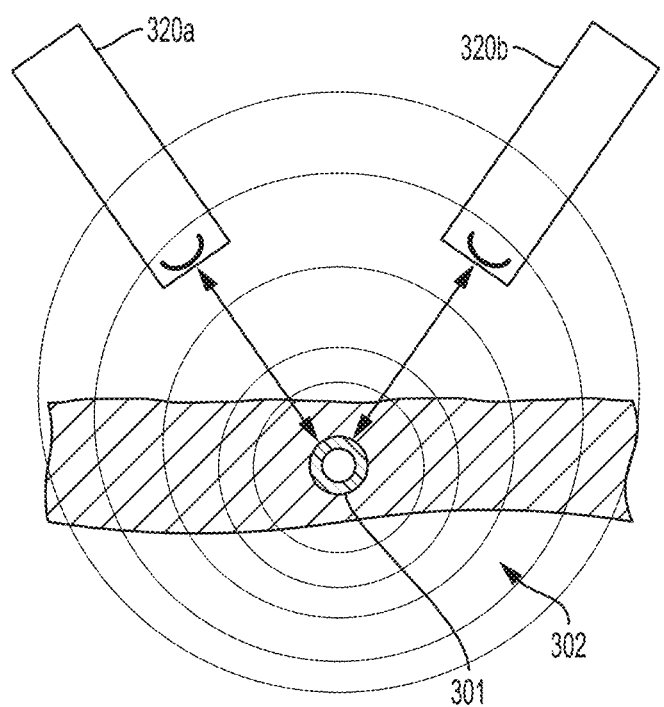
FIG. 9 is a schematic of a surgical visualization system utilizing two cameras to determine the position of an embedded critical structure, according to at least one aspect of the present disclosure.

In still other aspects, the surgical visualization system 100 may employ two separate waveform receivers (i.e. cameras/image sensors) to determine $d_w$. Referring now to FIG. 9, if a critical structure 301 or the contents thereof (e.g. a vessel or the contents of the vessel) can emit a signal 302, such as with fluoroscopy, then the actual location can be triangulated from two separate cameras 320a, 320b at known locations.

Figure 10B:
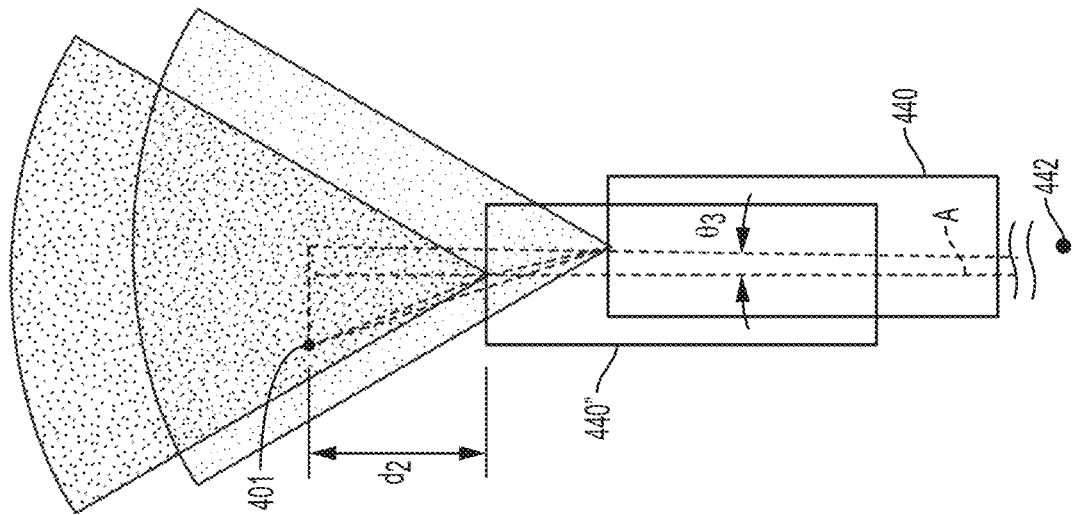
FIG. 10B is a schematic of the surgical visualization system of FIG. 10A, in which the camera is moved axially and rotationally between a plurality of known positions to determine a position of the embedded critical structure, according to at least one aspect of the present disclosure.
Figure 10A:
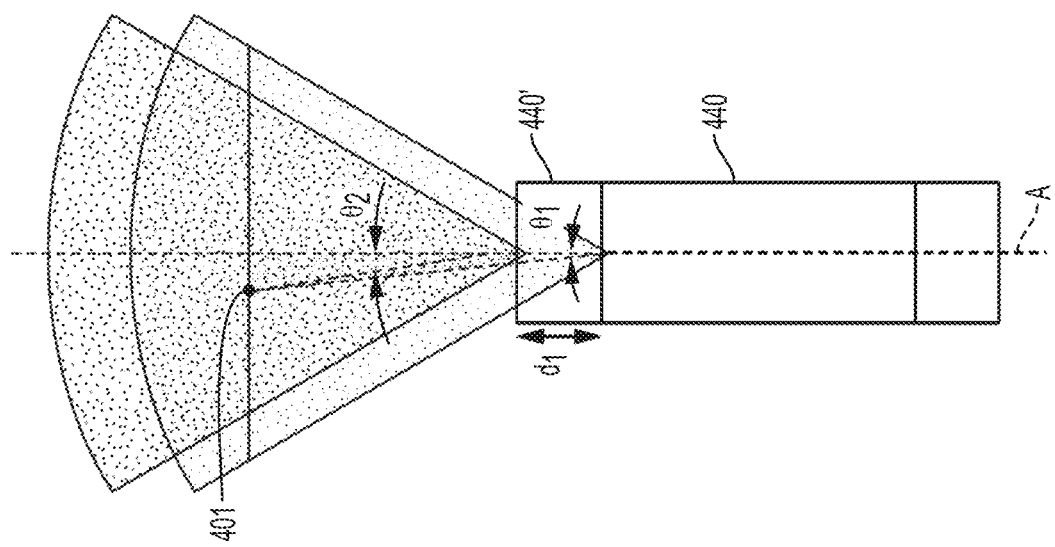
FIG. 10A is a schematic of a surgical visualization system utilizing a camera that is moved axially between a plurality of known positions to determine a position of an embedded critical structure, according to at least one aspect of the present disclosure.

In another aspect, referring now to FIGS. 10A and 10B, a surgical visualization system may employ a dithering or moving camera 440 to determine the distance $d_w$. The camera 440 is robotically-controlled such that the three-dimensional coordinates of the camera 440 at the different positions are known. In various instances, the camera 440 can pivot at a cannula or patient interface. For example, if a critical structure 401 or the contents thereof (e.g. a vessel or the contents of the vessel) can emit a signal, such as with fluoroscopy, for example, then the actual location can be triangulated from the camera 440 moved rapidly between two or more known locations. In FIG. 10A, the camera 440 is moved axially along an axis A. More specifically, the camera 440 translates a distance $d_1$ closer to the critical structure 401 along the axis A to the location indicated as a location 440', such as by moving in and out on a robotic arm. As the camera 440 moves the distance $d_1$ and the size of view change with respect to the critical structure 401, the distance to the critical structure 401 can be calculated. For example, a 4.28 mm axial translation (the distance $d_1$) can correspond to an angle $\theta_1$ of 6.28 degrees and an angle $\theta_2$ of 8.19 degrees. Additionally or alternatively, the camera 440 can rotate or sweep along an arc between different positions. Referring now to FIG. 10B, the camera 440 is moved axially along the axis A and is rotated an angle $\theta_3$ about the axis A. A pivot point 442 for rotation of the camera 440 is positioned at the cannula/patient interface. In FIG. 10B, the camera 440 is translated and rotated to a location 440". As the camera 440 moves and the edge of view changes with respect to the critical structure 401, the distance to the critical structure 401 can be calculated. In FIG. 10B, a distance $d_2$ can be 9.01 mm, for example, and the angle $\theta_3$ can be 0.9 degrees, for example.

Figure 5:
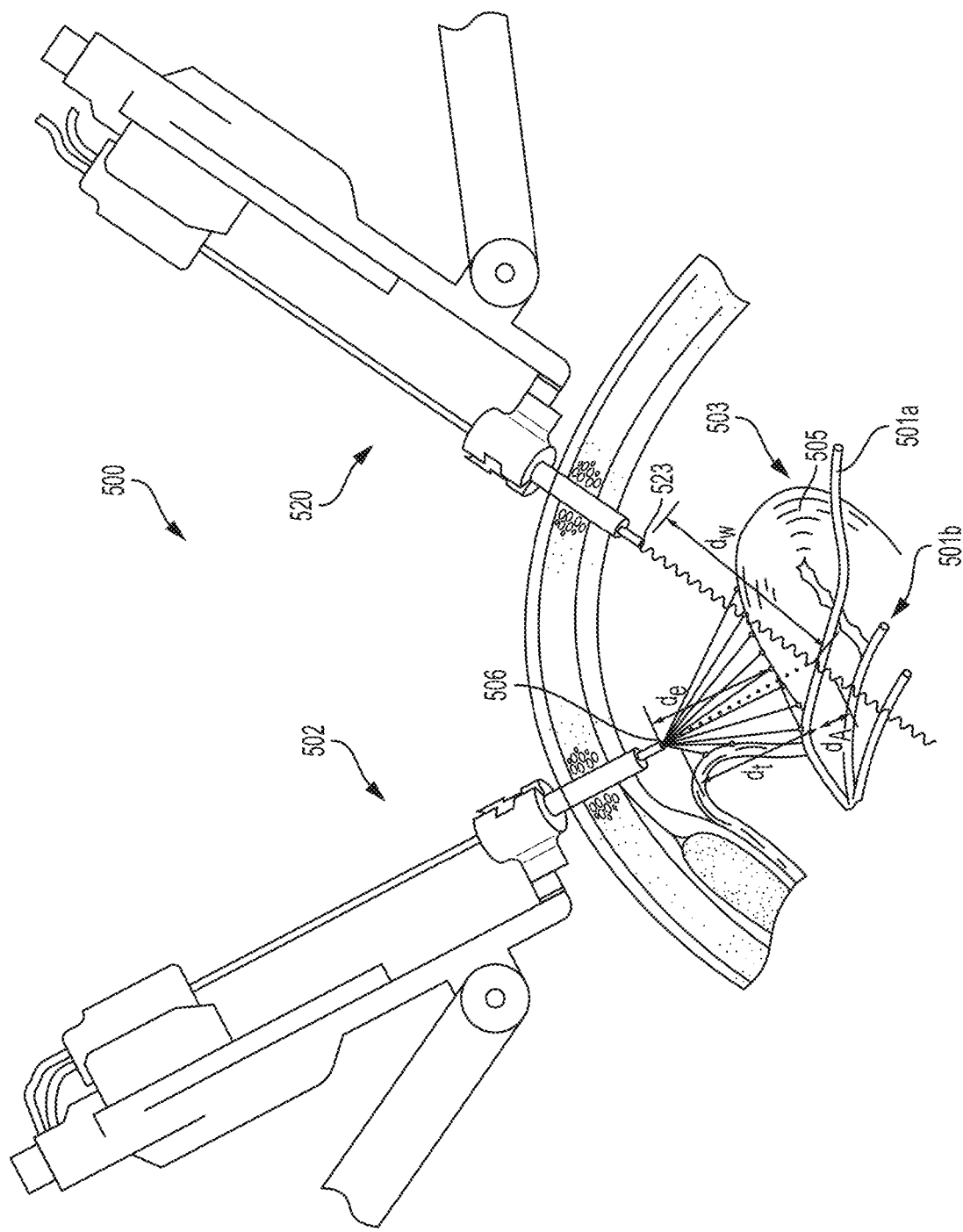
FIG. 5 is a schematic of a surgical visualization system including an imaging device and a surgical device, the surgical visualization system configured to identify a critical structure below a tissue surface, according to at least one aspect of the present disclosure.

FIG. 5 depicts a surgical visualization system 500, which is similar to the surgical visualization system 100 in many respects. In various instances, the surgical visualization system 500 can be a further exemplification of the surgical visualization system 100. Similar to the surgical visualization system 100, the surgical visualization system 500 includes a surgical device 502 and an imaging device 520. The imaging device 520 includes a spectral light emitter 523, which is configured to emit spectral light in a plurality of wavelengths to obtain a spectral image of hidden structures, for example. The imaging device 520 can also include a three-dimensional camera and associated electronic processing circuits in various instances. The surgical visualization system 500 is shown being utilized intraoperatively to identify and facilitate avoidance of certain critical structures, such as a ureter 501a and vessels 501b in an organ 503 (the uterus in this example), that are not visible on the surface.

The surgical visualization system 500 is configured to determine an emitter-to-tissue distance $d_e$ from an emitter 506 on the surgical device 502 to a surface 505 of the uterus 503 via structured light. The surgical visualization system 500 is configured to extrapolate a device-to-tissue distance $d_t$ from the surgical device 502 to the surface 505 of the uterus 503 based on the emitter-to-tissue distance $d_e$. The surgical visualization system 500 is also configured to determine a tissue-to-ureter distance $d_A$ from the ureter 501a to the surface 505 and a camera- to ureter distance $d_w$ from the imaging device 520 to the ureter 501a. As described herein with respect to FIG. 1, for example, the surgical visualization system 500 can determine the distance $d_w$ with spectral imaging and time-of-flight sensors, for example. In various instances, the surgical visualization system 500 can determine (e.g. triangulate) the tissue-to-ureter distance $d_A$ (or depth) based on other distances and/or the surface mapping logic described herein.

Figure 11:
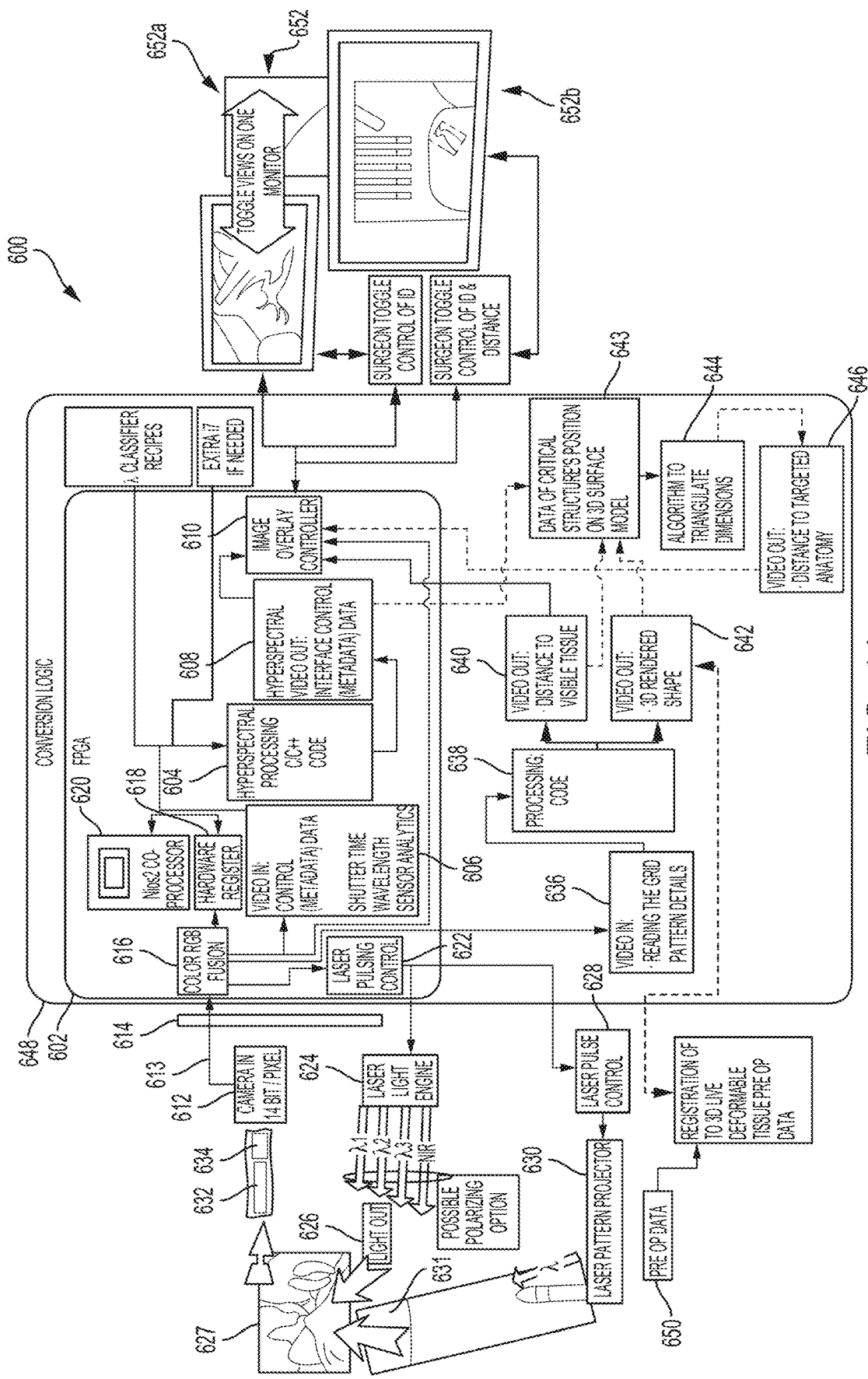
FIG. 11 is a schematic of a control system for a surgical visualization system, according to at least one aspect of the present disclosure.

Referring now to FIG. 11, where a schematic of a control system 600 for a surgical visualization system, such as the surgical visualization system 100, for example, is depicted. The control system 600 is a conversion system that integrates spectral signature tissue identification and structured light tissue positioning to identify critical structures, especially when those structures are obscured by other tissue, such as fat, connective tissue, blood, and/or other organs, for example. Such technology could also be useful for detecting tissue variability, such as differentiating tumors and/or non-healthy tissue from healthy tissue within an organ.

The control system 600 is configured for implementing a hyperspectral imaging and visualization system in which a molecular response is utilized to detect and identify anatomy in a surgical field of view. The control system 600 includes a conversion logic circuit 648 to convert tissue data to surgeon usable information. For example, the variable reflectance based on wavelengths with respect to obscuring material can be utilized to identify the critical structure in the anatomy. Moreover, the control system 600 combines the identified spectral signature and the structural light data in an image. For example, the control system 600 can be employed to create of three-dimensional data set for surgical use in a system with augmentation image overlays. Techniques can be employed both intraoperatively and preoperatively using additional visual information. In various instances, the control system 600 is configured to provide warnings to a clinician when in the proximity of one or more critical structures. Various algorithms can be employed to guide robotic automation and semi-automated approaches based on the surgical procedure and proximity to the critical structure(s).

A projected array of lights is employed to determine tissue shape and motion intraoperatively. Alternatively, flash Lidar may be utilized for surface mapping of the tissue.

The control system 600 is configured to detect the critical structure(s) and provide an image overlay of the critical structure and measure the distance to the surface of the visible tissue and the distance to the embedded/buried critical structure(s). In other instances, the control system 600 can measure the distance to the surface of the visible tissue or detect the critical structure(s) and provide an image overlay of the critical structure.

The control system 600 includes a spectral control circuit 602. The spectral control circuit 602 can be a field programmable gate array (FPGA) or another suitable circuit configuration as described herein in connection with FIGS. 2A-2C, for example. The spectral control circuit 602 includes a processor 604 to receive video input signals from a video input processor 606. The processor 604 can be configured for hyperspectral processing and can utilize C/C++ code, for example. The video input processor 606 receives video-in of control (metadata) data such as shutter time, wave length, and sensor analytics, for example. The processor 604 is configured to process the video input signal from the video input processor 606 and provide a video output signal to a video output processor 608, which includes a hyperspectral video-out of interface control (metadata) data, for example. The video output processor 608 provides the video output signal to an image overlay controller 610.

The video input processor 606 is coupled to a camera 612 at the patient side via a patient isolation circuit 614. As previously discussed, the camera 612 includes a solid state image sensor 634. The patient isolation circuit can include a plurality of transformers so that the patient is isolated from other circuits in the system. The camera 612 receives intraoperative images through optics 632 and the image sensor 634. The image sensor 634 can include a CMOS image sensor, for example, or may include any of the image sensor technologies discussed herein in connection with FIG. 2, for example. In one aspect, the camera 612 outputs images in 14 bit/pixel signals. It will be appreciated that higher or lower pixel resolutions may be employed without departing from the scope of the present disclosure. The isolated camera output signal 613 is provided to a color RGB fusion circuit 616, which employs a hardware register 618 and a Nios2 co-processor 620 to process the camera output signal 613. A color RGB fusion output signal is provided to the video input processor 606 and a laser pulsing control circuit 622.

The laser pulsing control circuit 622 controls a laser light engine 624. The laser light engine 624 outputs light in a plurality of wavelengths ($\lambda_1, \lambda_2, \lambda_3 \ldots \lambda_n$) including near infrared (NIR). The laser light engine 624 can operate in a plurality of modes. In one aspect, the laser light engine 624 can operate in two modes, for example. In a first mode, e.g. a normal operating mode, the laser light engine 624 outputs an illuminating signal. In a second mode, e.g. an identification mode, the laser light engine 624 outputs RGBG and NIR light. In various instances, the laser light engine 624 can operate in a polarizing mode.

Light output 626 from the laser light engine 624 illuminates targeted anatomy in an intraoperative surgical site 627. The laser pulsing control circuit 622 also controls a laser pulse controller 628 for a laser pattern projector 630 that projects a laser light pattern 631, such as a grid or pattern of lines and/or dots, at a predetermined wavelength ($\lambda_2$) on the operative tissue or organ at the surgical site 627. The camera 612 receives the patterned light as well as the reflected light output through the camera optics 632. The image sensor 634 converts the received light into a digital signal.

The color RGB fusion circuit 616 also outputs signals to the image overlay controller 610 and a video input module 636 for reading the laser light pattern 631 projected onto the targeted anatomy at the surgical site 627 by the laser pattern projector 630. A processing module 638 processes the laser light pattern 631 and outputs a first video output signal 640 representative of the distance to the visible tissue at the surgical site 627. The data is provided to the image overlay controller 610. The processing module 638 also outputs a second video signal 642 representative of a three-dimensional rendered shape of the tissue or organ of the targeted anatomy at the surgical site.

The first and second video output signals 640, 642 include data representative of the position of the critical structure on a three-dimensional surface model, which is provided to an integration module 643. In combination with data from the video out processor 608 of the spectral control circuit 602, the integration module 643 can determine the distance $d_A$ (FIG. 1) to a buried critical structure (e.g. via triangularization algorithms 644), and the distance $d_A$ can be provided to the image overlay controller 610 via a video out processor 646. The foregoing conversion logic can encompass the conversion logic circuit 648 intermediate video monitors 652 and the camera 624/laser pattern projector 630 positioned at the surgical site 627.

Preoperative data 650 from a CT or MRI scan can be employed to register or align certain three-dimensional deformable tissue in various instances. Such preoperative data 650 can be provided to the integration module 643 and ultimately to the image overlay controller 610 so that such information can be overlaid with the views from the camera 612 and provided to the video monitors 652. Registration of preoperative data is further described herein and in the aforementioned contemporaneously-filed U.S. Patent applications, including U.S. patent application Ser. No. 16/128, 195, titled INTEGRATION OF IMAGING DATA, for example, which are incorporated by reference herein in their respective entireties.

The video monitors 652 can output the integrated/augmented views from the image overlay controller 610. A clinician can select and/or toggle between different views on one or more monitors. On a first monitor 652a, the clinician can toggle between (A) a view in which a three-dimensional rendering of the visible tissue is depicted and (B) an augmented view in which one or more hidden critical structures are depicted over the three-dimensional rendering of the visible tissue. On a second monitor 652b, the clinician can toggle on distance measurements to one or more hidden critical structures and/or the surface of visible tissue, for example.

The control system 600 and/or various control circuits thereof can be incorporated into various surgical visualization systems disclosed herein.

Figure 12:
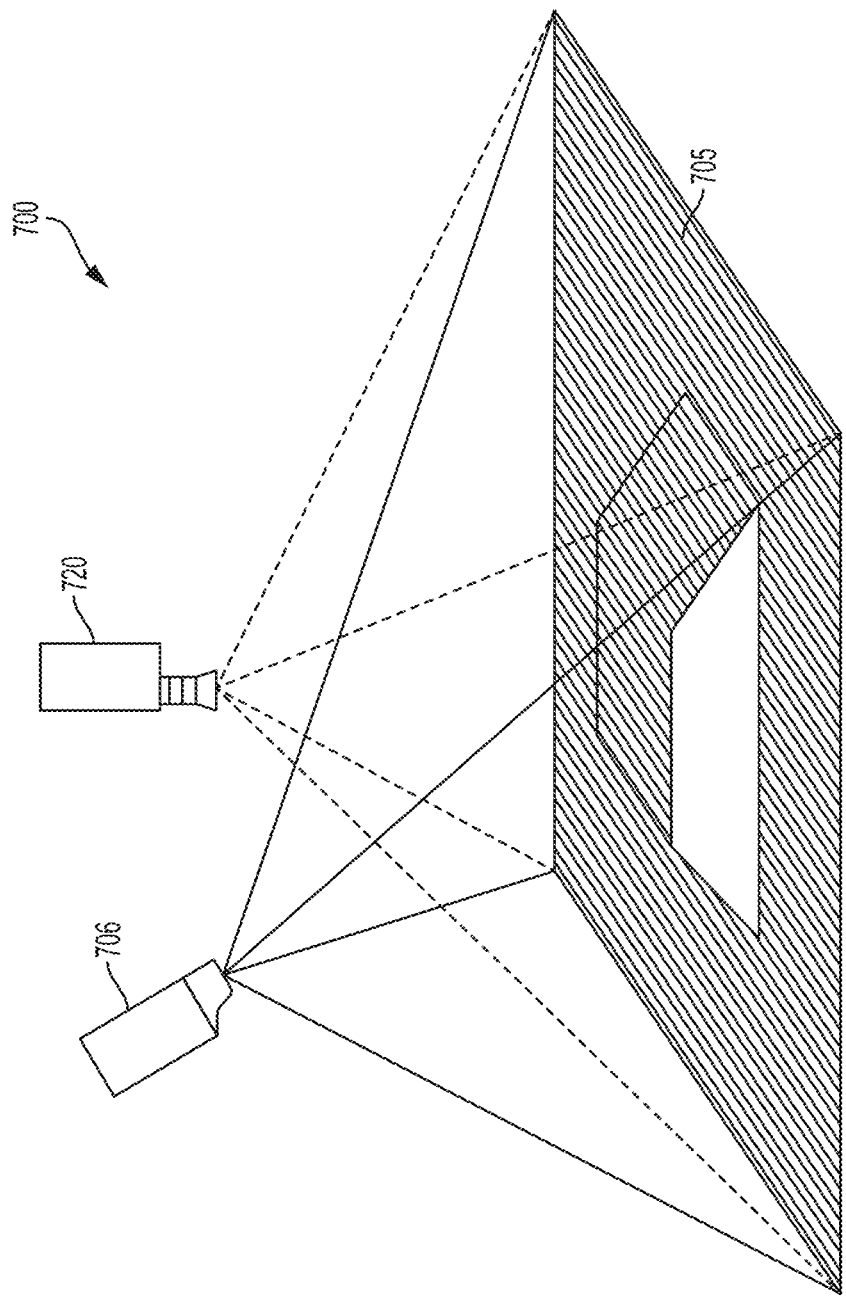
FIG. 12 is a schematic of a structured light source for a surgical visualization system, according to at least one aspect of the present disclosure.

FIG. 12 illustrates a structured (or patterned) light system 700, according to at least one aspect of the present disclosure. As described herein, structured light in the form of stripes or lines, for example, can be projected from a light source and/or projector 706 onto the surface 705 of targeted anatomy to identify the shape and contours of the surface 705. A camera 720, which can be similar in various respects to the imaging device 120 (FIG. 1), for example, can be configured to detect the projected pattern of light on the surface 705. The way that the projected pattern deforms upon striking the surface 705 allows vision systems to calculate the depth and surface information of the targeted anatomy.

In certain instances, invisible (or imperceptible) structured light can be utilized, in which the structured light is used without interfering with other computer vision tasks for which the projected pattern may be confusing. For example, infrared light or extremely fast frame rates of visible light that alternate between two exact opposite patterns can be utilized to prevent interference. Structured light is further described at en.wikipedia.org/wiki/Structured_light.

Figure 13:
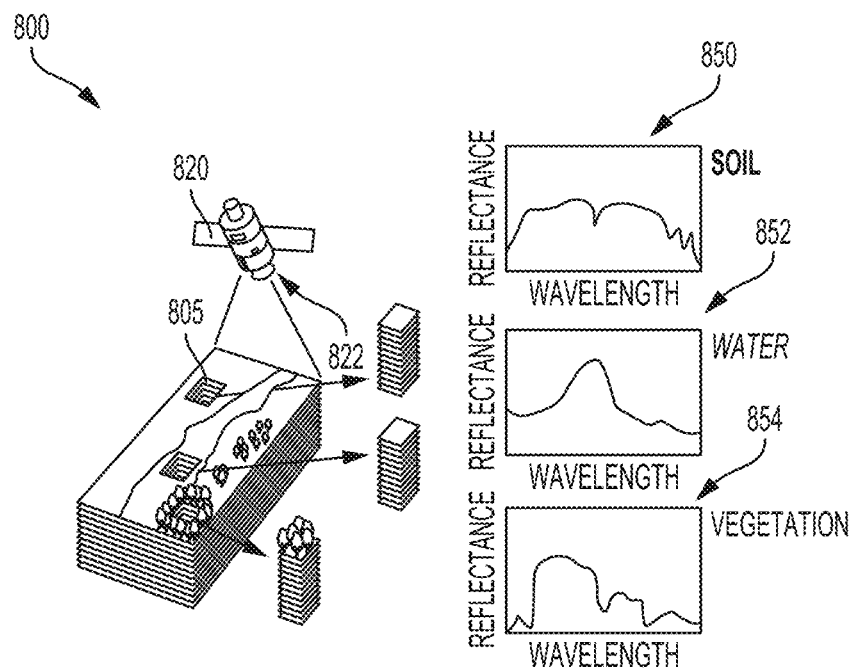
FIG. 13 is a schematic of a hyperspectral visualization system for imaging terrestrial features or objects, according to at least one aspect of the present disclosure.

Referring now to FIG. 13, by way example to illustrate the concept of hyperspectral imaging, a terrestrial hyperspectral imaging system 800 is shown. The terrestrial hyperspectral imaging system 800 is configured to image terrestrial features or objects, such as soil, water, and/or vegetation, for example. The terrestrial hyperspectral imaging system 700 includes a space-borne hyperspectral sensor 822 on a spacecraft 820 to conduct hyperspectral imaging of a portion of the Earth's surface 805. The spectral dimension includes several layers. Each pixel of the images contains a sampled spectrum that is used to identify the materials present in the pixel by their reflectance. The data can be converted to graphical representations 850, 852, 854 of reflectance as a function of wavelength for soil, water, and vegetation, respectively, for example. Terrestrial hyperspectral imaging is further described at www.markelowitz.com/Hyperspectral.html.

Figure 14:
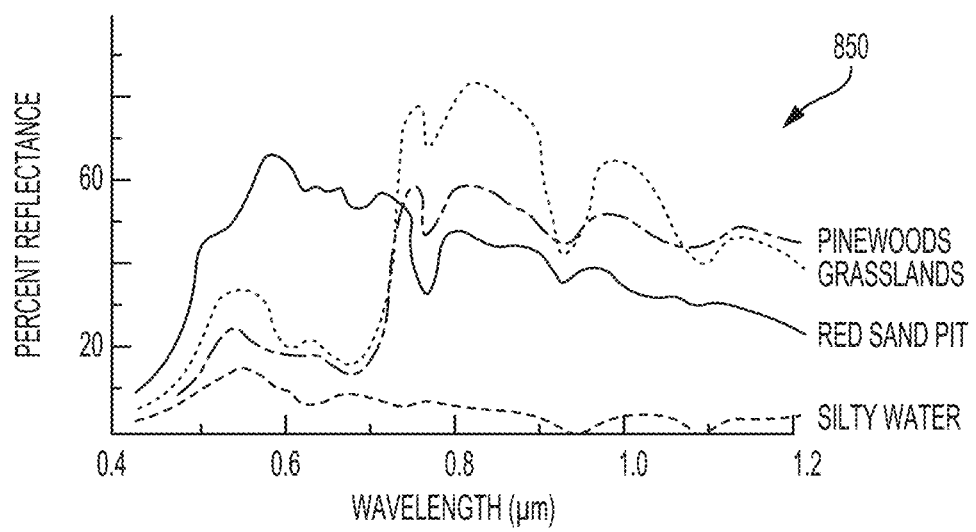
FIG. 14 is a graphical representation of hyperspectral signatures for various terrestrial features or objects, according to at least one aspect of the present disclosure.

Also by way example to illustrate the concept of hyperspectral imaging, FIG. 14 is a graphical representation 850 of hyperspectral signatures for various terrestrial features or objects, according to at least one aspect of the present disclosure. Percent reflectance is shown along the vertical axis and wavelength (nm) is shown along the horizontal axis. As shown, each object—pinewoods, grasslands, red sand pit, and silty water—has a unique hyperspectral signature that can be used to identify the object.

The hyperspectral imaging concepts described in connection with FIGS. 13 and 14 may be employed for different materials that have different wavelengths and bands of absorption, according to at least one aspect of the present disclosure. The following table illustrates the wavelengths and bands of absorption for various materials. A first range of wavelengths between 400 nm and 700 nm represents the visible light spectrum. A second range of wavelengths between 700 nm and 1400 nm represents the near infrared (NIR) spectrum. A third range of wavelengths between 1400 nm and 3000 nm represents a shortwave infrared (SWIR) spectrum. A first band centered at 1250 nm represents iron absorption and leaf moisture content. A second band between 1500 nm and 1750 nm represents plastics, fiberglass, and petroleum. A third band between 200 nm and 2400 nm represents mineral ID.

TABLE 1 specifies wavelengths and bands of absorption for various materials.

TABLE 1

| Wavelength (nm) | Region | Band(s) | Material |
| --- | --- | --- | --- |
| 400-700 | Visible | | |
| 700-1400 | NIR | | |
| 1400-3000 | SWIR | 1—centered at 1250 | Iron adsorption |
| | | | Leaf moisture content |
| | | 2—1500-1750 | Plastics |

TABLE 1-continued

| Wavelength (nm) | Region | Band(s) | Material |
|---|---|---|---|
| | 3—200-2400 nm | | Fiberglass Petroleum Mineral ID |

Referring now to FIGS. 15A-15C, as a further illustration of hyperspectral imaging concepts, tests were conducted in which spectral imaging was applied to a fried egg 952. An image of the fried egg 952 with a yellow egg yolk 954 and an egg white 956 surrounding the egg yolk 954 is shown in FIG. 15A. A graphical representation 950 of spectral signatures for the fried egg 952 are shown in FIG. 15B. Specifically, the graphical representation 950 shows absorption units versus wavelength (nm) for the egg yolk 954 and the egg white 956 of the fried egg 952. In FIG. 15C, a spectral image (in black-and-white) of the fried egg 952 is shown, in which the image is augmented to differentiate between the egg yolk portion and the egg white portion based on the hyperspectral signature data.

In various instances, hyperspectral imaging technology, as described herein for illustrative purposes with respect to terrestrial features and objects and a fried egg, can be employed to identify signatures in anatomical structures in order to differentiate a critical structure from obscurants. Hyperspectral imaging technology may provide a visualization system that can provide a way to identify critical structures such as ureters and/or blood vessels, for example, especially when those structures are obscured by fat, connective tissue, blood, or other organs, for example. The use of the difference in reflectance of different wavelengths in the infrared (IR) spectrum may be employed to determine the presence of key structures versus obscurants. Referring now to FIGS. 16-18, illustrative hyperspectral signatures for a ureter, an artery, and nerve tissue with respect to obscurants such as fat, lung tissue, and blood, for example, are depicted.

FIG. 16 is a graphical representation 1050 of an illustrative ureter signature versus obscurants. The plots represent reflectance as a function of wavelength (nm) for wavelengths for fat, lung tissue, blood, and a ureter. FIG. 17 is a graphical representation 1052 of an illustrative artery signature versus obscurants. The plots represent reflectance as a function of wavelength (nm) for fat, lung tissue, blood, and a vessel. FIG. 18 is a graphical representation 1054 of an illustrative nerve signature versus obscurants. The plots represent reflectance as a function of wavelength (nm) for fat, lung tissue, blood, and a nerve.

In various instances, select wavelengths for spectral imaging can be identified and utilized based on the anticipated critical structures and/or obscurants at a surgical site (i.e. "selective spectral" imaging). By utilizing selective spectral imaging, the amount of time required to obtain the spectral image can be minimized such that the information can be obtained in real-time, or near real-time, and utilized intraoperatively. In various instances, the wavelengths can be selected by a clinician or by a control circuit based on input by the clinician. In certain instances, the wavelengths can be selected based on machine learning and/or big data accessible to the control circuit via a cloud, for example.

The foregoing application of spectral imaging to tissue can be utilized intraoperatively to measure the distance between a waveform emitter and a critical structure that is obscured by tissue. In one aspect of the present disclosure, referring now to FIGS. 19 and 20, a time-of-flight sensor system 1104 utilizing waveforms 1124, 1125 is shown. The time-of-flight sensor system 1104 can be incorporated into the surgical visualization system 100 (FIG. 1) in certain instances. The time-of-flight sensor system 1104 includes a waveform emitter 1106 and a waveform receiver 1108 on the same surgical device 1102. The emitted wave 1124 extends to the critical structure 1101 from the emitter 1106 and the received wave 1125 is reflected back to by the receiver 1108 from the critical structure 1101. The surgical device 1102 is positioned through a trocar 1110 that extends into a cavity 1107 in a patient.

The waveforms 1124, 1125 are configured to penetrate obscuring tissue 1103. For example, the wavelengths of the waveforms 1124, 1125 can be in the NIR or SWIR spectrum of wavelengths. In one aspect, a spectral signal (e.g. hyperspectral, multispectral, or selective spectral) or a photoacoustic signal can be emitted from the emitter 1106 and can penetrate the tissue 1103 in which the critical structure 1101 is concealed. The emitted waveform 1124 can be reflected by the critical structure 1101. The received waveform 1125 can be delayed due to the distance d between the distal end of the surgical device 1102 and the critical structure 1101. In various instances, the waveforms 1124, 1125 can be selected to target the critical structure 1101 within the tissue 1103 based on the spectral signature of the critical structure 1101, as further described herein. In various instances, the emitter 1106 is configured to provide a binary signal on and off, as shown in FIG. 20, for example, which can be measured by the receiver 1108.

Based on the delay between the emitted wave 1124 and the received wave 1125, the time-of-flight sensor system 1104 is configured to determine the distance d (FIG. 19). A time-of-flight timing diagram 1130 for the emitter 1106 and the receiver 1108 of FIG. 19 is shown in FIG. 20. The delay is a function of the distance d and the distance d is given by:

$$d = \frac{ct}{2} \cdot \frac{q_2}{q_1 + q_2}$$

where:
c=the speed of light;
t=length of pulse;
$q_1$=accumulated charge while light is emitted; and
$q_2$=accumulated charge while light is not being emitted.

As provided herein, the time-of-flight of the waveforms 1124, 1125 corresponds to the distance d in FIG. 19. In various instances, additional emitters/receivers and/or pulsing signals from the emitter 1106 can be configured to emit a non-penetrating signal. The non-penetrating tissue can be configured to determine the distance from the emitter to the surface 1105 of the obscuring tissue 1103. In various instances, the depth of the critical structure 1101 can be determined by:

$$d_A = d_w - d_t$$

where:
$d_A$=the depth of the critical structure 1101;
$d_w$=the distance from the emitter 1106 to the critical structure 1101 (d in FIG. 19); and
$d_t$=the distance from the emitter 1106 (on the distal end of the surgical device 1102) to the surface 1105 of the obscuring tissue 1103.

In one aspect of the present disclosure, referring now to FIG. 21, a time-of-flight sensor system 1204 utilizing waves 1224a, 1224b, 1224c, 1225a, 1225b, 1225c is shown. The time-of-flight sensor system 1204 can be incorporated into the surgical visualization system 100 (FIG. 1) in certain instances. The time-of-flight sensor system 1204 includes a waveform emitter 1206 and a waveform receiver 1208. The waveform emitter 1206 is positioned on a first surgical device 1202a, and the waveform receiver 1208 is positioned on a second surgical device 1202b. The surgical devices 1202a, 1202b are positioned through their respective trocars 1210a, 1210b, respectively, which extend into a cavity 1207 in a patient. The emitted waves 1224a, 1224b, 1224c extend toward a surgical site from the emitter 1206 and the received waves 1225a, 1225b, 1225c are reflected back to the receiver 1208 from various structures and/or surfaces at the surgical site.

The different emitted waves 1224a, 1224b, 1224c are configured to target different types of material at the surgical site. For example, the wave 1224a targets the obscuring tissue 1203, the wave 1224b targets a first critical structure 1201a (e.g. a vessel), and the wave 1224c targets a second critical structure 1201b (e.g. a cancerous tumor). The wavelengths of the waves 1224a, 1224b, 1224c can be in the visible light, NIR, or SWIR spectrum of wavelengths. For example, visible light can be reflected off a surface 1205 of the tissue 1203 and NIR and/or SWIR waveforms can be configured to penetrate the surface 1205 of the tissue 1203. In various aspects, as described herein, a spectral signal (e.g. hyperspectral, multispectral, or selective spectral) or a photoacoustic signal can be emitted from the emitter 1206. In various instances, the waves 1224b, 1224c can be selected to target the critical structures 1201a, 1201b within the tissue 1203 based on the spectral signature of the critical structure 1201a, 1201b, as further described herein. Photoacoustic imaging is further described herein and in the aforementioned contemporaneously-filed U.S. Patent applications, which are incorporated by reference herein in their respective entireties.

The emitted waves 1224a, 1224b, 1224c can be reflected off the targeted material (i.e. the surface 1205, the first critical structure 1201a, and the second structure 1201b, respectively). The received waveforms 1225a, 1225b, 1225c can be delayed due to the distances $d_{1a}$, $d_{2a}$, $d_{3a}$, $d_{1b}$, $d_{2b}$, $d_{2c}$ indicated in FIG. 21.

In the time-of-flight sensor system 1204, in which the emitter 1206 and the receiver 1208 are independently positionable (e.g., on separate surgical devices 1202a, 1202b and/or controlled by separate robotic arms), the various distances $d_{1a}$, $d_{2a}$, $d_{3a}$, $d_{1b}$, $d_{2b}$, $d_{2c}$ can be calculated from the known position of the emitter 1206 and the receiver 1208. For example, the positions can be known when the surgical devices 1202a, 1202b are robotically-controlled. Knowledge of the positions of the emitter 1206 and the receiver 1208, as well as the time of the photon stream to target a certain tissue and the information received by the receiver 1208 of that particular response can allow a determination of the distances $d_{1a}$, $d_{2a}$, $d_{3a}$, $d_{1b}$, $d_{2b}$, $d_{2c}$. In one aspect, the distance to the obscured critical structures 1201a, 1201b can be triangulated using penetrating wavelengths. Because the speed of light is constant for any wavelength of visible or invisible light, the time-of-flight sensor system 1204 can determine the various distances.

Referring still to FIG. 21, in various instances, in the view provided to the clinician, the receiver 1208 can be rotated such that the center of mass of the target structure in the resulting images remains constant, i.e., in a plane perpendicular to the axis of a select target structures 1203, 1201a, or 1201b. Such an orientation can quickly communicate one or more relevant distances and/or perspectives with respect to the critical structure. For example, as shown in FIG. 21, the surgical site is displayed from a viewpoint in which the critical structure 1201a is perpendicular to the viewing plane (i.e. the vessel is oriented in/out of the page). In various instances, such an orientation can be default setting; however, the view can be rotated or otherwise adjusted by a clinician. In certain instances, the clinician can toggle between different surfaces and/or target structures that define the viewpoint of the surgical site provided by the imaging system.

In various instances, the receiver 1208 can be mounted on a trocar or cannula, such as the trocar 1210b, for example, through which the surgical device 1202b is positioned. In other instances, the receiver 1208 can be mounted on a separate robotic arm for which the three-dimensional position is known. In various instances, the receiver 1208 can be mounted on a movable arm that is separate from the robot that controls the surgical device 1202a or can be mounted to an operating room (OR) table that is intraoperatively registerable to the robot coordinate plane. In such instances, the position of the emitter 1206 and the receiver 1208 can be registerable to the same coordinate plane such that the distances can be triangulated from outputs from the time-of-flight sensor system 1204.

Combining time-of-flight sensor systems and near-infrared spectroscopy (NIRS), termed TOF-NIRS, which is capable of measuring the time-resolved profiles of NIR light with nanosecond resolution can be found in the article titled TIME-OF-FLIGHT NEAR-INFRARED SPECTROSCOPY FOR NONDESTRUCTIVE MEASUREMENT OF INTERNAL QUALITY IN GRAPEFRUIT, in the Journal of the American Society for Horticultural Science, May 2013 vol. 138 no. 3 225-228, which is incorporated by reference herein in its entirety, and is accessible at journal.ashspublications.org/content/138/3/225.full.

In various instances, time-of-flight spectral waveforms are configured to determine the depth of the critical structure and/or the proximity of a surgical device to the critical structure. Moreover, the various surgical visualization systems disclosed herein include surface mapping logic that is configured to create three-dimensional rendering of the surface of the visible tissue. In such instances, even when the visible tissue obstructs a critical structure, the clinician can be aware of the proximity (or lack thereof) of a surgical device to the critical structure. In one instances, the topography of the surgical site is provided on a monitor by the surface mapping logic. If the critical structure is close to the surface of the tissue, spectral imaging can convey the position of the critical structure to the clinician. For example, spectral imaging may detect structures within 5 or 10 mm of the surface. In other instances, spectral imaging may detect structures 10 or 20 mm below the surface of the tissue. Based on the known limits of the spectral imaging system, the system is configured to convey that a critical structure is out-of-range if it is simply not detected by the spectral imaging system. Therefore, the clinician can continue to move the surgical device and/or manipulate the tissue. When the critical structure moves into range of the spectral imaging system, the system can identify the structure and, thus, communicate that the structure is within range. In such instances, an alert can be provided when a structure is initially identified and/or moved further within a predefined proximity zone. In such instances, even non-identification of a critical structure by a spectral imaging system with known bounds/ranges can provide proximity information (i.e. the lack of proximity) to the clinician.

Various surgical visualization systems disclosed herein can be configured to identify intraoperatively the presence of and/or proximity to critical structure(s) and to alert a clinician prior to damaging the critical structure(s) by inadvertent dissection and/or transection. In various aspects, the surgical visualization systems are configured to identify one or more of the following critical structures: ureters, bowel, rectum, nerves (including the phrenic nerve, recurrent laryngeal nerve [RLN], promontory facial nerve, vagus nerve, and branches thereof), vessels (including the pulmonary and lobar arteries and veins, inferior mesenteric artery [IMA] and branches thereof, superior rectal artery, sigmoidal arteries, and left colic artery), superior mesenteric artery (SMA) and branches thereof (including middle colic artery, right colic artery, ilecolic artery), hepatic artery and branches thereof, portal vein and branches thereof, splenic artery/vein and branches thereof, external and internal (hypogastric) ileac vessels, short gastric arteries, uterine arteries, middle sacral vessels, and lymph nodes, for example. Moreover, the surgical visualization systems are configured to indicate proximity of surgical device(s) to the critical structure(s) and/or warn the clinician when surgical device(s) are getting close to the critical structure(s).

Various aspects of the present disclosure provide intraoperative critical structure identification (e.g., identification of ureters, nerves, and/or vessels) and instrument proximity monitoring. For example, various surgical visualization systems disclosed herein can include spectral imaging and surgical instrument tracking, which enable the visualization of critical structures below the surface of the tissue, such as 1.0-1.5 cm below the surface of the tissue, for example. In other instances, the surgical visualization system can identify structures less than 1.0 cm or more the 1.5 cm below the surface of the tissue. For example, even a surgical visualization system that can identify structures only within 0.2 mm of the surface, for example, can be valuable if the structure cannot otherwise be seen due to the depth. In various aspects, the surgical visualization system can augment the clinician's view with a virtual depiction of the critical structure as a visible white-light image overlay on the surface of visible tissue, for example. The surgical visualization system can provide real-time, three-dimensional spatial tracking of the distal tip of surgical instruments and can provide a proximity alert when the distal tip of a surgical instrument moves within a certain range of the critical structure, such as within 1.0 cm of the critical structure, for example.

Various surgical visualization systems disclosed herein can identify when dissection is too close to a critical structure. Dissection may be "too close" to a critical structure based on the temperature (i.e. too hot within a proximity of the critical structure that may risk damaging/heating/melting the critical structure) and/or based on tension (i.e. too much tension within a proximity of the critical structure that may risk damaging/tearing/pulling the critical structure). Such a surgical visualization system can facilitate dissection around vessels when skeletonizing the vessels prior to ligation, for example. In various instances, a thermal imaging camera can be utilized to read the heat at the surgical site and provide a warning to the clinician that is based on the detected heat and the distance from a tool to the structure. For example, if the temperature of the tool is over a predefined threshold (such as 120 degrees F., for example), an alert can be provided to the clinician at a first distance (such as 10 mm, for example), and if the temperature of the tool is less than or equal to the predefined threshold, the alert can be provided to the clinician at a second distance (such as 5 mm, for example). The predefined thresholds and/or warning distances can be default settings and/or programmable by the clinician. Additionally or alternatively, a proximity alert can be linked to thermal measurements made by the tool itself, such as a thermocouple that measures the heat in a distal jaw of a monopolar or bipolar dissector or vessel sealer, for example.

Various surgical visualization systems disclosed herein can provide adequate sensitivity with respect to a critical structure and specificity to enable a clinician to proceed with confidence in a quick but safe dissection based on the standard of care and/or device safety data. The system can function intraoperatively and in real-time during a surgical procedure with minimal ionizing radiation risk to a patient or a clinician and, in various instances, no risk of ionizing radiation risk to the patient or the clinician. Conversely, in a fluoroscopy procedure, the patient and clinician(s) may be exposed to ionizing radiation via an X-ray beam, for example, that is utilized to view the anatomical structures in real-time.

Various surgical visualization system disclosed herein can be configured to detect and identify one or more desired types of critical structures in a forward path of a surgical device, such as when the path of the surgical device is robotically controlled, for example. Additionally or alternatively, the surgical visualization system can be configured to detect and identify one or more types of critical structures in a surrounding area of the surgical device and/or in multiple planes/dimensions, for example.

Various surgical visualization systems disclosed herein can be easy to operate and/or interpret. Moreover, various surgical visualization systems can incorporate an "override" feature that allows the clinician to override a default setting and/or operation. For example, a clinician can selectively turn off alerts from the surgical visualization system and/or get closer to a critical structure than suggested by the surgical visualization system such as when the risk to the critical structure is less than risk of avoiding the area (e.g. when removing cancer around a critical structure the risk of leaving the cancerous tissue can be greater than the risk of damage to the critical structure).

Various surgical visualization systems disclosed herein can be incorporated into a surgical system and/or used during a surgical procedure with limited impact to the workflow. In other words, implementation of the surgical visualization system may not change the way the surgical procedure is implemented. Moreover, the surgical visualization system can be economical in comparison to the costs of an inadvertent transection. Data indicates the reduction in inadvertent damage to a critical structure can drive incremental reimbursement.

Various surgical visualization systems disclosed herein can operate in real-time, or near real-time, and far enough in advance to enable a clinician to anticipate critical structure (s). For example, a surgical visualization system can provide enough time to "slow down, evaluate, and avoid" in order to maximize efficiency of the surgical procedure.

Various surgical visualization systems disclosed herein may not require a contrast agent, or dye, that is injected into tissue. For example, spectral imaging is configured to visualize hidden structures intraoperatively without the use of a contrast agent or dye. In other instances, the contrast agent can be easier to inject into the proper layer(s) of tissue than other visualization systems. The time between injection of the contrast agent and visualization of the critical structure can be less than two hours, for example.

Various surgical visualization systems disclosed herein can be linked with clinical data and/or device data. For example, data can provide boundaries for how close energy-enabled surgical devices (or other potentially damaging devices) should be from tissue that the surgeon does not want to damage. Any data modules that interface with the surgical visualization systems disclosed herein can be provided integrally or separately from a robot to enable use with stand-alone surgical devices in open or laparoscopic procedures, for example. The surgical visualization systems can be compatible with robotic surgical systems in various instances. For example, the visualization images/information can be displayed in a robotic console.

In various instances, clinicians may not know the location of a critical structure with respect to a surgical tool. For example, when a critical structure is embedded in tissue, the clinician may be unable to ascertain the location of the critical structure. In certain instances, a clinician may want to keep a surgical device outside a range of positions surrounding the critical structure and/or away from the visible tissue covering the hidden critical structure. When the location of a concealed critical structure is unknown, the clinician may risk moving too close to the critical structure, which can result in inadvertent trauma and/or dissection of the critical structure and/or too much energy, heat, and/or tension in proximity of the critical structure. Alternatively, the clinician may stay too far away from a suspected location of the critical structure and risk affecting tissue at a less desirable location in an effort to avoid the critical structure.

A surgical visualization system is provided that presents surgical device tracking with respect to one or more critical structures. For example, the surgical visualization system can track the proximity of a surgical device with respect to a critical structure. Such tracking can occur intraoperatively, in real-time, and/or in near real-time. In various instances, the tracking data can be provided to the clinicians via a display screen (e.g. a monitor) of an imaging system.

In one aspect of the present disclosure, a surgical visualization system includes a surgical device comprising an emitter configured to emit a structured light pattern onto a visible surface, an imaging system comprising a camera configured to detect an embedded structure and the structured light pattern on the visible surface, and a control circuit in signal communication with the camera and the imaging system, wherein the control circuit is configured to determine a distance from the surgical device to the embedded structure and provide a signal to the imaging system indicative of the distance. For example, the distance can be determined by computing a distance from the camera to the critical structure that is illuminated with fluoroscopy technology and based on a three-dimensional view of the illuminated structure provided by images from multiple lenses (e.g. a left-side lens and a right-side lens) of the camera. The distance from the surgical device to the critical structure can be triangulated based on the known positions of the surgical device and the camera, for example. Alternative means for determining the distance to an embedded critical structure are further described herein. For example, NIR time-of-flight distance sensors can be employed. Additionally or alternatively, the surgical visualization system can determine a distance to visible tissue overlying/covering an embedded critical structure. For example, the surgical visualization system can identify a hidden critical structure and augment a view of the hidden critical structure by depicting a schematic of the hidden critical structure on the visible structure, such as a line on the surface of the visible tissue. The surgical visualization system can further determine the distance to the augmented line on the visible tissue.

By providing the clinician with up-to-date information regarding the proximity of the surgical device to the concealed critical structure and/or visible structure, as provided by the various surgical visualization systems disclosed herein, the clinician can make more informed decisions regarding the placement of the surgical device relative to the concealed critical structure. For example, the clinician can view the distance between the surgical device and the critical structure in real-time/intraoperatively and, in certain instances, an alert and/or warning can be provided by the imaging system when the surgical device is moved within a predefined proximity and/or zone of the critical structure. In certain instances, the alert and/or warning can be provided when the trajectory of the surgical device indicates a likely collision with a "no-fly" zone in the proximity of the critical structure (e.g. within 1 mm, 2 mm, 5 mm, 10 mm, 20 mm or more of the critical structure). In such instances, the clinician can maintain momentum throughout the surgical procedure without requiring the clinician to monitor a suspected location of the critical structure and the surgical device's proximity thereto. As a result, certain surgical procedures can be performed more quickly, with fewer pauses/interruptions, and/or with improved accuracy and/or certainty, for example. In one aspect, the surgical visualization system can be utilized to detect tissue variability, such as the variability of tissue within an organ to differentiate tumors/cancerous tissue/unhealthy tissue from healthy tissue. Such a surgical visualization system can maximize the removal of the unhealthy tissue while minimizing the removal of the healthy tissue.

Referring now to FIGS. 22-24, a surgical visualization system 1400 including a three-dimensional camera 1420 and a surgical device 1402 is shown. The camera 1420 includes an image sensor, as further described herein. The surgical visualization system 1400 can be similar to the surgical visualization system 100 (FIG. 1) in various aspects. For example, the surgical visualization system 1400 can be configured to identify one or more critical structures 1401 embedded below a surface 1405 of a tissue 1403, and to determine one or more distances with respect to the surface 1405 and/or the critical structure(s) 1401.

The surgical device 1402 includes an emitter 1406 configured to emit a pattern of structured light. The pattern is configured to reflect off a surface, and the reflected light can be detected by a camera or sensor, such as the camera 1420. Based on the reflected pattern, a control circuit is configured to determine the contours of the surface 1405 and one of more distances with respect to the surface 1405. For example, the control circuit can generate a three-dimensional model of the surface. Various control circuits are further described herein (e.g. see FIGS. 2 and 11).

The camera 1420 is a three-dimensional camera. For example, the camera 1420 includes a two-dimensional left-side lens, or sensor, 1408a, and a two-dimensional right-side lens, or sensor, 1408b. The lenses 1408a, 1408b are configured to detect one or more critical structures, such as the critical structure 1401, which is embedded within the tissue 1403. In various instances, the critical structure 1401 can be illuminated with a contrast agent, such as ICG, for example, and imaged via fluoroscopy techniques, for example. Furthermore, the left-side lens 1408a is configured to detect a two-dimensional view of the illuminated critical structure 1401, which is shown in FIG. 23, and the right-side lens 1408b is configured to detect another two-dimensional view of the illuminated critical structure 1401, which is also shown in FIG. 23.

The two-dimensional views from the lenses 1408a, 1408b can be integrated or combined to generate a three-dimensional view of the illuminated critical structure 1401 embedded in the anatomical target tissue. In various instances, the distance from the surgical device 1402 to the critical structure 1401 can be determined from the images obtained by the camera 1420. For example, the distance can be determined by applying an algorithm to both of the images obtained by the lenses 1408a, 1408b. For example, the distance in the left-hand image $d_l$ (FIG. 23) and the distance in the right-hand image $d_r$ (FIG. 23) can be averaged to obtain a distance d (FIG. 22) from the surgical device 1402 to the critical structure 1401 as follows:

$$d = \frac{d_l - d_r}{2}.$$

In various instances, because the relative positions of the camera 1420 and the surgical device 1402 are known (i.e., in a registered coordinate system such as the same robotic coordinate system), the distance from the surgical device 1402 to the critical structure 1401 can be triangulated, for example, when the distance from the critical structure 1401 to the camera 1420 is known. The robot has coordinate position knowledge of the arms (e.g., the surgical device 1402 and the camera 1420) and, thus, can triangulate to determine the intersection distance. Alternative means for determining the distance d between a surgical device and a critical structure are further described herein (e.g. ultrasound, time-of-flight measurements systems, hyperspectral signal analysis, etc.).

Referring primarily to FIG. 23, a three-dimensional image can be provided to a display screen 1450, such as a video monitor of an imaging system. For example, the display screen 1450 can selectively depict a three-dimensional live image/video feed obtained by the camera 1420. In various instances, the display screen 1450 can also selectively depict a three-dimensional rendering of the surgical site (e.g. of the visible tissue) based on surface mapping logic and the structured light pattern emitted from the emitter 1406 and detected by the camera 1420. In certain instances, the three-dimensional rendering of the visible tissue at the surgical site can be overlaid with the embedded critical structure 1401, for example. Additionally or alternatively, the distance d (FIG. 22) from the surgical device 1402 to the critical structure 1401 can be displayed on the display screen 1450.

In one instance, referring still to FIG. 23, the display screen 1450 can be configured to display an augmented color schematic 1452a of the critical structure 1401 with a color legend or key 1454a to indicate the distance d (FIG. 22) to the critical structure 1401 and/or portions thereof. For example, the key 1454a provides a spectrum of colors corresponding to linear distances or zones such as green, in which the surgical device 1402 is 15 mm-20 mm away from the critical structure 1401, yellow, in which the surgical device 1402 is 15 mm-10 mm away from the critical structure 1401, orange, in which the surgical device 1402 is 5 mm-10 mm away from the critical structure 1401, and red, in which the surgical device 1402 is 0 mm-5 mm away from the critical structure 1401. The different colors can correspond to different types of communication to the clinician. For example, green can mean "go" or "proceed", yellow can mean "slow down" or "proceed with caution", orange can mean "exercise extra caution", and red can mean "stop." In such instances, the critical structure 1401 can be depicted in one or more colors corresponding to the calculated distance and the related colors on the key 1454a depending on the proximity of the surgical device 1402 to portions thereof.

In various instances, the clinician can be alerted when the distance moves from one proximity zone to another along the spectrum of the key 1454a. For example, a first alert can be provided when the distance moves from the green zone to the yellow zone, a second alert can be provided when the distance moves from yellow zone to the orange zone, and a third alert can be provided when the distance moves from the orange zone to the red zone. The type of alert can vary depending on the proximity of the surgical device 1402 and/or the preprogrammed settings selected by the clinician. Similarly, in various aspects, the imaging system can alert the clinician when the surgical device 1402 is moved away from the critical structure 1401, such as when the critical structure 1401 is a target of the surgical device 1402.

In another instance, referring to FIG. 24, the display screen 1450 can be configured to display a black and white cross-hatched augmented schematic 1452b of the critical structure 1401 with a cross-hatching legend or key 1454b to indicate the distance d (FIG. 22) to the critical structure 1401 and/or portions thereof.

In certain instances, the distance d from the surgical device 1402 to the critical structure 1401 can be displayed along a proximity spectrum indicator that includes a plurality of ranges and/or zones corresponding to different distances. Different types of cross-hatching can correspond to different proximity zones, and the key 1454b can explain the significance of the different types of cross-hatching with respect to distances or proximity zones. The proximity spectrum can be defined by a spectrum of colors, a range of numerical values, and/or other differentiating symbols to indicate proximity, for example.

In various instances, the surgical visualization systems disclosed herein, such as the surgical visualization system 1400, for example, can be utilized to target a specific critical structure or portion thereof. For example, referring again to FIG. 22, the critical structure 1401 can be a structure that the surgical device 1402 is targeting. In one instance, the critical structure 1401 can be a location on a vessel that the clinician would like to dissect in order to remove a piece of tissue without compromising blood flow to other tissue. For example, the critical structure 1401 can be a location on a vessel that is downstream of a branch supplying blood to healthy tissue. In such instances, the downstream location on the vessel can be tagged and targeted by the surgical visualization system. Tagging of structures is further described in contemporaneously-filed U.S. patent application Ser. No. 16/128,193, titled SURGICAL VISUALIZATION AND MONITORING, for example, which is incorporated by reference herein in its entirety. Proximity spectrum indicators can be configured to track/monitor the approach of the surgical device 1402 to the targeted critical structure 1401.

Referring now to FIGS. 25 and 26, a surgical visualization system 1500 including a camera 1520 and surgical devices 1502a, 1502b, 1502c is shown. The camera 1520 includes an image sensor, as further described herein. The surgical visualization system 1500 can be similar to the surgical visualization system 100 (FIG. 1) and the surgical visualization system 1400 (FIGS. 22-24) in various aspects. For example, the surgical visualization system 1500 can be configured to identify one or more critical structures 1501 embedded below a surface 1505 of a tissue 1503, and to determine one or more distances with respect to the critical structure(s) 1501.

Similar to the surgical device 1402 (FIG. 22), one or more of the surgical devices 1502a, 1502b, 1502c can include an emitter configured to emit light waves. For example, the emitter(s) can be configured to emit a pattern of structured light. The pattern is configured to reflect off a surface, and the reflected light can be detected by a camera or sensor, such as the camera 1520. Based on the reflected pattern, a control circuit is configured to determine the contours of the surface 1505 and various distances with respect to the surface 1505. For example, the control circuit can generate a three-dimensional model of the surface 1505. Various control circuits are further described herein (e.g. see FIGS. 2 and 11).

Similar to the camera 1420 (FIG. 22), the camera 1520 is a three-dimensional camera, which includes a two-dimensional left-side lens, or sensor, 1508a, and a two-dimensional right-side lens, or sensor, 1508b. The lenses 1508a, 1508b are configured to detect the embedded critical structure 1501. For example, the left-side lens 1508a is configured to detect a two-dimensional view of the critical structure 1501 and the right-side lens 1508b is configured to detect another two-dimensional view of the critical structure 1501. The two-dimensional views obtained by the lenses 1508a, 1508b can be combined to create a three-dimensional view 1552 of the surgical site on a display screen 1550 (FIG. 26) of an imaging system. The display screen 1550 can be a video monitor, which provides a video feed of the surgical site and/or various additional data/information to the clinician intraoperatively. For example, the three-dimensional view 1552 on the display screen 1550 can depict the critical structure 1501 and the relative positions of the surgical devices 1502a, 1502b, 1502c overlaying a topographical surface map of the tissue 1503 from the structured light and surface mapping logic.

Moreover, in various instances, the distances $d_1$, $d_2$, and $d_3$ from the surgical devices 1502a, 1502b, 1502c, respectively, to the critical structure 1501 can be determined and/or approximated from the three-dimensional imaging of the surgical site, as further described herein. For example, the distance from each surgical device 1502a, 1502b, 1502c to the critical structure 1501 can be measured in two-dimensions and averaged, or otherwise computed/triangulated from known positions and/or distances.

The distances $d_1$, $d_2$, and $d_3$ are communicated to the display screen 1550 (e.g. a video monitor), which is configured to display the distances $d_1$, $d_2$, and $d_3$. For example, the distances $d_1$, $d_2$, and $d_3$ can be displayed in a color-coded format, as depicted in FIG. 26. More specifically, the distances $d_1$, $d_2$, and $d_3$ can be displayed along proximity spectrum indicators 1554a, 1554b, 1554c, respectively, that indicate distance. The proximity spectrum indicators 1554a, 1554b, 1554c include a spectrum of colors arranged along a bar, which can correspond to zones around the critical structure. In FIG. 26, the green zone corresponds to a distance of 15 mm-20 mm, a yellow zone corresponds to a distance of 15 mm-10 mm, an orange zone corresponds to a distance of 5 mm-10 mm, and a red zone corresponds to a distance of 0 mm-5 mm. The proximity zone can be indicated along the proximity spectrum indicators 1554a, 1554b, 1554c by a marker, such as an arrow 1556a, 1556b, 1556c, respectively, that identifies the zone for each surgical device 1502a, 1502b, 1502c, respectively.

Additionally or alternatively, the proximity spectrum indicators 1554a, 1554b, 1554c can include a range of numerical values and/or other symbols indicating proximity zones/distances. In certain instances, the proximity zones can be configurable or selectable for different critical structures and/or different surgical devices. For example, the proximity zones around a vessel can be different for an energy device and a stapler. Additionally, the proximity zone for an energy device can be different for a vein and an artery.

In various instances, the surgical visualization system 1500 is configured to provide an alert, warning, or other indication to the clinician when one of the surgical devices 1502a, 1502b, 1502c approaches a predefined range of positions/minimum distance limit/proximity zone around the critical structure 1501. The alerts can be provided at different critical distances based on the type of surgical device 1502a, 1502b, 1502c and the type of critical structure 1501.

In various instances, one or more of the surgical devices 1502a, 1502b, 1502c can be robotic tools. For example, a robotic system can control the surgical devices 1502a, 1502b, 1502c. In certain instances, a proximity zone around a critical structure can form a "keep out zone", and the robotic system can automatically control the surgical devices 1502a, 1502b, 1502c such that they stay out of the "keep out zone." If a clinician provides an input command to move the surgical device 1502a, 1502b, 1502c into a "keep out zone," an automated tool control motion can prevent the surgical device 1502a, 1502b, 1502c from entering the defined "keep out zone." In certain instances, such an automated tool control can be turned on/off, can be a default setting, and/or can be overcome by an override input by the clinician, for example.

Referring now to FIGS. 27-31, a surgical visualization system 1600 is shown. The surgical visualization system 1600 can be similar to the surgical visualization system 100 (FIG. 1) in various aspects. For example, the surgical visualization system 1600 can be configured to identify one or more critical structures 1601 embedded below a surface 1605 of a tissue 1603, and to determine one or more distances with respect to the surface 1605 and/or the critical structure(s) 1601. The surgical visualization system 1600 includes a detector or camera 1620 and a surgical device 1602. The camera 1620 includes an image sensor, as further described herein. The surgical visualization system 1600 is configured to provide a visible light rendition of the surgical field in a three-dimensional format. For example, an emitter can be configured to emit structured light, which can be converted to a topographical surface map. Three-dimensional images of the surgical field can be combined with overlays of hidden structures (i.e. critical structures) and/or a distance to the critical structure. An alert system can provide feedback to the clinician when a critical structure is located within a critical distance limit of the surgical device, as further described herein.

The surgical device 1602 includes an emitter 1606 configured to emit light waves. For example, the emitter 1606 can be configured to emit a tissue-penetrating infrared wavelength that is configured to penetrate the tissue 1603 and reach the critical structure 1601. The emitter 1606 can include a spectral light source, for example, which can be configured to emit hyperspectral, multispectral, and/or selective spectral waveforms, for example. The emitter 1606 can further emit a structured light pattern, which is detected by the camera 1620 to generate a topographical surface map of the surface 1605.

The camera 1620 also includes an image sensor or receiver 1608 configured to detect the light waves emitted from the emitter 1606 and reflected by the critical structure 1601. Spectral imaging logic can identify the critical structure based on the reflected light waves received by the image sensor 1608, as further described herein. In various instances, the detected critical structure 1601 can be schematically depicted as a line or other symbol on the three-dimensional rendering of the surface 1605 of the visible tissue 1603. For example, an approximate position of the critical structure 1601 can be conveyed to the clinician as a line on a three-dimensional surface map of the surface 1605. In certain instances, the image sensor 1608 is also configured to detect visible light, and can selectively record live images and/or a video feed of the surgical site and convey the images/video to an imaging system and/or display screen/monitor thereof.

The surgical visualization system 1600 is configured to determine a device-to-surface distance $d_2$ from a distal end 1612 of the surgical device 1602 to a tissue surface, a device-to-vessel distance $d_3$ from the distal end 1612 of the surgical device 1602 to a vessel below the tissue surface, and a surface-to-vessel distance/depth $d_4$ of the critical structure below the tissue surface, according to one or more distance determining methods and/or systems described herein. For example, the device-to-surface distance $d_2$ can be determined from surface mapping logic and the resultant surface map that is generated from the structured light pattern. Additionally or alternatively, the device-to-surface distance $d_2$ can be determined by a time-of-flight distance sensing system configured to detect a delay between an emitted wave and a received wave targeting the surface 1605 of the tissue 1603. In various instances, the device-to-surface distance $d_2$ can be the distance to the portion of the surface 1605 that is overlying an identified critical structure, such as the critical structure 1601. For example, the device-to-surface distance $d_2$ can be the distance from the distal end 1612 of the surgical device 1602 to an augmented line on the three-dimensional rendering of the surface 1605 nearest to the surgical device 1602. The device-to-vessel distance $d_3$ can be determined from NIR time-of-flight sensing of spectral waves received by the camera 1620 and/or one or more image sensors 1608. In other instances, the device-to-vessel distance $d_3$ can be determined from triangulation, three-dimensional cameras, and fluoroscopy illumination. In various instances, the surface-to-vessel depth $d_1$ can be computed and/or triangulated from real-time distances and/or dimensions obtained with spectral imaging, three-dimensional imaging and/or surface mapping data, determined by ultrasound, and/or dimensions obtained in preoperative scans, for example. Alternative distance determining systems are further disclosed herein.

The surgical visualization system 1600 also includes an imaging system, which can include the camera 1620 and a display screen 1650 (FIGS. 29-30). The imaging system can selectively display different information on the screen 1650. For example, the imaging system can include input controls, which can allow a clinician to select one or more views, dimensions, and/or other information on the display screen. An exemplary input control, a dial 1660, is shown in FIG. 28. The dial 1660 allows a clinician to select the device-to-surface distance $d_2$, the device-to-vessel distance $d_3$, or the surface-to-vessel distance $d_1$. For example, the clinician can rotate the dial 1660 between the different positions to select different distances. In other instances, the input control can comprise one or more inputs, buttons, toggles, switches, and/or touch screens, for example. In certain instances, two or more distances can be selected at the same time and/or the display screen 1650 can switch between different distances and/or views after a preset amount of time has elapsed.

Referring now to FIGS. 29-31, the display screen 1650 is configured to display different views 1652a, 1652b, 1652c of the surgical site based on the clinician's input. For example, depending on the position of the dial 1660, the display screen 1650 can display different views and/or information. The dial 1660 and position thereof can also be provided on the display screen 1650. In FIG. 29, the display screen 1650 depicts the first view 1652a in which the surface-to-vessel distance $d_1$ can be displayed and/or monitored. For example, in FIG. 29, the dial 1660 is in a first position in which the surface-to-vessel distance $d_1$ is selected. In such instances, the distance $d_1$ is monitored and relevant information is displayed on the screen 1650. For example, the distance $d_1$ can be displayed numerically and/or along a first proximity spectrum 1656a that indicates a warning when the distance $d_1$ is reduced below a predefined threshold, such as for thermal and/or force-related concerns, for example. The warning can be provided on the screen 1650 and/or via additional visual, auditory and/or haptic signals, for example. Additionally, the critical structure 1601, which is concealed to the naked eye, is schematically depicted via the augmented first view 1652a.

In FIG. 30, the display screen 1650 depicts the second view 1652b in which the device-to-surface distance $d_2$ can be displayed and/or monitored. For example, in FIG. 30, the dial 1660 is in a second position in which the device-to-surface distance $d_2$ is selected. In such instances, the distance $d_2$ is monitored and relevant information is displayed on the screen 1650. For example, the distance $d_2$ can be displayed numerically and/or along a second proximity spectrum 1656b that indicates a warning when the distance $d_2$ is reduced below a predefined threshold, such as for thermal and/or force-related concerns, for example. The warning can be provided on the screen 1650 and/or via additional visual, auditory and/or haptic signals, for example. When the distance to the tip of the surgical device 1602 is selected, the distance can be from a projected point of the tool to the tissue surface, which can be determined by a three-dimensional Cartesian coordinate system from the robot control arm.

The critical structure 1601, which is concealed to the naked eye, is identified with spectral imaging and schematically depicted via the augmented second view 1652b. In various instances, the augmented schematic of the critical structure 1601 can be toggled on and off and/or, as shown in FIG. 30, shown as a shadow/phantom background shape. For example, because the selected distance $d_2$ in FIG. 30 is not directly to the critical structure 1601, it can be desirable to show the critical structure 1601 as a shadow or hidden to avoid distracting the clinician and/or to focus the clinician's attention on the other selected information. In various instances, as described herein, the distance $d_2$ can be the distance to the augmented line on the surface 1605 representing the hidden critical structure 1601, and the hidden critical structure 1601 can be schematically depicted as a shadow and/or background image for context.

In FIG. 31, the display screen 1650 depicts the third view 1652c in which the device-to-vessel distance $d_3$ can be displayed and/or monitored. For example, in FIG. 31, the dial 1660 is in a third position in which the device-to-vessel distance $d_3$ is selected. In such instances, the distance $d_3$ is monitored and relevant information is displayed on the screen 1650. For example, the distance $d_3$ can be displayed numerically and/or along a third proximity spectrum 1656c that indicates a warning when the distance $d_3$ is reduced below a predefined threshold, such as for thermal and/or force-related concerns, for example. The warning can be provided on the screen 1650 and/or via additional visual, auditory and/or haptic signals, for example.

The critical structure 1601, which is concealed to the naked eye, is schematically depicted via the augmented third view 1652c. In various instances, an augmented schematic of the surface 1605 of the tissue 1603 can be toggled on and off and/or, as shown in FIG. 31, shown as a shadow/phantom shape. For example, because the selected distance $d_3$ is unrelated to the position of the surface 1605, it can be desirable to show the surface 1605 as a shadow or hidden to avoid distracting the clinician and/or to focus the clinician's attention on other information. In certain instances, the three-dimensional surface map can be generated from structured light and surface mapping logic, which can be utilized to selectively show the surface 1605 of the tissue 1603 on the display screen 1650, as further described herein.

The views and/or portions thereof in FIGS. 29-31 can be toggled on or off. In various instances, the surgical visualization system 1600 can operate without contrast agents added to any of the structures. Selective spectral imaging can allow the selectability of specific targets, which can be paired with a specific distance and proximity warning based on the identification of the critical structure (e.g. as a nerve, organ, ureter, vein, artery, or lymph node) and the margins or mechanical edges of tumors, for example.

When a surgical device is being manipulated around a surgical site, the clinician may want to know the position of the surgical device and/or "see" the surgical device relative to one of more other structures (e.g., surface tissue, hidden critical structures, other surgical devices etc.). However, the surgical device or a portion thereof can be obstructed from view during a surgical procedure. For example, tissue or another anatomical structure can be positioned between the clinician's view point (e.g. the camera) and the surgical device or a portion of the surgical device, such as an articulation joint and/or jaw, for example, which can block the clinician's view. In such instances, the clinician may be unable to visualize the surgical device or a portion thereof and may risk moving the surgical device too close to a critical structure. For example, a clinician may unintentionally maneuver a surgical stapler, dissector, energy device, and/or needle too close to the critical structure and risk dissecting or otherwise harming the critical structure.

In various instances, a surgical visualization system can allow a clinician to visualize a an obstructed/partially obstructed surgical device relative to a critical structure. For example, the surgical visualization system can be configured to identify the surgical device. In various instances, spectral imaging, such as hyperspectral, multispectral, or selective spectral imaging, for example, can be utilized to identify the surgical device. Other detection modalities include ultrasound, registered magnetic resonance imaging (MRI), and computerized tomography (CT) scans, for example. The surgical visualization system can also include an imaging system including a display that is operably configured to depict the identified surgical device with respect to anatomical structures and/or other surgical devices.

In such instances, the clinician can track the position of the surgical device relative to the critical structure even when the surgical device and/or the critical structure is obscured (or partially obscured) from view. Visualization of a hidden surgical device relative to a critical structure can allow the clinician to carefully and quickly maneuver the surgical device in the desired proximity of the critical structure. For example, a clinician can ensure a dissector stays a sufficient distance away from the critical structure (e.g. from an artery). In another example, a clinician can ensure a biopsy needle reaches one or more suitable locations within the critical structure (e.g. within a tumor).

Referring now to FIGS. 32 and 33, a surgical visualization system 1800 is shown. The surgical visualization system 1800 can be similar to the surgical visualization system 100 (FIG. 1) in many respects. For example, the surgical visualization system 1800 can be configured to identify one or more critical structures embedded in tissue or otherwise hidden from view, and to determine one or more distances with respect to the visible tissue and/or critical structure(s). The surgical visualization system 1800 includes a hyperspectral camera 1820, which comprises an image sensor, as further described herein. For example, the hyperspectral camera 1820 includes an emitter 1806 and a receiver 1808. The emitter 1806 is configured to emit a plurality of tissue-penetrating wavelengths. In various instances, the emitter 1806 can be configured to emit a plurality of hyperspectral, multispectral, or selective spectral waveforms, which are configured to penetrate tissue and reach one or more critical structures, such as a surgical device or another anatomical structure. For example, the emitter 1806 is configured to emit waveforms that penetrate the tissue 1803a and 1803b.

Identification of hidden anatomical structures, such as a nerve, a vessel, or a ureter, for example, is further described herein. Moreover, in addition to identifying a hidden anatomical structure, spectral imaging can be configured to detect metal, such as the metal portion of an end effector, a metal shaft, staples, and/or a metal band or plate, for example. In such instances, the surgical visualization system can further detect hidden surgical devices. For example, the receiver 1808 on the hyperspectral camera 1820 is configured to identify critical structures including surgical devices, such as a first device 1802a positioned through a first trocar 1810a and a second device 1802b positioned through a second trocar 1810b. The first device 1802a is a robotic grasper tool including an end effector 1812a, which is entirely hidden from the clinician's view by the tissue 1803a, which is a portion of the colon in this example, under which the end effector 1812a is positioned. The second device 1802b is a robotic stapling tool including an end effector 1812b, which is partially hidden from the clinician's view by the tissue 1803a. For example, the end effector 1812b is positioned to clamp the tissue 1803a and, thus, a first jaw is positioned above the tissue 1803a, and a second jaw is positioned below the tissue 1803a.

In certain instances, the receiver 1808 can identify the shaft of the devices 1802a, 1802b and/or the end effectors 1812a, 1812b, respectively, of the devices 1802a, 1802b. In one aspect, a clinician can select, or tag, the shaft or end effector 1812a, 1812b or another portion of the device 1802a, 1802b to track during a surgical procedure. For example, a clinician can select tracking of the shaft of one of the devices 1802a, 1802b to obtain information of where the side of the tool is with respect to other adjacent anatomy. Additionally or alternatively, the receiver 1808 can identify one or more anatomical structures, such as an artery 1801 embedded in tissue 1803b. Tagging of structures is further described in contemporaneously-filed U.S. patent application Ser. No. 16/128,193, titled SURGICAL VISUALIZATION AND MONITORING, for example, which is incorporated by reference herein in its entirety.

The receiver 1808 is configured to track the position of the critical structures (e.g. the end effectors 1812a, 1812b, and the artery 1801) intraoperatively. In various instances, the surgical visualization system 1800 is configured for use during a minimally invasive surgical procedure, such as the minimally invasive colorectal procedure depicted in FIG. 32. The surgical visualization system 1800 also includes an imaging system, which includes the camera 1820 and a display 1850 (FIG. 33). The positions of the critical structures can be conveyed to the clinician via the display 1850 of the imaging system.

Referring now to FIG. 33, the display 1850 is a monitor, which is configured to display a video feed of the surgical site in real-time. For example, images from the camera 1820 can be conveyed to the display 1850 intraoperatively to provide a live view of the surgical site to the clinician. Moreover, the view of the surgical site can be augmented with additional information including hidden critical structures and/or distances. The display 1850 shows the embedded artery 1801 and the surgical devices 1802*a*, 1802*b* including the hidden portions thereof augmented into a view of the surgical site.

In various instances, the display 1850 can also depict a three-dimensional rendering of certain anatomical structures at the surgical site. For example, the tissue 1803*a* (a portion of the colon), can be depicted on the display 1850. The rendering of the colon can be obtained via structured light and surface mapping logic, as further described herein. For example, the hyperspectral camera 1820 can further include a structured light source, which can emit a structured light pattern onto the tissue 1803*a* and/or the tissue 1803*b*, for example. Moreover, the hyperspectral camera 1820 can also include a receiver configured to detect the structured light pattern. Referring to the view in FIG. 33, the colon is shown as a shadow/background image, which was obtained from the structured light and surface mapping logic, and the critical structures (e.g. the end effectors 1812*a*, 1812*b*, and the artery 1801) identified with the spectral imaging system (e.g. hyperspectral camera 1820 and spectral imaging identification logic) overlay the colon on the display 1850.

The display 1850 also includes a proximity spectrum indicator 1856, which communicates the proximity of one or both of the surgical devices 1802*a*, 1802*b* to the artery 1801. In certain instances, the proximity spectrum indicator 1856 can display the proximity of the closest surgical device 1802*a*, 1802*b*. In other instances, the proximity of the closest surgical device 1802*a*, 1802*b* can be a default mode; however, the clinician can selectively pick another surgical device and/or anatomical structure. In still other instances, the proximity spectrum indicator 1856 can alternative and/or toggle between the different surgical devices 1802*a*, 1802*b*, or can include different spectrum indicators 1856 for the different surgical devices 1802*a*, 1802*b*.

The proximity spectrum indicator 1856 can utilize colors (e.g. red, yellow, green), dimensions, and/or other symbols to communicate the proximity of the surgical device 1802*a*, 1802*b* to the artery 1801. For example, proximity zones can be defined around the artery 1801, which can be assigned a color or range of colors. As the distance changes intraoperatively, a marker 1854 can move along the proximity spectrum indicator 1856 to convey the proximity zone in real time. Referring still the FIG. 33, the marker 1854 can move from the green zone, to the yellow zone, to the red zone as the proximity of the closest surgical device and the artery 1801 decreases, for example.

In various instances, the surgical visualization system 1800 is configured to provide an alert, warning, or other indication to the clinician when one of the surgical devices 1802*a*, 1802*b* approaches a predefined range of positions/minimum distance limit/proximity zone around the critical structure, such as the artery 1801. The alerts can be provided at different critical distances based on the type of surgical device 1802*a*, 1802*b* and the type of critical structure. In one instance, the surgical visualization system 1800 can provide a warning when the marker 1854 moves into the red zone.

The surgical visualization system 1800 is configured to determine one or more distances $d_a$ and $d_b$ from the end effectors 1812*a* and 1812*b*, respectively. For example, the surgical visualization system 1800 can utilize time-of-flight distance measurements to determine various distances from the camera 1820 (e.g. with targeted tissue-penetrating wavelengths to the surgical devices 1802*a*, 1802*b* and the artery 1801, as further described herein). Triangulation algorithms can then determine the relative distances between the structures, such as the distances $d_a$ and $d_b$, for example.

A surgical visualization system can be utilized during a biopsy. An ultrasound-assisted biopsy procedure is shown in FIG. 38, in which an ultrasound device 1920 is configured to emit ultrasound waves 1924 that are directed toward the surgical site. In this example, the ultrasound waves 1924 are directed toward a thyroid gland 1903 in order to identify the position of a nodule 1901, or tumor, within the thyroid gland 1903 so that a clinician can guide a biopsy needle 1902 toward the nodule 1901. In various instances, it can be desirable to take multiple samples within the nodule 1901 and to biopsy tissue from different locations within the nodule 1901. Ultrasound-assisted biopsies are further described in the article THYROID FINE NEEDLE ASPIRATION (FNA) BIOPSY, available at www.fairview.org/patient-education/90246.

In one aspect, a surgical visualization system including spectral imaging technology can be utilized during a biopsy procedure. Referring now to FIGS. 34-37, a surgical visualization system 2000 is shown. The surgical visualization system 2000 can be similar to the surgical visualization system 100 (FIG. 1) in many respects. For example, the surgical visualization system 2000 can be configured to identify one or more critical structures embedded in tissue or otherwise hidden from view, and to determine one or more distances with respect to the visible tissue and/or critical structure(s).

The surgical visualization system 2000 includes a hyperspectral camera 2020, which includes an image sensor, as further described herein. For example, the camera 2020 includes an emitter 2006 and a receiver 2008. The emitter 2006 is configured to emit a plurality of tissue-penetrating waves. In various instances, the emitter 2006 can be configured to emit a plurality of hyperspectral, multispectral, or selective spectral waveforms, which are configured to penetrate tissue and reach one or more critical structures, such as a needle 2002 and a tumor 2001. For example, the emitter 2006 is configured to emit waveforms that penetrate a surface 2005 of a tissue 2003 such as a thyroid. Given the different molecular composition of the needle 2002, which is usually comprised of metal and/or plastic, from tissue, spectral imaging can distinguish the embedded needle 2002 from the tissue 2003 and the tumor 2001 because the spectral signatures of these materials will be different. Moreover, as further described herein, spectral imaging can distinguish the different types of tissue (i.e., the thyroid 2003 and the tumor 2001 embedded therein). The surgical visualization system 2000 is configured to convey and/or determine the proximity of the aspirating needle 2002 to tissue (e.g. the tissue of the thyroid 2003) and/or a critical structure (e.g. the tumor 2001). For example, the surgical visualization system 2000 can determine the depth of the aspirating needle 2002 relative to tissue 2003 and a targeted critical structure (i.e., the tumor 2001) using spectral signature differences between the aspirating needle 2002, the tissue 2003, and the targeted tumor 2001. As such, the surgical visualization system 2000 can be utilized instead of the ultrasound device 1920 (FIG. 38).

The surgical visualization system 2000 also includes a structured light source and surface mapping logic, as further described herein. In one aspect, the camera 2020 includes the structured light source. For example, the emitter 2006 can be configured to selectively pulse between the spectral imaging waveforms and the structured light pattern. In certain aspects, the camera 2020 is also configured to detect the pattern of structured light on the surface 2005 of the tissue 2003. The surface mapping logic is configured to generate a three-dimensional model or rendering of the tissue surface 2005, which can be provided to an imaging system and overlaid with data from the spectral imaging system, as further described herein.

In FIG. 34, a tip 2012 of the needle 2002 is located a distance $d_1$ from the surface 2005 of an anatomical target, the tissue 2003, and a distance $d_2$ from the surface of the embedded tumor 2001. In FIG. 36, the tip 2012 of the needle 2002 is advanced into the tumor 2001 to a distance $d_2$ from the surface of the tumor 2001. The position of the needle 2002 relative to the tissue 2003 and the tumor 2001 is conveyed to an imaging system. For example, the surgical visualization system 2000 can include an imaging system including the camera 2020 and a display 2050 (FIGS. 35 and 37). The camera 2020 includes an image sensor, as further described herein. The positions of the identified structures (e.g. the tumor 2001 and the needle 2002) can be conveyed to the clinician via the display 2050.

The display 2050 is a monitor that is configured to display a video feed of the surgical site in real-time. For example, images from the camera 2020 can be conveyed to the display 2050 intraoperatively to provide a live view of the surgical site to the clinician. The view of the surgical site can be augmented with additional information including hidden critical structures and/or distances. For example, the display 2050 shows the embedded tumor 2001 and the needle 2002, including the portion of the needle 2002 that is hidden from the clinician's view by tissue.

In various instances, the display 2050 also depicts a three-dimensional rendering of certain anatomical structures at the surgical site. For example, the tissue 2003 is shown on the display 2050. The rendering of the anatomical target tissue 2003 can be obtained via structured light and surface mapping logic, as further described herein. For example, the hyperspectral camera 2020 can further include a structured light source, which can emit a structured light pattern onto the tissue 2003, for example. Moreover, the hyperspectral camera 2020 can include a receiver configured to detect the structured light pattern. Referring to the view in FIGS. 35 and 37, the tissue 2003 and the embedded critical structures (e.g. the needle 2002 and the tumor 2001) overlap in the view on the display 2050.

The display 2050 also includes proximity spectrum indicators 2056a, 2056b, which communicate the proximity of the needle 2002 to the surface 2005 of the tissue 2003 (distance $d_1$) and to the surface of the embedded tumor 2001 (distance $d_2$). For example, the proximity spectrum indicators 2056a, 2056b can define distance in positive and negative values from the surfaces. In FIG. 34, the needle 2002 is inside the tissue 2003 and outside the tumor 2001, thus, in FIG. 35, the proximity spectrum indicator 2056a indicates that the distance $d_1$ is a negative value and the proximity spectrum indicator 2056b indicates that the distance $d_2$ is a positive value. In FIG. 36, the needle 2002 is inside the tissue 2003 and inside the tumor 2001, thus, in FIG. 37, the proximity spectrum indicator 2056a indicates that the distance $d_1$ is a negative value and the proximity spectrum indicator 2056b indicates that the distance $d_2$ is also a negative value.

In various aspects, the proximity spectrum indicators 2056a, 2056b can include colors, numerical values or ranges, and/or other symbols to detect proximity. In certain instances, a single proximity spectrum indicator can alternate and/or toggle between the different distances $d_1$ and $d_2$ and/or a clinician can select one or more distances to display.

In various instances, the surgical visualization system 2000 is configured to provide an alert, warning, or other indication to the clinician when the needle 2002 approaches a predefined range of positions, a minimum distance limit, and/or a proximity zone around the tumor 2001 and/or a depth within the tissue 2003.

The surgical visualization system 2000 is configured to determine one or more distances with time-of-flight sensor systems (e.g. with targeted wavelengths to the surface 2005, the needle 2002, and the tumor 2001, as further described herein). Furthermore, triangulation algorithms can determine the relative distances between the structures, such as the distances $d_1$ and $d_2$, for example.

In certain instances, the biopsy procedure shown in FIGS. 34-37 can be augmented with contact-based ultrasound guidance, for example, as shown in FIG. 38.

Various surgical visualization systems disclosed herein are configured to identify one or more critical structures embedded in tissue or otherwise hidden from view, and determine one or more distances with respect to the visible tissue and/or the critical structure(s). In certain instances, the critical structure can be a surgical device, such as a grasper, a dissector, a stapler, a staple, a staple row/line, a circular stapler, a circular stapler anvil, a gastric bougie, or a hernia tack/clip, for example. During a surgical procedure, it can be desirable to track the position of these critical structures. For example, a subsequent step in a surgical procedure can depend on the position of a critical structure that was implanted and/or moved during an earlier step.

As one example, during a lower anterior resection (LAR) of the colon, the clinician may want to identify and track the staple lines along the ends of the colon before effecting anastomosis of the ends. Referring to the exemplary LAR procedure in FIGS. 39-41, a colon 2270 can be transected into two portions, a first colon portion 2272 and a second colon portion 2274, to remove an intermediate portion, such as a cancerous tumor, for example. Rows of staples can seal the terminated ends of the first colon portion 2272 and/or the second colon portion 2274 prior to resection.

A circular stapler 2202 can be utilized to resect the first and second colon portions 2272 and 2274. As shown in FIG. 39, the circular stapler 2202 is positioned in the first colon portion 2272 and an anvil 2204 is positioned in the second colon portion 2274. For example, the circular stapler 2202 can be inserted transanally and the anvil 2204 can be positioned through an incision. The anvil 2204 and the circular stapler 2202 are brought into alignment and the anvil 2204 can be secured to the circular stapler 2202, as shown in FIG. 40. For example, a trocar 2206 (FIG. 39) of the circular stapler 2202 can be positioned within a shaft 2208 (FIG. 39) of the anvil 2204. Thereafter, referring to FIG. 41, the circular stapler 2202 fires a knife and staples against the anvil 2204 to form a sealed path between the first colon portion 2272 and the second colon portion 2274. LAR procedures are further described in OPEN TECHNIQUE FOR LOW ANTERIOR RESECTION, available at abdominalkey.com/open-technique-for-low-anterior-resection.

Proper alignment of the circular stapler 2202 and the anvil 2204 is important for sealing the first colon portion 2272 and the second colon portion 2274. Therefore, it can be helpful to visualize the circular stapler 2202 and/or the anvil 2204 during the procedure. It can also be helpful to visualize the position of the staple lines and determine one or more distances relative thereto. For example, a clinician may want to track the proximity of the circular stapler 2202, the anvil 2204, and one or more staple lines (and, thus, the severed ends of the colon 2270) during the procedure to facilitate alignment and/or positioning of the devices. A surgical visualization system, as disclosed herein, can be utilized to image, visualize, and track the positions of the circular stapler 2202, the trocar 2206, and the anvil 2204, as well as the position of the trocar 2206 with respect to a desired exit point of the colon 2270, for example.

Referring now to FIGS. 42-45, a surgical visualization system 2300 is depicted. The surgical visualization system 2300 can be similar to the surgical visualization system 100 (FIG. 1) in many respects. For example, the surgical visualization system 2300 can be configured to identify one or more critical structures embedded in tissue or otherwise hidden from view, and to determine one or more distances with respect to the visible tissue and/or critical structure(s). The surgical visualization system 2300 includes a hyperspectral camera 2320 including an image sensor, as further described herein. For example, the camera 2320 includes an emitter 2306 and a receiver 2308. The emitter 2306 is configured to emit a plurality of tissue-penetrating waves. In various instances, the emitter 2306 can be configured to emit a plurality of hyperspectral, multispectral, or selective spectral waveforms, which are configured to penetrate tissue and reach one or more critical structures, such as a surgical device or another anatomical structure. For example, the emitter 2306 is configured to emit waveforms that penetrate a colon 2303. The surgical visualization system 2300 also includes a structured light source.

Identification of hidden anatomical structures, such as a nerve, a vessel, or a ureter, for example, and surgical devices, such as a surgical end effector, shaft, or staple, for example, is further described herein. For example, the receiver 2308 on the hyperspectral camera 2320 is configured to identify critical structures including surgical devices, such as a first device 2302a and a second device 2302b. The first device 2302a is a robotic grasper tool and the second device 2302b is a robotic stapling tool. In other instances, the devices 2302a, 2302b can be handheld surgical instruments, and may be used in a laparoscopic procedure, for example. In certain instances, the receiver 2308 can identify the shaft and/or the end effectors of the devices 2302a, 2302b. Additionally, the receiver 2308 on the hyperspectral camera 2320 is configured to identify staple lines 2380a, 2380b in the colon 2303. In one aspect, a clinician can select, or tag, a portion of a critical structure (e.g. a surgical device 2302a, 2302b and/or staple lines 2380a, 2380b) to track during a surgical procedure. Tagging of structures is further described in contemporaneously-filed U.S. patent application Ser. No. 16/128,193, titled SURGICAL VISUALIZATION AND MONITORING, for example, which is incorporated by reference herein in its entirety.

The receiver 2308 is configured to track the position of the critical structures (e.g. the surgical devices 2302a, 2302b, and the staple lines 2380a, 2380b) intraoperatively. In various instances, the surgical visualization system 2300 is configured for use during an LAR procedure, as shown in FIGS. 39-41. In such a procedure, it can be helpful to visualize an obscured, or partially obscured, surgical device 2302a, 2302b relative to a staple line 2380a, 2380b that may also be obscured or partially obscured. For example, one or more critical structures can be obscured by fat or mesentery. The surgical visualization system 2300 also includes an imaging system, which includes the camera 2320 and a display 2350 (FIGS. 43 and 45). The relative positions of the surgical devices 2302a, 2302b and the staple lines 2380a, 2380b can be conveyed to the clinician via the display 2350 of the imaging system.

Referring now to FIG. 43, the display 2350 is a monitor, which is configured to display a video feed of the surgical site in real-time. For example, images from the camera 2320 can be conveyed to the display 2350 intraoperatively to provide a live view of the surgical site to the clinician. Moreover, the view of the surgical site can be augmented with additional information including hidden critical structures and/or distances. The display 2350 shows the obscured staple lines 2380a, 2380b and the surgical devices 2302a, 2302b including the hidden portions thereof augmented into a view of the surgical site.

In various instances, the display 2350 also depicts a three-dimensional rendering of certain anatomical structures at the surgical site. For example, the colon 2303 can be depicted on the display 2350. The rendering of the colon 2303 and movement thereof can be obtained via structured light and surface mapping logic, as further described herein. For example, the hyperspectral camera 2320 can further include the structured light source, which can emit a structured light pattern onto the colon 2303, for example. Moreover, the hyperspectral camera 2320 can also include a receiver configured to detect the structured light pattern. In other instances, a separate device can emit and/or detect the structured light pattern. Referring to the view in FIGS. 43 and 45, the colon 2303 is shown as a shadow/background image, which was obtained from the structured light and surface mapping logic, and the critical structures (e.g. the surgical devices 2302a, 2302b and the staples lines 2380a, 2380b) identified with the spectral imaging overlay the three-dimensional rendering of the colon 2303 on the display 2350.

The display 2350 also includes a proximity spectrum indicator 2356, which communicates the proximity of one or both of the surgical devices 2302a, 2302b to one or both of the staple lines 2380a, 2380b. In various instances, the clinician can selectively pick a staple line 2380a, 2380b and a surgical device 2302a, 2302b to track and monitor on the proximity spectrum indicator 2356 and/or show on the display 2350. In other instances, the proximity spectrum indicator 2356 can alternate and/or toggle between the different surgical devices 2302a, 2302b and/or staple lines 2380a, 2380b or can include different spectrum indicators 2356 for the different surgical devices 2302a, 2302b and staple lines 2380a, 2380b. In certain instances a tagged staple line 2380a, 2380b can be tracked by the camera 2320 and remain visible on the display 2350, for example.

The proximity spectrum indicator 2356 can utilize colors (e.g. red, yellow, green), dimensions, and/or other symbols to communicate the proximity of the surgical device 2302a, 2302b to the staple line 2380a, 2380b. For example, proximity zones can be defined around the staple lines 2380a, 2380b, which can be assigned a color or range of colors. As the distance changes intraoperatively, a marker 2354 can move along the proximity spectrum indicator 2356 to convey the proximity zone in real time. Referring still to FIGS.

43 and 45, the marker 2354 can move from the green zone, to the yellow zone, to the red zone as the proximity decreases, for example.

In various instances, the surgical visualization system 2300 is configured to provide an alert, warning, or other indication to the clinician when one of the surgical devices 2302a, 2302b approaches a predefined range of positions, a minimum distance limit, and/or a proximity zone around the staple line 2380a, 2380b. The alerts can be provided at different critical distances based on the type of surgical device 2302a, 2302b. In one instance, the surgical visualization system 2300 can provide a warning when the marker 2354 moves into the red zone.

The surgical visualization system 2300 is configured to determine one or more distances from the surgical devices 2302a and 2302b, respectively. For example, the surgical visualization system 2300 can utilize time-of-flight distance measurements to determine various distances from the camera 2320 (e.g. with targeted wavelengths to the surgical devices 2302a, 2302b and the staple lines 2380a, 2380b, as further described herein). Triangulation algorithms can then determine the relative distances between the structures, for example.

In certain instances, a robotic system can be configured to autonomously track to the tagged staple line 2380a, 2380b as if to grasp it and position the colon for a subsequent surgical step, such as anastomosis. For example, the robotic system can automatically move to a position a preset distance away from the staple line 2380a, 2380b and/or above the staple line 2380a, 2380b. Upon automatically moving into proximity with the staple lines 2380a, 2380b, the clinician at the robotic console can further position the surgical tool via control at a command station/console.

Anastomosis of the colon 2303 is shown in FIGS. 44 and 45, for example. A surgical device 2302 comprising a circular staple 2302c and an anvil 2302d for anastomosis of the colon 2303 is illustrated in FIG. 44. For example, the robotic system can control the surgical device 2302a to grab the staple line 2380a and draw the staple line 2380a, with the anvil 2302d of the surgical device 2302 toward the circular stapler 2302c. In such instances, the hyperspectral camera 2320 is configured to detect the circular stapler 2302c, which is hidden within a lower portion of the colon 2303, and the anvil 2302d, which is hidden with an upper portion of the colon 2303. In certain instances, visualization of the anvil 2302d and the circular stapler 2302c can facilitate the alignment of the anvil 2302d with a trocar 2312 of the circular stapler 2302c.

Referring now to FIG. 45, the display 2350 for the surgical visualization system 2300 is shown. The display 2350 shows the obscured staple lines 2380a, 2380b, the surgical device 2302a, circular stapler 2302c, anvil 2302d, and another grasper device 2302e, including the hidden portions thereof, overlaid on a surface map of the visible tissue of the colon 2303. The display 2350 is further augmented with the distance $d_1$ from the anvil 2302d to the first staple line 2380a and the distance $d_2$ from the anvil 2302d to the trocar 2312 of the circular stapler 2302c.

The surgical visualization system 2300 can be employed to see the surgical device 2302 (i.e., the circular stapler 2302c and anvil 2302d) within the colon 2303 when viewed from a laparoscope. In various instances, the clinician can toggle visibility of the surgical device 2302 or other surgical devices on or off. When the surgical device 2302 is visualized, the clinician is able to see the position of the circular stapler 2302c, the trocar 2312, and the anvil 2302d. Additionally, the clinician can visualize the position of the trocar 2312 with respect to the desired exit point from the colon 2303.

Referring now to FIG. 46, a stomach 2403 is shown with a surgical device, more specifically a bougie 2402, positioned therein. The bougie 2402 is a surgical device, typically comprised of a flexible or compliant body 2412. The bougie 2402 can also include one or more bands 2414a, 2414b, 2414c, 2414d, 2414e, 2414f, 2414g, which can be comprised of rigid plastic or metal. During a sleeve gastrectomy, the bougie 2402 can be positioned in the stomach 2403 along the lesser curvature of the stomach 2403, and an adjacent portion of the stomach, typically the fundus 2405, can be removed. For example, a line of staples 2416 can dissect the stomach 2403 and remove the fundus 2405 from the remainder of the stomach 2403.

Referring now to FIG. 47, a stapling step of a sleeve gastrectomy is shown. In the stapling step, a linear stapler 2502a and a grasper 2502b are effecting the tissue 2503 of the stomach. The stapler 2502a and the grasper 2502b can be robotic tools, for example, during a robotic surgical procedure. A critical structure 2501, such as the pylorus, is at least partially hidden by the tissue 2503. Moreover, a bougie 2512 is positioned in the tissue 2503 of the stomach. In various instances, the surgeon may want to know the position of the linear stapler 2502a, the grasper 2502b, and/or the bougie 2512 relative to the critical structure 2501. For example, it can be important to space the bougie 2512 a minimum distance a from the critical structure 2501, such as at least 5 cm from the pylorus, for example. In such instances, the critical structure 2501 constitutes an anatomical landmark for positioning of the bougie 2512. In various instances, detectable critical structures, such as the critical structure 2501 and/or the bougie 2512, for example, can act as anatomical landmarks for positioning of other surgical devices. Other distances can also be monitored and/or visualized to ensure appropriate positioning of the bougie 2512 relative to various anatomical structures. For example, it can be important to position the linear stapler 2502a an appropriate distance from the bougie 2512 for proper sizing of the gastric sleeve while preventing undue strain on the staples. Gastric sleeve procedures are further described in the article "Sleeve Gastrectomy Surgical Assistive Instrument for Accurate Remnant Stomach Volume", ASME, J. Med. Devices, 2010; Vol. 4, Issue 2, which is incorporated by reference herein in its entirety, and is available at medicaldevices.asmedigitalcollection.asme.org/article.aspx?articleid=1474028. Gastric sleeve procedures are further described at aischannel.com/society/main-steps-to-perform-a-sleeve-gastrectomy/.

Referring now to FIGS. 48 and 49, a surgical visualization system 2600 is depicted. The surgical visualization system 2600 can be similar to the surgical visualization system 100 (FIG. 1) in many respects. For example, the surgical visualization system 2600 can be configured to identify one or more critical structures embedded in tissue or otherwise hidden from view, and to determine one or more distances with respect to the visible tissue and/or critical structure(s). In particular, the surgical visualization system 2600 is configured to allow visualization of a hidden bougie 2612 located within a stomach 2603 during a gastric sleeve procedure. The bougie 2612 includes a flexible, inflatable body or sleeve 2614 and bands 2616. In other instances, the bougie 2612 can have more than or less than the five bands 2616 shown in FIG. 48. The bands 2616 are comprised of a different material than the body 2614. As further described herein, spectral imaging can be configured to identify the different material and, thus, the position of the bougie 2612 even when the bougie 2612 is hidden within the stomach 2603. For example, the bougie 2612 is comprised of optically different material at key segments, which can be detected with spectral imaging.

The surgical visualization system 2600 includes a hyperspectral camera 2620 including an image sensor, as further described herein. For example, the camera 2620 can include an emitter 2606 and a receiver 2608. The camera 2620 can be utilized during a laparoscopic procedure to image a surgical site. The emitter 2606 is configured to emit a plurality of tissue-penetrating waves. In various instances, the emitter 2606 can be configured to emit a plurality of hyperspectral, multispectral, or selective spectral waveforms, which are configured to penetrate tissue and reach one or more critical structures, such as a surgical device or another anatomical structure. For example, the emitter 2606 is configured to emit waveforms that penetrate the stomach 2603. The surgical visualization system 2600 can also include a structured light source and receiver/image sensor 2068, which can be configured to determine the surface topography of the stomach 2603.

Identification of hidden anatomical structures, such as a nerve, a vessel, or a ureter, for example, and surgical devices, such as a surgical end effector, shaft, or staple, for example, is further described herein. For example, the receiver 2608 on the hyperspectral camera 2620 is configured to identify and track critical structures including surgical devices, such as the bougie 2612, the body 2614, and the bands 2616, as well as surgical tools, such as a linear stapler 2602.

The surgical visualization system 2600 also includes an imaging system, which includes the camera 2620 and a display 2650 (FIG. 49). The relative positions of the linear stapler 2602 and the bougie 2612 can be conveyed to the clinician via the display 2650 of the imaging system.

Referring now to FIG. 49, the display 2650 is a monitor, which is configured to display a video feed of the surgical site in real-time. For example, images from the camera 2620 can be conveyed to the display 2650 intraoperatively to provide a live view of the surgical site to the clinician. Moreover, the view of the surgical site can be augmented with additional information including hidden critical structures and/or distances. The display 2650 shows the obscured bougie 2612 augmented into a view of the surgical site. In various instances, visualization of an obscured critical structure, such as the bougie 2612, can be toggled on and off by a clinician. For example, the bougie 2612 can be depicted as a shadow in a default view and can be selectively removed from the display 2650 by a specific user input.

In various instances, the display 2650 also depicts a three-dimensional rendering of certain anatomical structures at the surgical site. For example, the stomach 2603 can be depicted on the display 2650. The rendering of the stomach 2603 can be obtained via structured light and surface mapping logic, as further described herein. Referring to the view in FIG. 49, the stomach 2603 is shown as a shadow/background image, which was obtained from the structured light and surface mapping logic, and the critical structures (e.g. the bougie 2612 as well as the linear stapler 2602) overlay the background. In other words, the spectral images of hidden structures are integrated with the three-dimensional representation of the stomach 2603.

The surgical visualization system 2600 is configured to determine one or more distances from the linear stapler 2602 and/or the bougie 2612 to a critical structure, such as a pylorus, i.e. the opening from the stomach 2603 into the small intestines. The surgical visualization system 2600 can utilize time-of-flight distance measurements to determine various distances from the camera 2620 (e.g. with targeted wavelengths to the surgical devices and/or anatomical structures, as further described herein). Triangulation algorithms can then determine the relative distances between the structures, for example. In various instances, an alert can be provided when the distance meets a threshold value and/or range, as further described herein.

In various instances, the different materials of the bougie 2612 can aid in positioning of the linear stapler 2602. For example, in certain gastric sleeve procedures, haptics can provide feedback to the clinician regarding the placement of the linear stapler 2602. For example, a clinician can palpate the stomach 2603 to determine the position of the bougie 2612. However, in robotic applications, a clinician may be unable to sufficiently evaluate the position of the bougie 6212 based on haptics/tactile feedback. Visualization of the bougie 2612 can provide a replacement and/or supplement to haptics. For example, the surgical visualization system 2600 is configured to determine the distance from the distal end of the linear stapler 2602 to the bougie 2612, which can assist the robotic system in positioning the various medical devices. Moreover, the distance(s) and/or position(s) can be conveyed to the clinician by an imaging system, as further described herein.

In various aspects, a surgical visualization system can be configured to identify a metallic fastener, such a clip, for example. For example, a surgical clip can be embedded in tissue (e.g. placed on a vein or artery to occlude it) during a surgical procedure. Firing staples against a surgical clip can affect the resultant firing motion. For example, a surgical clip between the jaws of an end effector can prevent the end effector from uniformly clamping the tissue and/or can jam a closure beam, firing member, and/or cutting element. Additionally, if staples are fired against the surgical clip, the staples can misfire and/or become deformed. In such instances, the staple line may result in an imperfect seal. The various surgical visualization systems disclosed herein can identify a surgical clip and, in various instances, notify a clinician when the surgical clip is positioned too close to a surgical device (e.g. within or near a transection location).

Referring now to FIGS. 50 and 51, a surgical visualization system 2700 is shown. The surgical visualization system 2700 can be similar to the surgical visualization system 100 (FIG. 1) in many respects. For example, the surgical visualization system 2700 can be configured to identify one or more critical structures embedded in tissue or otherwise hidden from view, and to determine one or more distances with respect to the visible tissue and/or critical structure(s). In particular, the surgical visualization system 2700 is configured to allow visualization of a hidden clip 2712 within tissue 2703 during a surgical procedure. As further described herein, spectral imaging can be configured to identify the material of the clip 2712 and, thus, the position of the clip 2712 even when the clip 2712 is hidden from view.

The surgical visualization system 2700 includes a hyperspectral camera 2720 including an image sensor, as further described herein. For example, the camera 2720 includes an emitter 2706 and a receiver 2708. The camera 2720 can be utilized during a laparoscopic procedure to image a surgical site. The emitter 2706 is configured to emit a plurality of tissue-penetrating waves. In various instances, the emitter 2706 can be configured to emit a plurality of hyperspectral, multispectral, or selective spectral waveforms, which are configured to penetrate tissue and reach one or more critical structures, such as a surgical device or another anatomical structure. For example, the emitter 2706 is configured to emit waveforms that penetrate the tissue 2703. The surgical visualization system 2700 also includes a structured light source, which can be configured to determine the surface topography of the tissue 2703.

Identification of hidden anatomical structures, such as a nerve, a vessel, or a ureter, for example, and surgical devices, such as a surgical end effector, shaft, or staple, for example, is further described herein. For example, the receiver 2708 on the hyperspectral camera 2720 is configured to identify and track critical structures including anatomical structures, such as the vessel 2701, for example, surgical devices, such as the clip 2712, for example, as well as surgical tools, such as a linear stapler 2702a and a grasper 2702b.

The surgical visualization system 2700 also includes an imaging system, which includes the camera 2720 and a display 2750 (FIG. 51). The relative positions of the surgical devices 2702a, 2702b, the clip 2712, and the vessel 2701, can be conveyed to the clinician via the display 2750 of the imaging system.

Referring now to FIG. 51, the display 2750 is a monitor, which is configured to display a video feed of the surgical site in real-time. For example, images from the camera 2720 can be conveyed to the display 2750 intraoperatively to provide a live view of the surgical site to the clinician. Moreover, the view of the surgical site can be augmented with additional information including hidden critical structures and/or distances. The display 2750 shows the obscured clip 2712 augmented into a view of the surgical site. In various instances, visualization of an obscured critical structure, such as the clip 2712, can be toggled on and off by a clinician. For example, the clip 2712 can be depicted as a shadow in a default view and can be selectively removed from the view on the display 2750 by a specific user input.

In various instances, the display 2750 also depicts a three-dimensional rendering of certain anatomical structures at the surgical site. For example, the tissue 2703 can be depicted on the display 2750. The rendering of the tissue 2703 can be obtained via structured light and surface mapping logic, as further described herein. Referring to the view on the display 2750 in FIG. 51, the tissue 2703 is shown as a shadow/background image, which was obtained from the structured light and surface mapping logic, and the critical structures (e.g. the clip 2712, the vessel 2701, and the surgical devices 2702a, 2702b) identified with the spectral imaging overlay the background. In other words, the spectral images of hidden structures are integrated with the three-dimensional representation of the tissue 2703.

The surgical visualization system 2600 is configured to determine one or more distances from the critical structures. For example, the proximity of the surgical devices 2702a, 2702b relative to the clip 2712 can be tracked. The surgical visualization system 2700 can utilize time-of-flight distance measurements to determine various distances from the camera 2720 (e.g. with targeted wavelengths to the surgical devices and/or anatomical structures, as further described herein). Triangulation algorithms can then determine the relative distances between the structures, for example.

As shown in FIG. 50, the clip 2712 is positioned between opposing jaws of the linear stapler 2702a. In such instances, the clip 2712 can be within a proximity zone of the linear stapler 2702a, which can be defined by a minimum distance between the linear stapler 2702a and the clip 2712. In various instances, the proximity zone can depend on the surgical device and/or step of the surgical procedure. Because the clip 2712 is within the proximity zone of the linear stapler 2702a, the display 2750 is configured to provide an alert or warning to the clinician. The alert can be communicated as an exclamation point or other symbol on the screen and/or with flashing, lights, and/or sounds, for example. In certain instances, the warning can be communicated along a proximity spectrum indicator 2756, for example.

Similarly, the surgical visualization system 2700 can be configured to detect additional fasteners, such as another clip, tack, or staple, for example, and to track the fastener relative to a surgical device or portion thereof, such as the end effector or shaft of the surgical device, for example. Referring now to FIG. 52, a laparoscopic hernia repair procedure is shown. During such a procedure, surgical tacks 2812 can be used to secure a surgical mesh 2814 to a tissue 2803, such as an abdominal wall. For example, the surgical mesh 2814 can be secured to an abdominal wall to prevent the intestines from protruding into the abdominal wall.

In various instances, a surgical visualization system can be configured to identify the surgical tacks 2812 to ensure the tacks 2812 do not damage a critical structure and/or are not positioned within a critical proximity zone relative to the critical structure. Referring again to FIG. 52, the surgical visualization system can be configured to identify the surgical tacks 2812, the mesh 2814, a surgical device, and one or more anatomical structures, such as a hernia 2801 on the intestines. As described herein, the surgical visualization system can utilize spectral imaging to identify one or more structures in combination with structured light to generate a three-dimensional representation of the tissue, such as the intestines within the abdomen cavity. In certain instances, the system can provide depth confirmation of the tack 2812 via the hyperspectral signature difference of the tack 2812, the tissue 2803, the hernia 2801, and the mesh 2814. In certain instances, the surgical visualization system can provide visibility of the hidden mesh 2814, for example, for joining with the tissue 2803 via the tack 2812. The various surgical visualization systems disclosed herein can identify a hernia tack and, in various instances, notify a clinician when the surgical tack is positioned too close to a surgical device and/or critical structure.

Example Clinical Applications

Various surgical visualization systems disclosed herein may be employed in one or more of the following clinical applications. The following clinical applications are non-exhaustive and merely illustrative applications for one or more of the various surgical visualization systems disclosed herein.

A surgical visualization system, as disclosed herein, can be employed in a number of different types of procedures for different medical specialties, such as urology, gynecology, oncology, colorectal, thoracic, bariatric/gastric, and hepato-pancreato-biliary (HPB), for example. In urological procedures, such as a prostatectomy, for example, the ureter may be detected in fat or connective tissue and/or nerves may be detected in fat, for example. In gynecological oncology procedures, such as a hysterectomy, for example, and in colorectal procedures, such as a low anterior resection (LAR) procedure, for example, the ureter may be detected in fat and/or in connective tissue, for example. In thoracic procedures, such as a lobectomy, for example, a vessel may be detected in the lung or in connective tissue and/or a nerve may be detected in connective tissue (e.g., an esophagostomy). In bariatric procedures, a vessel may be detected in fat. In HPB procedures, such as a hepatectomy or pancreatectomy, for example, a vessel may be detected in fat (extrahepatic), in connective tissue (extrahepatic), and the bile duct may be detected in parenchyma (liver or pancreas) tissue.

In one example, a clinician may want to remove an endometrial myoma. From a preoperative magnetic resonance imaging (MRI) scan, the clinician may know that the endometrial myoma is located on the surface of the bowel. Therefore, the clinician may want to know, intraoperatively, what tissue constitute a portion of the bowel and what tissue constitutes a portion of the rectum. In such instances, a surgical visualization system, as disclosed herein, can indicate the different types of tissue (bowel versus rectum) and convey that information to a clinician via an imaging system. Moreover, the imaging system can determine and communicate the proximity of a surgical device to the select tissue. In such instances, the surgical visualization system can provide increased procedural efficiency without critical complications.

In another example, a clinician (e.g. a gynecologist) may stay away from certain anatomic regions to avoid getting too close to critical structures and, thus, the clinician may not remove all of the endometriosis, for example. A surgical visualization system, as disclosed herein, can enable the gynecologist to mitigate the risk of getting too close to the critical structure such that the gynecologist can get close enough with the surgical device to remove all the endometriosis, which can improve the patient outcomes (democratizing surgery). Such a system can enable the surgeon to "keep moving" during the surgical procedure instead of repeatedly stopping and restarting in order to identify areas to avoid, especially during the application of therapeutic energy such as ultrasonic or electrosurgical energy, for example. In gynecological applications, uterine arteries and ureters are important critical structures and the system may be particularly useful for hysterectomy and endometriosis procedures given the presentation and/or thickness of tissue involved.

In another example, a clinician may risk dissection of a vessel at a location that is too proximal and, thus, which can affect blood supply to a lobe other than the target lobe. Moreover, anatomic differences from patient to patient may lead to dissection of a vessel (e.g. a branch) that affects a different lobe based on the particular patient. A surgical visualization system, as disclosed herein, can enable the identification of the correct vessel at the desired location, which enables the clinician to dissect with appropriate anatomic certainty. For example, the system can confirm that the correct vessel is in the correct place and then the clinician can safely divide the vessel.

In another example, a clinician may make multiple dissections before dissecting at the best location due to uncertainty about the anatomy of the vessel. However, it is desirable to dissect in the best location in the first instance because more dissection can increase the risk of bleeding. A surgical visualization system, as disclosed herein, can minimize the number of dissections by indicating the correct vessel and the best location for dissection. Ureters and cardinal ligaments, for example, are dense and provide unique challenges during dissection. In such instances, it can be especially desirable to minimize the number of dissections.

In another example, a clinician (e.g. a surgical oncologist) removing cancerous tissue may want to know the identification of critical structures, localization of the cancer, staging of the cancer, and/or an evaluation of tissue health. Such information is beyond what a clinician sees with the "naked eye". A surgical visualization system, as disclosed herein, can determine and/or convey such information to the clinician intraoperatively to enhance intraoperative decision making and improve surgical outcomes. In certain instances, the surgical visualization system can be compatible with minimally invasive surgery (MIS), open surgery, and/or robotic approaches using either an endoscope or exoscope, for example.

In another example, a clinician (e.g. a surgical oncologist) may want to turn off one or more alerts regarding the proximity of a surgical tool to one or more critical structure to avoid being overly conservative during a surgical procedure. In other instances, the clinician may want to receive certain types of alerts, such as haptic feedback (e.g. vibrations/buzzing) to indicate proximity and/or or "no fly zones" to stay sufficiently far away from one or more critical structures. A surgical visualization system, as disclosed herein, can provide flexibility based on the experience of the clinician and/or desired aggressiveness of the procedure, for example. In such instances, the system provides a balance between "knowing too much" and "knowing enough" to anticipate and avoid critical structures. The surgical visualization system can assist in planning the next step(s) during a surgical procedure.

EXAMPLES

Various aspects of the subject matter described herein are set out in the following numbered examples.

Example 1

A surgical visualization system comprising a display screen, a surgical device configured to emit a structured light pattern onto a surface, an image sensor configured to identify a structure embedded below the surface, and a control circuit in signal communication with the image sensor. The control circuit is configured to receive imaging data indicative of the structured light pattern on the surface, generate a three-dimensional digital representation of the surface based on the imaging data, obtain an image of the structure and the surgical device from the image sensor, overlay the image of the structure and the surgical device with the three-dimensional digital representation of the surface on the display screen, and determine a distance from the surgical device to the structure from the image.

Example 2

The surgical visualization system of Example 1, further comprising an emitter configured to emit spectral light in a plurality of wavelengths capable of penetrating the surface and reaching the structure, wherein the image sensor is configured to detect reflected spectral light, and wherein the control circuit is further configured to identify a position of the structure below the surface based on the reflected spectral light.

Example 3

The surgical visualization system of Examples 1 or 2, further comprising a three-dimensional camera comprising the image sensor, and wherein the image comprises a three-dimensional image.

Example 4

The surgical visualization system of Examples 1, 2, or 3, wherein the display screen comprises a digital proximity spectrum, and wherein the control circuit is further configured to display the distance from the surgical device to the structure on the digital proximity spectrum.

Example 5

The surgical visualization system of Example 4, wherein the digital proximity spectrum comprises a plurality of colors.

Example 6

The surgical visualization system of Example 4, wherein the digital proximity spectrum comprises a range of numerical values.

Example 7

The surgical visualization system of Example 4, wherein the digital proximity spectrum comprises a plurality of cross-hatching patterns corresponding to a range of distances.

Example 8

The surgical visualization system of Examples 1, 2, 3, 4, 5, 6, or 7, wherein the three-dimensional digital representation of the surface and a position of the structure are updated on the display screen in real time.

Example 9

The surgical visualization system of Examples 1, 2, 3, 4, 5, 6, 7, or 8, further comprising a robotic control unit in signal communication with the control circuit, wherein the surgical device is operably controlled by the robotic control unit, and wherein the robotic control unit is configured to adjust an operation of the surgical device when the distance from the surgical device to the structure is reduced to less than a minimum distance.

Example 10

The surgical visualization system of Examples 1, 2, 3, 4, 5, 6, 7, 8, or 9, further comprising a contrast agent in the structure, wherein the contrast agent is configured to illuminate the structure, and wherein the image sensor is configured to detect visible light reflected from the illuminated structure.

Example 11

The surgical visualization system of Examples 1, 2, 3, 4, 5, 6, 7, 8, 9, or 10, further comprising a second surgical device. The control circuit is further configured to determine a second distance from the second surgical device to the structure from the image, and provide the second distance to the image system.

Example 12

The surgical visualization system of Example 11, wherein the display screen is further configured to display the second surgical device and the second distance on a second proximity spectrum indicator.

Example 13

The surgical visualization system of Examples 11 or 12, wherein the control circuit is further configured to display a first alert when the distance from the surgical device to the structure is reduced to less than a first minimum distance, and display a second alert when the second distance from the second surgical device to the structure is reduced to less than a second minimum distance. The second minimum distance is different than the first minimum distance.

Example 14

The surgical visualization system of Examples 1, 2, 3, 4, 5, 6, 7, 8, 9, 10, 11, 12, or 13, wherein the control circuit is configured to triangulate the distance from known positions of the surgical device and the image sensor.

Example 15

A surgical visualization system comprising a processor and a memory communicatively coupled to the processor. The memory stores instructions executable by the processor to receive imaging data indicative of a structured light pattern on a surface, generate a three-dimensional digital representation of the surface based on the imaging data, and obtain an image of an embedded structure and a surgical device from an image sensor, overlay the image of the embedded structure and the surgical device with the three-dimensional digital representation of the surface on a display screen, and determine a distance from the surgical device to a portion of the surface covering the embedded structure.

Example 16

The surgical visualization system of Example 15, wherein a position of the embedded structure is identified with reflected spectral light capable of penetrating the surface and reaching the embedded structure.

Example 17

A non-transitory computer readable medium storing computer readable instructions which, when executed, cause a machine to receive imaging data indicative of a structured light pattern on a surface, generate a three-dimensional digital representation of the surface based on the imaging data, obtain a three-dimensional image of an embedded structure and a surgical device from an image sensor, overlay the image of the embedded structure and the surgical device with the three-dimensional digital representation of the surface on a display screen, and determine a distance from the surgical device to the embedded structure from the three-dimensional image.

Example 18

The non-transitory computer readable medium of Example 17, wherein the computer readable instructions, when executed, further cause the machine to provide a signal to the display screen indicative of the distance, and issue a warning signal when the distance meets a predefined threshold distance.

Example 19

A surgical visualization system comprising a display and a first robotic tool comprising a three-dimensional camera. The three-dimensional camera comprises an image sensor. The surgical visualization system further comprises a second robotic tool comprising a spectral light emitter configured to emit spectral light in a plurality of wavelengths capable of penetrating a surface and reaching a structure below the surface. The image sensor is configured to detect reflected visible light and reflected spectral light in the plurality of wavelengths. The surgical visualization system further comprises a control circuit in signal communication with the image sensor and the display. The control circuit is configured to obtain a three-dimensional image of the structure and the second robotic tool from the image sensor, determine a distance from the second robotic tool to the structure from the three-dimensional image, and provide a signal to the display indicative of the distance.

Example 20

The surgical visualization system of Example 19, wherein the second robotic tool further comprises a structured light emitter. The control circuit is further configured to receive imaging data indicative of a structured light pattern on a surface, generate a three-dimensional digital representation of the surface based on the imaging data, and provide a video signal to the display in which the three-dimensional image of the structure is integrated with the three-dimensional digital representation of the surface.

Example 21

A surgical visualization system comprising an emitter configured to emit a plurality of tissue-penetrating waveforms, a receiver configured to detect the plurality of tissue-penetrating waveforms, an imaging system comprising a display, and a control circuit in signal communication with the receiver. The control circuit is configured to receive data from the receiver representative of an image of a hidden portion of a surgical device, and provide the image of the hidden portion of the surgical device to the display.

Example 22

The surgical visualization system of Example 21, further comprising a hyperspectral camera comprising the emitter and the receiver.

Example 23

The surgical visualization system of Examples 21 or 22, further comprising a tissue surface mapping system comprising a structured light source. The control circuit is further configured to receive data from the tissue surface mapping system representative of a three-dimensional representation of a tissue surface, provide the three-dimensional representation of the tissue surface to the display, and overlay, on the display, the image of the hidden portion of the surgical device over the three-dimensional representation of the tissue surface.

Example 24

The surgical visualization system of Examples 21, 22, or 23, wherein the surgical device comprises a robotic surgical tool.

Example 25

The surgical visualization system of Examples 21, 22, or 23, wherein the surgical device comprises an aspirating needle.

Example 26

The surgical visualization system of Examples 21, 22, 23, 24, or 25, wherein the plurality of tissue-penetrating waveforms comprise a first waveform configured to target the hidden portion of the surgical device, and a second waveform configured to target an anatomical structure.

Example 27

The surgical visualization system of Example 26, wherein the control circuit is further configured to identify a first spectral signature corresponding to the hidden portion of the surgical device and a second spectral signature corresponding to the anatomical structure.

Example 28

The surgical visualization system of Examples 26 or 27, wherein the control circuit is further configured to determine a distance between the hidden portion of the surgical device and the anatomical structure.

Example 29

The surgical visualization system of Example 28, wherein the display is configured to convey the distance between the hidden portion of the surgical device and the anatomical structure.

Example 30

The surgical visualization system of Examples 28 or 29, wherein the control circuit is further configured to issue an alert when the distance between the hidden portion of the surgical device and the anatomical structure reaches a threshold minimum distance.

Example 31

The surgical visualization system of Examples 21, 22, 23, 24, 25, 26, 27, 28, 29, or 30, wherein the control circuit comprises a processor and a memory communicatively coupled to the processor. The memory stores instructions executable by the processor to receive data from the receiver representative of the image of the hidden portion of the surgical device, and provide the image of the hidden portion of the surgical device to the display.

Example 32

A surgical visualization system comprising a hyperspectral camera and a control circuit in signal communication with the hyperspectral camera. The hyperspectral camera comprises an emitter and an image sensor. The emitter is configured to emit a plurality of tissue-penetrating waveforms. The image sensor is configured to detect the plurality of tissue-penetrating waveforms. The control circuit is configured to receive data representative of a position of a first critical structure from the plurality of tissue-penetrating waveforms detected by the image sensor, receive data representative of a position of a second critical structure from the plurality of tissue-penetrating waveforms detected by the image sensor, and determine a distance between the first critical structure and the second critical structure.

Example 33

The surgical visualization system of Example 32, wherein the first critical structure comprises one of a surgical device and an anatomical structure.

Example 34

The surgical visualization system of Examples 32 or 33, wherein the second critical structure comprises one of a surgical device and an anatomical structure.

Example 35

The surgical visualization system of Examples 32, 33, or 34, wherein the control circuit comprises a processor and a memory communicatively coupled to the processor. The memory stores instructions executable by the processor to identify the first critical structure from the plurality of tissue-penetrating waveforms detected by the image sensor, identify the second critical structure from the plurality of tissue-penetrating waveforms detected by the image sensor, and determine the distance between the first critical structure and the second critical structure.

Example 36

The surgical visualization system of Examples 32, 33, 34, or 35, further comprising a video monitor, wherein the control circuit is further configured to schematically depict the first critical structure and the second critical structure on the video monitor in real time.

Example 37

The surgical visualization system of Examples 32, 33, 34, 35, or 36, wherein the emitter is further configured to emit a structured light pattern configured to reach a surface. The image sensor is further configured to detect the structured light pattern. The control circuit is further configured to receive data representative of a three-dimensional representation of the surface from the structured light pattern detected by the image sensor.

Example 38

The surgical visualization system of Example 37, wherein the control circuit is further configured to generate an image based on the three-dimensional representation of the surface, and overlay the schematic depiction of the first critical structure and the second critical structure on the image.

Example 39

A non-transitory computer readable medium storing computer readable instructions which, when executed, causes a machine to receive data from an image sensor representative of a first image of a first hidden structure, provide the first image of the first hidden structure to a display, receive data from the image sensor representative of a second image of a second hidden structure, provide the second image of the second hidden structure to the display, and determine a distance between the first hidden structure and the second hidden structure.

Example 40

The non-transitory computer readable medium of Example 39, wherein the computer readable instructions, when executed, further cause the machine to receive data from a receiver configured to detect a structured light pattern on a surface, generate a three-dimensional rendering of the surface from the data, provide the three-dimensional rendering of the surface to the display, and overlay, on the display, the first image of the first hidden structure and the second image on the second hidden structure over the three-dimensional rendering of the surface.

Example 41

A surgical visualization system comprising a first projector, a second projection, and a control circuit. The first projector is configured to emit a structured light pattern on a surface of an anatomical structure. The second projector is configured to emit spectral light in a plurality of wavelengths capable of penetrating the anatomical structure and reaching a staple line. The control circuit is in signal communication with an image sensor. The control circuit is configured to receive structured light data from the image sensor indicative of the structured light pattern on the surface of the anatomical structure, calculate a three-dimensional representation of the anatomical structure from the structured light data, receive spectral light data from the image sensor indicative of a spectral image of the staple line, generate the spectral image of the staple line from the spectral light data, and determine a distance with respect to the staple line.

Example 42

The surgical visualization system of Example 41, further comprising a video monitor, wherein the control circuit is in signal communication with the video monitor. The control circuit is further configured to selectively provide a first video signal to the video monitor indicative of the three-dimensional representation of the anatomical structure in real time. The control circuit is further configured to selectively provide a second video signal to the video monitor indicative of the position of the staple line in real time.

Example 43

The surgical visualization system of Example 42, wherein the control circuit is further configured to selectively integrate the first video signal and the second video signal to generate a video depicting the position of the staple line overlaying the three-dimensional representation of the anatomical structure.

Example 44

The surgical visualization system of Examples 42 or 43, wherein the control circuit is further configured to selectively provide a first signal to the video monitor indicative of the distance relative to the staple line.

Example 45

The surgical visualization system of Examples 41, 42, 43, or 44, wherein the control circuit is further configured to receive spectral light data from the image sensor indicative of a spectral image of a surgical end effector of a robotic tool. The control circuit is further configured to generate the spectral image of the surgical end effector from the spectral light data.

Example 46

The surgical visualization system of Example 45, wherein the control circuit is further configured to triangulate the distance between the surgical end effector and the staple line from the coordinates of the image sensor and the robotic tool.

Example 47

The surgical visualization system of Examples 41, 42, 43, or 44, wherein the control circuit is further configured to receive spectral light data from the image sensor indicative of a spectral image of a trocar of a circular stapler. The control circuit is further configured to generate the spectral image of the trocar from the spectral light data.

Example 48

The surgical visualization system of Example 47, wherein the control circuit is further configured to receive spectral light data from the image sensor indicative of a spectral image of a circular stapler anvil. The control circuit is further configured to generate the spectral image of the circular stapler anvil from the spectral light data.

Example 49

The surgical visualization system of Example 48, wherein the control circuit is further configured to determine a distance between the trocar and the circular stapler anvil.

Example 50

The surgical visualization system of Example 49, wherein the control circuit is further configured to provide a first signal indicative of the distance between the circular stapler anvil and the staple line to the video monitor. The control circuit is further configured to provide a second signal indicative of the distance between the trocar and the circular stapler anvil to the video monitor.

Example 51

The surgical visualization system of Examples 42 or 43, wherein the control circuit is further configured to provide the second video signal to the video monitor based on a user selection input to track the staple line.

Example 52

The surgical visualization system of Examples 41, 42, 43, 44, 45, 46, 47, 48, 49, 50, or 51, wherein the control circuit is in signal communication with a robotic control unit operably configured to control a robotic arm supporting a surgical device, and wherein the robotic control unit is operably configured to provide a control signal to move the robotic arm toward a portion of the anatomical structure obstructing the staple line from view.

Example 53

The surgical visualization system of Examples 41, 42, 43, 44, 45, 46, 47, 48, 49, 50, 51, or 52, further comprising a hyperspectral camera comprising the first projector, the second projector, and the image sensor.

Example 54

A surgical visualization system comprising a processor and a memory communicatively coupled to the processor. The memory stores instructions which, when executed by the processor receive structured light data from an image sensor indicative of a structured light pattern on a surface of an anatomical structure, calculate a three-dimensional representation of the anatomical structure from the structured light data, receive spectral light data from the image sensor indicative of a spectral image of a staple line, generate a spectral image of the staple line from the spectral light data, and determine a distance with respect to the staple line.

Example 55

The surgical visualization system of Example 54, wherein the memory stores instructions which, when executed by the processor selectively provide a first video signal to a video monitor indicative of the three-dimensional representation of the anatomical structure in real time, and selectively provide a second video signal to the video monitor indicative of the position of the staple line in real time.

Example 56

The surgical visualization system of Example 55, wherein the memory stores instructions which, when executed by the processor, selectively integrate the first video signal and the second video signal to generate a video depicting the position of the staple line overlaying the three-dimensional representation of the anatomical structure.

Example 57

The surgical visualization system of Examples 55 or 56, wherein the memory stores instructions which, when executed by the processor, selectively provide a first signal to the video monitor indicative of the distance relative to the staple line.

Example 58

A non-transitory computer readable medium storing computer readable instructions which, when executed, cause a machine to receive structured light data from an image sensor indicative of a structured light pattern on a surface of an anatomical structure, calculate a three-dimensional representation of the anatomical structure from the structured light data, receive spectral light data from the image sensor indicative of a spectral image of a staple line, generate a spectral image of the staple line from the spectral light data, and determine a distance with respect to the staple line.

Example 59

The non-transitory computer readable medium storing computer readable instructions of Example 58, which, when executed, further cause the machine to selectively provide a first video signal to a video monitor indicative of the three-dimensional representation of the anatomical structure in real time, and selectively provide a second video signal to the video monitor indicative of the position of the staple line in real time.

Example 60

The non-transitory computer readable medium storing computer readable instructions of Example 59, which, when executed, further cause the machine to selectively integrate the first video signal and the second video signal to generate a video depicting the position of the staple line overlaying the three-dimensional representation of the anatomical structure.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical visualization system, comprising:
   a first projector configured to emit a structured light pattern on a surface of an anatomical structure;
   a second projector configured to emit spectral light in a plurality of wavelengths capable of penetrating the anatomical structure and reaching a staple line; and
   a control circuit in signal communication with an image sensor, wherein the control circuit is configured to:
      receive structured light data from the image sensor indicative of the structured light pattern on the surface of the anatomical structure;
      calculate a three-dimensional representation of the anatomical structure from the structured light data;
      receive spectral light data from the image sensor indicative of a spectral image of the staple line;
      generate the spectral image of the staple line from the spectral light data; and
      determine a distance with respect to the staple line.

2. The surgical visualization system of claim 1, further comprising a video monitor, wherein the control circuit is in signal communication with the video monitor, and wherein the control circuit is further configured to:
   selectively provide a first video signal to the video monitor indicative of the three-dimensional representation of the anatomical structure in real time; and
   selectively provide a second video signal to the video monitor indicative of the position of the staple line in real time.

3. The surgical visualization system of claim 2, wherein the control circuit is further configured to selectively integrate the first video signal and the second video signal to generate a video depicting the position of the staple line overlaying the three-dimensional representation of the anatomical structure.

4. The surgical visualization system of claim 3, wherein the control circuit is further configured to selectively provide a first signal to the video monitor indicative of the distance relative to the staple line.

5. The surgical visualization system of claim 3, wherein the control circuit is further configured to:
   receive spectral light data from the image sensor indicative of a spectral image of a surgical end effector of a robotic tool; and
   generate the spectral image of the surgical end effector from the spectral light data.

6. The surgical visualization system of claim 5, wherein the control circuit is further configured to triangulate the distance between the surgical end effector and the staple line from the coordinates of the image sensor and the robotic tool.

7. The surgical visualization system of claim 3, wherein the control circuit is further configured to:
   receive spectral light data from the image sensor indicative of a spectral image of a trocar of a circular stapler; and
   generate the spectral image of the trocar from the spectral light data.

8. The surgical visualization system of claim 7, wherein the control circuit is further configured to:
   receive spectral light data from the image sensor indicative of a spectral image of a circular stapler anvil; and
   generate the spectral image of the circular stapler anvil from the spectral light data.

9. The surgical visualization system of claim 8, wherein the control circuit is further configured to determine a distance between the trocar and the circular stapler anvil.

10. The surgical visualization system of claim 9, wherein the control circuit is further configured to:
    provide a first signal indicative of the distance between the circular stapler anvil and the staple line to the video monitor; and
    provide a second signal indicative of the distance between the trocar and the circular stapler anvil to the video monitor.

11. The surgical visualization system of claim 3, wherein the control circuit is further configured to provide the second video signal to the video monitor based on a user selection input to track the staple line.

12. The surgical visualization system of claim 3, wherein the control circuit is in signal communication with a robotic control unit operably configured to control a robotic arm supporting a surgical device, and wherein the robotic control unit is operably configured to provide a control signal to move the robotic arm toward a portion of the anatomical structure obstructing the staple line from view.

13. The surgical visualization system of claim 1, further comprising a hyperspectral camera comprising the first projector, the second projector, and the image sensor.

14. A surgical visualization system, comprising:
    a processor; and
    a memory communicatively coupled to the processor, wherein the memory stores instructions which, when executed by the processor:
       receive structured light data from an image sensor indicative of a structured light pattern on a surface of an anatomical structure;
       calculate a three-dimensional representation of the anatomical structure from the structured light data;
       receive spectral light data from the image sensor indicative of a spectral image of a staple line;

generate a spectral image of the staple line from the spectral light data; and determine a distance with respect to the staple line.

15. The surgical visualization system of claim 14, wherein the memory stores instructions which, when executed by the processor:

selectively provide a first video signal to a video monitor indicative of the three-dimensional representation of the anatomical structure in real time; and selectively provide a second video signal to the video monitor indicative of the position of the staple line in real time.

16. The surgical visualization system of claim 15, wherein the memory stores instructions which, when executed by the processor, selectively integrate the first video signal and the second video signal to generate a video depicting the position of the staple line overlaying the three-dimensional representation of the anatomical structure.

17. The surgical visualization system of claim 16, wherein the memory stores instructions which, when executed by the processor, selectively provide a first signal to the video monitor indicative of the distance relative to the staple line.

18. A non-transitory computer readable medium storing computer readable instructions which, when executed, cause a machine to:

receive structured light data from an image sensor indicative of a structured light pattern on a surface of an anatomical structure;

calculate a three-dimensional representation of the anatomical structure from the structured light data;

receive spectral light data from the image sensor indicative of a spectral image of a staple line;

generate a spectral image of the staple line from the spectral light data; and determine a distance with respect to the staple line.

19. The non-transitory computer readable medium storing computer readable instructions of claim 18, which, when executed, further cause the machine to:

selectively provide a first video signal to a video monitor indicative of the three-dimensional representation of the anatomical structure in real time; and selectively provide a second video signal to the video monitor indicative of the position of the staple line in real time.

20. The non-transitory computer readable medium storing computer readable instructions of claim 19, which, when executed, further cause the machine to selectively integrate the first video signal and the second video signal to generate a video depicting the position of the staple line overlaying the three-dimensional representation of the anatomical structure.

* * * * *